US007280923B2

(12) United States Patent
Woods, Jr.

(10) Patent No.: US 7,280,923 B2
(45) Date of Patent: Oct. 9, 2007

(54) METHODS FOR CRYSTALLOGRAPHIC STRUCTURE DETERMINATION EMPLOYING HYDROGEN EXCHANGE ANALYSIS

(75) Inventor: Virgil L. Woods, Jr., San Diego, CA (US)

(73) Assignee: Regents of the University of California, Oakland, CA (US)

( * ) Notice: Subject to any disclaimer, the term of this patent is extended or adjusted under 35 U.S.C. 154(b) by 372 days.

(21) Appl. No.: 10/688,193

(22) Filed: Oct. 17, 2003

(65) Prior Publication Data

US 2004/0153256 A1 Aug. 5, 2004

Related U.S. Application Data

(60) Provisional application No. 60/419,651, filed on Oct. 18, 2002.

(51) Int. Cl.
*G01N 31/00* (2006.01)
(52) U.S. Cl. ....................................................... 702/27
(58) Field of Classification Search .................... None
See application file for complete search history.

(56) References Cited

U.S. PATENT DOCUMENTS

| 5,658,739 | A | 8/1997 | Woods, Jr. |
| 6,291,189 | B1 | 9/2001 | Woods, Jr. |
| 6,331,400 | B1 | 12/2001 | Woods, Jr. |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Dale et al. Crystal Enginerring: deletion mutagenesis of the 24 kDa fragment of the DNA gyrase B subunit from *Staphylococcus aureus*. Acta Crystallographica Section D. 1999. vol. D55, pp. 1626-1629.*
Pentazatos et al. Rapid Refinement of Crystallographic Protein Construct Definition Employing Enahnced Hydrogen/Deuterium Exchange MS. Proceedings of the Naitonal Academies of Science. 2004. vol. 101, No. 3, pp. 751-756.*
Cudney R. Protein Crystallization and Dumb Luck. The Rigaku Journal. 1999. vol. 16, No. 1, pp. 1-7.*
Bai et al., "Thermodynamic Parameters from Hydrogen Exchange Measurements," *Meth. Enzymol.* 259:344-356 (1995).
Bai et al., "Primary Structure Effects on Peptide Group Hydrogen Exchange," *Proteins: Struct. Funct. Genet.* 17:75-86 (1993).
Benjamin et al., "Long-Range Changes in a Protein Antigen Due to Antigen-Antibody Interaction," *Biochemistry*, 31:9539-9545 (1992).
Chi et al., "Use of Deuterium-Hydrogen Exchange to Characterize the Fragmentation Pathways of Arteether and its Metabolites in a Thermospray Mass Spectrometer," *Org. Mass Spectrometry* 7:58-62 (1993).

Connelly et al., "Isotope Effects in Peptide Group Hydrogen Exchange," *Proteins: Struct. Funct. Genet.* 17:87-92 (1993).
Deng and Smith, "Identification of Unfolding Domains in Large Proteins by Their Unfolding Rates," *Biochemistry* 37:6256-6262 (1998).
Dharmasiri and Smith, "Mass Spectrometric Determination of Isotopic Exchange Rates of Amide Hydrogens Located on the Surfaces of Proteins," *Anal. Chem.* 68:2340-2344 (1996).
Engen and Smith, "A Powerful New Approach That Goes Beyond Deciphering Protein Structures," *Anal. Chem.* 73:256A-265A (2001).
Englander and Englander, "Structure and Energy Change in Hemoglobin by Hydrogen Exchange Labeling," *Meth. Enzymol.* 232:26-42 (1994).
Englander et al., "Protein Hydrogen Exchange Studied by the Fragment Separation Method," *Anal. Biochem.* 147:234-244 (1985).
Englander et al., "Individual Breathing Reactions Measured in Hemoglobin by Hydrogen Exchange Methods," *Biophys. J.* 10:577-589 (1979).
Englander and Poulsen, "Hydrogen-Tritium Exchange of the Random Chain Polypeptide," *Biopolymers* 7:379-393 (1969).
Englander and Rolfe, "Hydrogen Exchange Studies of Respiratory Proteins," *J. Biol. Chem.* 248:4852-4861 (1973).
Englander and Englander, "Hydrogen-Tritium Exchange," *Meth. Enzymol.* 26:406-413 (1972).
Englander et al., "Hydrogen-Tritium Exchange," *Meth. Enzymol.* 49:24-39 (1978).
Englander et al., "Protein Structure Change Studied by Hydrogen-Deuterium Exchange, Functional Labeling, and Mass Spectrometry," *Proc. Natl. Acad. Sci. USA* 100:7057-7062 (2003).
Englander et al., "Hydrogen Exchange: The Modern Legacy of Linderstrom-Lang," *Protein Sci.* 6:1101-1109 (1997).
Englander and Englander, "Hydrogen-Tritium Exchange Survey of Allosteric Effects in Hemoglobin," *Biochemistry* 26:1846-1850 (1987).
Fesik et al. "Amide Proton Exchange Rates of a Bound Pepsin Inhibitor Determined by Isotope-Edited Proton NMR Experiments," *Biochem. Biophys. Res. Commun.* 147:892-898, (1987).
Hamuro et al., "Domain Organization of D-AKAP2 Revealed by Enhanced Deuterium Exchange-Mass Spectrometry (DXMS)," *J. Mol. Biol.*, 321: 703-714 (2002).

(Continued)

*Primary Examiner*—Kathleen Kerr Bragdon
*Assistant Examiner*—Suzanne M. Noakes
(74) *Attorney, Agent, or Firm*—Foley & Lardner LLP; Stephen E. Reiter

(57) ABSTRACT

The present invention provides methods for crystallographic structure determination employing hydrogen exchange analysis. Hydrogen exchange analysis is used to identify unstructured regions of a protein, which are then deleted to obtain one or more modified proteins for crystallization and structure determination. Optionally, an initial hydrogen exchange stability map of a protein is compared to that of at least one modified form of the protein to identify unstructured regions, while retaining characteristic structure of the native protein. Hydrogen exchange analysis is performed by determining the quantity of isotope and/or rate of exchange of peptide amide hydrogen(s) with isotope on a labeled protein. Proteins with fewer unstructured regions, and thus improved hydrogen exchange structural maps, are optimal for high quality crystallization and structure determination.

42 Claims, 24 Drawing Sheets

OTHER PUBLICATIONS

Hamuro et al., "Phosphorylation Driven Motions in the COOH-Terminal Src Kinase, Csk, Revealed Through Enhanced Hydrogen-Deuterium Exchange and Mass Spectrometry," *J. Mol. Biol.* 323:871-881 (2002).

Hamuro et al., "Dynamics of cAPK Type IIβ Activation Revealed by Enhanced Amide H/$^2$H Exchange Mass Spectrometry (DXMS)," *J. Mol. Biol.* 327:1065-1076 (2003).

Hoofnagle et al., "Changes in Protein Conformational Mobility Upon Activation of Extracellular Regulated Protein Kinase-2 as Detected by Hydrogen Exchange," *Proc. Natl. Acad. Sci. USA* 98:956-961 (2001).

Katta and Chait, "Hydrogen/Deuterium Exchange Electrospray Ionization Mass Spectrometry: A Method of Probing Protein Conformational Changes in Solution," *J. Am. Chem. Soc.* 115:6317-6321 (1993).

Kim and Baldwin, "Influence of Charge on the Rate of Amide Proton Exchange," *Biochemistry* 21:1-5 (1982).

Louie et al., "Salt, Phosphate and the Bohr Effect at the Hememoglobin Beta Chain C Terminus Studied by Hydrogen Exchange," *J. Mol. Biol.* 201:765-772 (1988).

Mandell et al., "Measurement of Amide Hydrogen Exchange by MALDI-TOF Mass Spectrometry," *Anal. Chem.* 70:3987-3995 (1998).

Mayne et al., "Effect of Antibody Binding on Protein Motions Studied by Hydrogen-Exchange Labeling and Two-Dimensional NMR," *Biochemistry* 31:10678-10685 (1992).

McCloskey, "Introduction of Deuterium by Exchange for Measurement by Mass Spectrometry," *Meth. Enzymol.* 193:329-338 (1990).

Molday et al., "Primary Structure Effects on Peptide Group Hydrogen Exchange," *Biochemistry* 11:150-158 (1972).

Paterson et al. "An Antibody Binding Site on Cytochrome c Defined by Hydrogen Exchange and Two-Dimensional NMR," *Science* 249:755-759 (1990).

Pedersen et al., "A Nuclear Magnetic Resonance Study of the Hydrogen-Exchange Behavior of Lysozyme in Crystals and Solution," *J.Mol.Biol.*, 213:413-426 (1990).

Resing and Ahn, "Deuterium Exchange Mass Spectrometry as a Probe of Protein Kinase Activation. Analysis of Wild-Type and Constitutively Active Mutants of MAP Kinase Kinase-1," *Biochemistry* 37:463-475 (1998).

Resing and Ahn, "Protein Phosphorylation Analysis by Electrospray Ionization-Mass Spectrometry," *Meth. Enzymol.* 283:29-44 (1997).

Resing et al., "Modeling Deuterium Exchange Behavior of ERK2 Using Pepsin Mapping to Probe Secondary Structure," *J. Am. Soc. Mass Spectrometry* 10:685-702 (1999).

Rogero et al., "Individual Breathing Reactions Measured by Functional Labeling and Hydrogen Exchange Methods," *Meth. Enzymol.* 131:508-517 (1986).

Rosa and Richards et al., "An Experimental Procedure for Increasing the Structural Resolution of Chemical Hydrogen-exchange Measurements on Proteins: Application to Ribonuclease S Peptide," *J. Mol. Biol.* 133:399-416 (1979).

Rosa et al., "Hydrogen Exchange from Identified Regions of the S-Protein Component of Ribonuclease as a Function of Temperature, pH, and the Binding of S-Peptide," *J. Mol. Biol.* 145:835-851 (1981).

Rosa et al., "Effects of Binding of S-Peptide and 2'-Cytidine Monophosphate on Hydrogen Exchange from the S-Protein Component of Ribonuclease," *J. Mol. Biol.* 160:517-530 (1982).

Smith et al., "Probing the Non-covalent Structure of Proteins by Amide Hydrogen Exchange and Mass Spectrometry," *J. Mass Spectrometry* 32:135-146 (1997).

Thevenon-Emeric et al., "Determination of Amide Hydrogen Exchange Rates in Peptides by Mass Spectrometry," *Anal. Chem.* 64:2456-2358 (1992).

Wang, et al., "Hydrogen Exchange-Mass Spectrometry," *Moll. Cell Proteom*, 1:132-138 (2002) (we have a copy in the file).

Winger et al., "Probing Qualitative Conformation Differences of Multiply Protonated Gas-Phase Proteins via H/D Isotopic Exchange with $D_2O$," *J. Am. Chem. Soc.* 114:5897-5989 (1992).

Woods and Hamuro, "High Resolution, High-Throughput Amide Deuterium Exchange-Mass Spectrometry (DXMS) Determination of Protein Binding Site Structure and Dynamics: Utility in Pharmaceutical Design," *J. Cell. Biochem.*, 37:89-98 (2001), pub on line Jan. 29, 2002.

Zawadzki et al., "Dissecting Interdomain Communication Within cAPK Regulatory Subunit Type IIβ Using Enhanced Amide Hydrogen/Deuterium Exchange Mass Spectrometry," *Protein Sci.* 12:1980-1990 (2003).

Zhang and Smith, "Determination of Amide Hydrogen Exchange b Mass Spectrometry: A New Tool for Protein Structure Elucidation," *Prot. Sci.* 2:522-531 (1993).

Kwong et al., "Probability Analysis of Variational Crystallization and Its Application to gp 120, The Exterior Envelope Glycoprotein of Type 1 Human Immunodeficiency Virus (HIV-1)", Journal of Biological Chemistry, 274(7): 4115-4123, 1999.

Supplementary European Search Report for Application No. 03809119.5.

* cited by examiner

```
  2        10        20        30        40        50        60        70
SIEIPAGLTELLQGFTVEVLRHQPADLLEFALQHFTRLQQENERKGAARFGHEGRTWGDAGAAAGGGTPSKGVNF 80        90       100       110       120       130       140       150
AEEPMRSDSENGEEEEAAEAGAFNAPVINRFTRRASVCAEAYNPDEEEDDAESRIIHPKTDDQRNRLQEACKDIL 160       170       180       190       200       210
LFKNLDPEQMSQVLDAMFEKLVKEGEHVIDQGDDGDNFYVIDRGTFDIYVKCDGVGRCVGNYDNRGSF
220       230       240       250       260
GELALMYNTPRAATITATSPGALWGLDRVTFRRIIVKNNAKKRKMYESF
270       280       290       300       310       320       330
IESLPFLKSLEVSERLKVVDVIGTKVYNDGEQIIAQGDSADSFFIVESGEVRITMKRKGKSDIEENGAVE
340       350       360       370       380       390       400       410
IARCLRGQYFGELALVTNKPRAASAHAIGTVKCLAMDVQAFERLLGPCMEIMKRNIATYEEQLVALFGTNMDIVEPTA
```

FIGURE 12

SEQUENCE LISTING

```
<160> NUMBER OF SEQ ID NOS: 17

<210> SEQ ID NO 1
<211> LENGTH: 104
<212> TYPE: PRT
<213> ORGANISM: Equus caballus

<400> SEQUENCE: 1

Gly Asp Val Glu Lys Gly Lys Lys Ile Phe Val Gln Lys Cys Ala Gln
1               5                   10                  15

Cys His Thr Val Glu Lys Gly Gly Lys His Lys Thr Gly Pro Asn Leu
            20                  25                  30

His Gly Leu Phe Gly Arg Lys Thr Gly Gln Ala Pro Gly Phe Thr Tyr
        35                  40                  45

Thr Asp Ala Asn Lys Asn Lys Gly Ile Thr Trp Lys Glu Glu Thr Leu
    50                  55                  60

Met Glu Tyr Leu Glu Asn Pro Lys Lys Tyr Ile Pro Gly Thr Lys Met
65                  70                  75                  80

Ile Phe Ala Gly Ile Lys Lys Lys Thr Glu Arg Glu Asp Leu Ile Ala
                85                  90                  95

Tyr Leu Lys Lys Ala Thr Asn Glu
            100

<210> SEQ ID NO 2
<211> LENGTH: 289
<212> TYPE: PRT
<213> ORGANISM: Homo sapiens

<400> SEQUENCE: 2
```

Ser Gly Lys Lys Val Thr Leu Asn Pro Ser Asp Pro Glu His Gly Gln
1               5                   10                  15

Ile Gly His Gly Asp Val Val Asn Leu Thr Gly Glu Ala Gly Gln Glu
                20                  25                  30

Pro Gly Gly Leu Val Val Pro Thr Asp Ala Pro Val Ser Pro Thr
            35                  40                  45

Thr Leu Tyr Val Glu Asp Ile Ser Glu Pro Pro Leu His Asp Phe Tyr
    50                  55                      60

Cys Ser Arg Leu Leu Asp Leu Val Phe Leu Leu Asp Gly Ser Ser Arg
65                  70                  75                  80

Leu Ser Glu Ala Glu Phe Glu Val Leu Lys Ala Phe Val Val Asp Met
                85                  90                  95

Met Glu Arg Leu Arg Val Ser Gln Lys Trp Val Arg Val Ala Val Val
            100                 105                 110

Glu Tyr His Asp Gly Ser His Ala Tyr Ile Gly Leu Lys Asp Arg Lys
        115                 120                 125

Arg Pro Ser Glu Leu Arg Arg Ile Ala Ser Gln Val Lys Tyr Ala Gly
130                 135                 140

Ser Gln Val Ala Ser Thr Ser Glu Val Leu Lys Tyr Thr Leu Phe Gln
145                 150                 155                 160

Ile Phe Ser Lys Ile Asp Arg Pro Glu Ala Ser Arg Ile Ala Leu Leu
                165                 170                 175

Leu Met Ala Ser Gln Glu Pro Gln Arg Met Ser Arg Asn Phe Val Arg
            180                 185                 190

Tyr Val Gln Gly Leu Lys Lys Lys Val Ile Val Ile Pro Val Gly
        195                 200                 205

Ile Gly Pro His Ala Asn Leu Lys Gln Ile Arg Leu Ile Glu Lys Gln
    210                 215                 220

Ala Pro Glu Asn Lys Ala Phe Val Leu Ser Ser Val Asp Glu Leu Glu
225                 230                 235                 240

Gln Gln Arg Asp Glu Ile Val Ser Tyr Leu Cys Asp Leu Ala Pro Glu
            245                 250                 255

Ala Pro Pro Pro Thr Leu Pro Pro His Met Ala Gln Val Thr Val Gly
            260                 265                 270

Pro Gly Leu Leu Gly Val Ser Thr Leu Gly Pro Lys Arg Asn Ser Met
        275                 280                 285

Val

<210> SEQ ID NO 3
<211> LENGTH: 213
<212> TYPE: PRT
<213> ORGANISM: Gallus gallus

<400> SEQUENCE: 3

Met Val His Gln Phe Phe Arg Asp Met Asp Asp Glu Glu Ser Trp Ile
1               5                   10                  15

Lys Glu Lys Lys Leu Leu Val Ser Ser Glu Asp Tyr Gly Arg Asp Leu
                20                  25                  30

Thr Gly Val Gln Asn Leu Arg Lys Lys His Lys Arg Leu Glu Ala Glu
            35                  40                  45

Leu Ala Ala His Glu Pro Ala Ile Gln Ser Val Leu Asp Thr Gly Lys
    50                  55                      60

Lys Leu Ser Asp Asp Asn Thr Ile Gly Lys Glu Glu Ile Gln Gln Arg
65                  70                  75                  80

```
Leu Ala Gln Phe Val Asp His Trp Lys Glu Leu Lys Gln Leu Ala Ala
                    85                  90                  95

Ala Arg Gly Gln Arg Leu Glu Glu Ser Leu Glu Tyr Gln Gln Phe Val
            100                 105                 110

Ala Asn Val Glu Glu Glu Ala Trp Ile Asn Glu Lys Met Thr Leu
            115                 120                 125

Val Ala Ser Glu Asp Tyr Gly Asp Thr Leu Ala Ala Ile Gln Gly Leu
        130                 135                 140

Leu Lys Lys His Glu Ala Phe Glu Thr Asp Phe Thr Val His Lys Asp
145                 150                 155                 160

Arg Val Asn Asp Val Cys Ala Asn Gly Glu Asp Leu Ile Lys Lys Asn
                165                 170                 175

Asn His His Val Glu Asn Ile Thr Ala Lys Met Lys Gly Leu Lys Gly
            180                 185                 190

Lys Val Ser Asp Leu Glu Lys Ala Ala Gln Arg Lys Ala Lys Leu
            195                 200                 205

Asp Glu Asn Ser Ala
        210

<210> SEQ ID NO 4
<211> LENGTH: 213
<212> TYPE: PRT
<213> ORGANISM: Gallus gallus

<400> SEQUENCE: 4

Met Val His Gln Phe Phe Arg Asp Met Asp Asp Glu Glu Ser Trp Ile
 1               5                  10                  15

Lys Glu Lys Lys Leu Leu Val Ser Ser Glu Asp Tyr Gly Arg Asp Leu
            20                  25                  30

Thr Gly Val Gln Asn Leu Arg Lys Lys His Lys Arg Leu Glu Ala Glu
        35                  40                  45

Leu Ala Ala His Glu Pro Ala Ile Gln Ser Val Leu Asp Thr Gly Lys
    50                  55                  60

Lys Leu Ser Asp Asp Asn Thr Ile Gly Lys Glu Ile Gln Gln Arg
65                  70                  75                  80

Leu Ala Gln Phe Val Asp His Trp Lys Glu Leu Lys Gln Leu Ala Ala
                    85                  90                  95

Ala Arg Gly Gln Arg Leu Glu Glu Ser Leu Glu Tyr Gln Gln Phe Val
            100                 105                 110

Ala Asn Val Glu Glu Glu Ala Trp Ile Asn Glu Lys Met Thr Leu
            115                 120                 125

Val Ala Ser Glu Asp Tyr Gly Asp Thr Leu Ala Ala Ile Gln Gly Leu
        130                 135                 140

Leu Lys Lys His Glu Ala Phe Glu Thr Asp Phe Thr Val His Lys Asp
145                 150                 155                 160

Arg Val Asn Asp Val Cys Ala Asn Gly Glu Asp Leu Ile Lys Lys Asn
                165                 170                 175

Asn His His Val Glu Asn Ile Thr Ala Lys Met Lys Gly Leu Lys Gly
            180                 185                 190

Lys Val Ser Asp Leu Glu Lys Ala Ala Gln Arg Lys Ala Lys Leu
            195                 200                 205

Asp Glu Asn Ser Ala
        210
```

<210> SEQ ID NO 5
<211> LENGTH: 415
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 5

```
Ser Ile Glu Ile Pro Ala Gly Leu Thr Glu Leu Leu Gln Gly Phe Thr
  1               5                  10                  15

Val Glu Val Leu Arg His Gln Pro Ala Asp Leu Leu Glu Phe Ala Leu
             20                  25                  30

Gln His Phe Thr Arg Leu Gln Gln Glu Asn Glu Arg Lys Gly Ala Ala
         35                  40                  45

Arg Phe Gly His Glu Gly Arg Thr Trp Gly Asp Gly Ala Ala Ala
     50                  55                  60

Gly Gly Gly Thr Pro Ser Lys Gly Val Asn Phe Ala Glu Glu Pro Met
 65                  70                  75                  80

Arg Ser Asp Ser Glu Asn Gly Glu Glu Glu Ala Ala Glu Ala Gly
             85                  90                  95

Ala Phe Asn Ala Pro Val Ile Asn Arg Phe Thr Arg Arg Ala Ser Val
            100                 105                 110

Cys Ala Glu Ala Tyr Asn Pro Asp Glu Glu Asp Asp Ala Glu Ser
            115                 120                 125

Arg Ile Ile His Pro Lys Thr Asp Asp Gln Arg Asn Arg Leu Gln Glu
130                 135                 140

Ala Cys Lys Asp Ile Leu Leu Phe Lys Asn Leu Asp Pro Glu Gln Met
145                 150                 155                 160

Ser Gln Val Leu Asp Ala Met Phe Glu Lys Leu Val Lys Glu Gly Glu
                165                 170                 175

His Val Ile Asp Gln Gly Asp Asp Gly Asp Asn Phe Tyr Val Ile Asp
            180                 185                 190

Arg Gly Thr Phe Asp Ile Tyr Val Lys Cys Asp Gly Val Gly Arg Cys
        195                 200                 205

Val Gly Asn Tyr Asp Asn Arg Gly Ser Phe Gly Glu Leu Ala Leu Met
    210                 215                 220

Tyr Asn Thr Pro Arg Ala Ala Thr Ile Thr Ala Thr Ser Pro Gly Ala
225                 230                 235                 240

Leu Trp Gly Leu Asp Arg Val Thr Phe Arg Arg Ile Ile Val Lys Asn
                245                 250                 255

Asn Ala Lys Lys Arg Lys Met Tyr Glu Ser Phe Ile Glu Ser Leu Pro
            260                 265                 270

Phe Leu Lys Ser Leu Glu Val Ser Glu Arg Leu Lys Val Val Asp Val
        275                 280                 285

Ile Gly Thr Lys Val Tyr Asn Asp Gly Glu Gln Ile Ile Ala Gln Gly
    290                 295                 300

Asp Ser Ala Asp Ser Phe Phe Ile Val Glu Ser Gly Glu Val Arg Ile
305                 310                 315                 320

Thr Met Lys Arg Lys Gly Lys Ser Asp Ile Glu Glu Asn Gly Ala Val
                325                 330                 335

Glu Ile Ala Arg Cys Leu Arg Gly Gln Tyr Phe Gly Glu Leu Ala Leu
            340                 345                 350

Val Thr Asn Lys Pro Arg Ala Ala Ser Ala His Ala Ile Gly Thr Val
        355                 360                 365
```

```
Lys Cys Leu Ala Met Asp Val Gln Ala Phe Glu Arg Leu Leu Gly Pro
            370                 375                 380

Cys Met Glu Ile Met Lys Arg Asn Ile Ala Thr Tyr Glu Glu Gln Leu
385                 390                 395                 400

Val Ala Leu Phe Gly Thr Asn Met Asp Ile Val Glu Pro Thr Ala
                405                 410                 415

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ile Glu Ile Pro Ala Gly Leu Thr Glu Leu Leu Gln Gly Phe Thr
 1               5                   10                  15

Val Glu Val Leu Arg His Gln Pro Ala Asp Leu
            20                  25

<210> SEQ ID NO 7
<211> LENGTH: 102
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Leu Glu Phe Ala Leu Gln His Phe Thr Arg Leu Gln Gln Glu Asn
 1               5                   10                  15

Glu Arg Lys Gly Ala Ala Arg Phe Gly His Gly Arg Thr Trp Gly
            20                  25                  30

Asp Ala Gly Ala Ala Ala Gly Gly Gly Thr Pro Ser Lys Gly Val Asn
            35                  40                  45

Phe Ala Glu Glu Pro Met Arg Ser Asp Ser Glu Asn Gly Glu Glu Glu
     50                  55                  60

Glu Ala Ala Glu Ala Gly Ala Phe Asn Ala Pro Val Ile Asn Arg Phe
65                  70                  75                  80

Thr Arg Arg Ala Ser Val Cys Ala Glu Ala Tyr Asn Pro Asp Glu Glu
                85                  90                  95

Glu Asp Asp Ala Glu Ser
            100

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Glu Leu Ala Leu Met Tyr Asn Thr Pro Arg Ala Ala Thr Ile Thr
 1               5                   10                  15

Ala

<210> SEQ ID NO 9
<211> LENGTH: 31
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 9

Ala Val Glu Ile Ala Arg Cys Leu Arg Gly Gln Tyr Phe Gly Glu Leu
 1               5                  10                  15

Ala Leu Val Thr Asn Lys Pro Arg Ala Ala Ser Ala His Ala Ile
            20                  25                  30

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gln Gly Asp Ser Ala Asp Ser Phe Phe Ile Val Glu Ser Gly Glu
 1               5                  10                  15

Val Arg Ile Thr Met Lys Arg
            20

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Gln Ala Phe Glu Arg Leu
 1               5

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Lys Arg Asn Ile Ala Thr Tyr Glu Glu Gln Leu Val Ala Leu Phe
 1               5                  10                  15

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Leu Leu Phe Lys
 1               5

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Val Thr Phe Arg Arg Ile Ile Val Lys Asn Asn Ala Lys Lys Arg
1               5                   10                  15

Lys Met Tyr Glu Ser Phe Ile Glu Ser Leu Pro Phe Leu Lys
            20                  25                  30

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Gln Ala Phe Glu Arg Leu Leu Gly Pro Cys Met
1               5                   10

<210> SEQ ID NO 16
<211> LENGTH: 193
<212> TYPE: PRT
<213> ORGANISM: Thermotoga maritima

<400> SEQUENCE: 16

Met Gly Ser Asp Lys Ile His His His His His Met Arg Lys Ala
1               5                   10                  15

Trp Val Lys Thr Leu Ala Leu Asp Arg Val Ser Asn Thr Pro Val Val
            20                  25                  30

Ile Leu Gly Ile Glu Gly Thr Asn Arg Val Leu Pro Ile Trp Ile Gly
        35                  40                  45

Ala Cys Glu Gly His Ala Leu Ala Leu Ala Met Glu Lys Met Glu Phe
    50                  55                  60

Pro Arg Pro Leu Thr His Asp Leu Leu Leu Ser Val Leu Glu Ser Leu
65                  70                  75                  80

Glu Ala Arg Val Asp Lys Val Ile Ile His Ser Leu Lys Asp Asn Thr
                85                  90                  95

Phe Tyr Ala Thr Leu Val Ile Arg Asp Leu Thr Tyr Thr Asp Glu Glu
            100                 105                 110

Asp Glu Glu Ala Ala Leu Ile Asp Ile Asp Ser Arg Pro Ser Asp Ala
        115                 120                 125

Ile Ile Leu Ala Val Lys Thr Gly Ala Pro Ile Phe Val Ser Asp Asn
    130                 135                 140

Leu Val Glu Lys His Ser Ile Glu Leu Glu Val Asn Glu Thr Gln Asp
145                 150                 155                 160

Glu Glu Glu Glu Phe Lys Lys Phe Val Glu Asn Leu Asn Ile Asp Thr
                165                 170                 175

Phe Lys Gln Met Ile Glu Lys Lys Arg Glu Glu Asp Glu Glu Gly Glu
            180                 185                 190

Ser

<210> SEQ ID NO 17
<211> LENGTH: 157
<212> TYPE: PRT
<213> ORGANISM: Thermotoga maritima

<400> SEQUENCE: 17

Met Gly Ser Asp Lys Ile His His His His His Met Arg Lys Ala
1               5                   10                  15

```
Trp Val Lys Thr Leu Ala Leu Asp Arg Val Ser Asn Thr Pro Val Val
            20                  25              30

Ile Leu Gly Ile Glu Gly Thr Asn Arg Val Leu Pro Ile Trp Ile Gly
            35              40                  45

Ala Cys Glu Gly His Ala Leu Ala Leu Ala Met Glu Lys Met Glu Phe
        50              55              60

Pro Arg Pro Leu Thr His Asp Leu Leu Leu Ser Val Leu Glu Ser Leu
65              70                  75                      80

Glu Ala Arg Val Asp Lys Val Ile Ile His Ser Leu Lys Asp Asn Thr
            85              90                  95

Phe Tyr Ala Thr Leu Val Ile Arg Asp Leu Thr Tyr Thr Asp Glu Glu
            100             105             110

Asp Glu Glu Ala Ala Leu Ile Asp Ile Asp Ser Arg Pro Ser Asp Ala
        115             120             125

Ile Ile Leu Ala Val Lys Thr Gly Ala Pro Ile Phe Val Ser Asp Asn
        130             135             140

Leu Val Glu Lys His Ser Ile Glu Leu Glu Val Asn Glu
145             150             155
```

METHODS FOR CRYSTALLOGRAPHIC STRUCTURE DETERMINATION EMPLOYING HYDROGEN EXCHANGE ANALYSIS

RELATED APPLICATIONS

This application claims the benefit of U.S. Provisional Application No. 60/419,651, filed Oct. 18, 2002, the contents of which are incorporated herein in their entirety.

FIELD OF THE INVENTION

The present invention relates to methods for determining polypeptide structure using crystallography. In a particular aspect, the invention relates to methods for crystallographic structure determination that employ hydrogen exchange analysis.

BACKGROUND OF THE INVENTION

Considerable experimental work and time are required to precisely characterize the structure of a polypeptide of interest. In general, the techniques that are the easiest to use and which give the quickest answers, result in an inexact and only approximate idea of the nature of the critical structural features. Techniques in this category include the study of proteolytically generated fragments of the protein which retain binding function; recombinant DNA techniques, in which proteins are constructed with altered amino acid sequence (for example, by site directed mutagenesis); epitope scanning peptide studies (construction of a large number of small peptides representing subregions of the intact protein followed by study of the ability of the peptides to inhibit binding of the ligand to receptor); covalent crosslinking of the protein to its binding partner in the area of the binding site, followed by fragmentation of the protein and identification of cross-linked fragments; and affinity labeling of regions of the receptor which are located near the ligand binding site of the receptor, followed by characterization of such "nearest neighbor" peptides.

Other techniques that are capable of finely characterizing polypeptide three-dimensional structure are considerably more difficult in practice. The most definitive techniques for the characterization of polypeptide structure, and receptor binding sites in particular, have been NMR spectroscopy and X-ray crystallography. While these techniques can ideally provide a precise characterization of relevant structural features, they have major limitations, including inordinate amounts of time required for study, inability to study large proteins, and, for X-ray analysis, the need for protein and/or protein-binding partner crystals.

A critical shortcoming of present high-throughput crystallographic structure determination efforts is the failure to produce crystals for around 80% of the proteins of interest. It is clear that advances in automation and crystallography data analysis have not been matched by a similar pace of progress in methods for generating protein crystals for analysis (Chayen and Saridakis, *Acta Crystal. D. Biol. Crystal.* 58:921-927, 2002). The process of generating protein crystals suitable for structural analysis is commonly recognized as the most difficult and time-consuming step in the process of a crystallographic structure determination (see, e.g., Wiencek, *Ann. Rev. Biomed. Eng.* 1:505-534, 1999). Floppy, unstructured regions of proteins can play a dominant role in this problem; the energetics and kinetics of crystallization are often less favorable than for fully structured proteins, and additionally, these regions are often more susceptible to degradation during purification than are structured regions, thus promoting sample heterogeneity.

Measurement of the exchange rates of peptide amide hydrogens within a protein can report its stability at the individual amino acid scale. Essentially, hydrogen exchange can be used to determine a stability map of a protein, reflecting the degree of ordered conformation of all regions of the protein being analyzed. Ranking and comparison of the exchange rates of a protein's amide hydrogens therefore allows direct identification and localization of structured versus unstructured regions of the protein.

Accordingly, there is considerable advantage in producing modified forms of proteins of interest that contain structured regions in their native conformation, but have unstructured regions modified or removed (in part, or in whole). Thus, there remains a need in the art for a robust technique to discern structured versus unstructured regions of proteins of interest at the pace required for high-throughput crystallographic structure determination.

Hydrogen (Proton) Exchange

When a protein in its native folded state is incubated in buffers containing an isotope of hydrogen (for example, tritium or deuterium labeled water), isotope in the buffer reversibly exchanges with normal hydrogen present in the protein at acidic positions (for example, —OH, —SH, and —NH groups) with rates of exchange which are dependent on each exchangeable hydrogen's chemical environment, temperature, and most importantly, its accessibility to the isotope of hydrogen present in the buffer (see, e.g., Englander et al., *Meth. Enzymol.* 49:24-39,1978; Englander et al., *Meth. Enzymol.* 26:406-413, 1972). Accessibility is determined in turn by both the surface (solvent-exposed) disposition of the hydrogen, and the degree to which it is hydrogen-bonded to other regions of the folded polypeptide. Simply stated, an acidic hydrogen present on amino acid residues which are on the outside (buffer-exposed) surface of the protein and which are hydrogen-bonded to solvent water will often exchange more rapidly with heavy hydrogen in the buffer than will a similar acidic hydrogen which is buried and hydrogen-bonded within the folded polypeptide.

Hydrogen exchange reactions can be greatly accelerated by both acid and base-mediated catalysis; and the rate of exchange observed at any particular pH is the sum of both acid and base mediated mechanisms. For many acidic hydrogens, a pH of 2.2-2.7 results in an overall minimum rate of exchange (Englander et al., *Anal. Biochem.* 147:234-244, 1985; Englander et al., *Biopolymers* 7:379-393, 1969; Molday et al., *Biochemistry* 11:150, 1972; Kim et al., *Biochemistry* 21:1, 1982; Bai et al., *Proteins: Struct. Funct. Genet.* 17:75-86,1993; and Connelly et al., *Proteins: Struct. Funct. Genet.* 17:87-92). While hydrogens in protein hydroxyl and amino groups exchange with tritium or deuterium in buffer at millisecond rates, the exchange rate of one particular acidic hydrogen, the peptide amide bond hydrogen, is considerably slower, having a half life of exchange (when freely accessible, and freely hydrogen-bonded to solvent water) of approximately 0.5 seconds at 0° C., pH 7, which is greatly slowed to a half life of exchange of 70 minutes at 0° C., pH 2.7. When a polypeptide is in a denatured, unstructured configuration (also termed a "random coil") all of its amide hydrogens can freely exchange with solvent hydrogen. However, the precise rate of exchange varies up to 200 fold from amide to amide in such unstructured configurations, the rate of exchange at each particular amide being determined by localized primary amino acid sequence-dependent effects that can be calculated from a knowledge of the peptide's primary sequence (Bai et al., supra). When peptide amide hydrogens are buried within a folded polypeptide, or are hydrogen bonded to other parts of the polypeptide, exchange half-lives with solvent hydrogens are often considerably lengthened, at times being measured in hours to days.

Hydrogen exchange at peptide amides is a fully reversible reaction, and rates of on-exchange (solvent deuterium replacing protein-bound normal hydrogen) are identical to rates of off-exchange (hydrogen replacing protein-bound deuterium) if the state of a particular peptide amide within a protein, including its chemical environment and accessibility to solvent hydrogens, remains identical during hydrogen exchange conditions.

Hydrogen exchange is commonly measured by performing studies with proteins and aqueous buffers that are differentially tagged with pairs of the three isotopic forms of hydrogen ($^1H$, normal hydrogen; $^2H$, deuterium; $^3H$, tritium). If the pair of normal hydrogen and tritium are employed, it is referred to as tritium exchange; if normal hydrogen and deuterium are employed, as deuterium exchange. Different physicochemical techniques are in general used to follow the distribution of the two isotopes in deuterium versus tritium exchange. The rates of exchange of other acidic protons (—OH, —NH, and —SH) are so rapid that they cannot be followed in these techniques and all subsequent discussion refers exclusively to peptide amide proton exchange.

Tritium Exchange Techniques

Tritium exchange techniques (where the amount of the isotope is determined by radioactivity measurements) have been extensively used for the measurement of peptide amide exchange rates within an individual protein. In these studies, purified proteins are on-exchanged by incubation in buffers containing tritiated water for varying periods of time, optionally transferred to buffers free of tritium, and the rate of off-exchange of tritium determined. By analysis of the rates of tritium on- and off-exchange, estimates of the numbers of peptide amide protons in the protein whose exchange rates fall within particular exchange rate ranges can be made. These studies do not allow a determination of the identity (location within the protein's primary amino acid sequence) of the exchanging amide hydrogens measured.

Extensions of these techniques have been used to detect the presence within proteins of peptide amides which experience allosterically-induced changes in their local chemical environment and to study pathways of protein folding (Englander et al., Meth. Enzymol. 26:406-413, 1972; Englander et al., J. Biol. Chem. 248:4852-4861,1973; Englander, Biochemistry 26:1846-1850, 1987; Louie et al., J. Mol. Biol. 201:765-772, 1988). For these studies, tritium on-exchanged proteins are often allowed to off-exchange after they have experienced either an allosteric change, or have undergone time-dependent folding upon themselves, and the number of peptide amide hydrogens which experience a change in their exchange rate subsequent to the allosteric/folding modifications determined. Changes in exchange rate indicate that alterations of the chemical environment of particular peptide amides have occurred which are relevant to proton exchange (solvent accessibility, hydrogen bonding, etc.). Peptide amide hydrogens which undergo an induced slowing in their exchange rate are referred to as "slowed amides" and if previously on-exchanged tritium is sufficiently slowed in its off-exchange from such amides there results a "functional tritium labeling" of these amides. From these measurements, inferences are made as to the structural nature of the shape changes which occurred within the isolated protein. Again, determination of the identity of the particular peptide amides experiencing changes in their environment is not possible with these techniques.

Several investigators have described technical extensions (collectively referred to as "medium resolution tritium exchange") which allow the locations of particular slowed, tritium labeled peptide amides within the primary sequence of small proteins to be localized to a particular proteolytic fragment, though not to a particular amino acid.

Rosa and Richards were the first to describe and utilize medium resolution tritium techniques in their studies of the folding of ribonuclease S protein fragments (Rosa et al., J. Mol. Biol. 133:399-416, 1979; Rosa et al., J. Mol. Biol. 145:835-851, 1981; and Rosa et al., J. Mol. Biol. 160:517-530, 1982). However, the techniques described by Rosa and Richards were of marginal utility, primarily due to their failure to optimize certain critical experimental steps. No studies employing related techniques were published until the work of Englander and co-workers in which extensive modifications and optimizations of the Rosa and Richards technique were first described.

Englander's investigations utilizing tritium exchange have focused exclusively on the study of allosteric changes which take place in tetrameric hemoglobin (a subunit and b subunit 16 kD in size each) upon deoxygenation (Englander et al., Biophys. J. 10:577, 1979; Rogero et al., Meth. Enzymol. 131:508-517,1986; Ray et al., Biochemistry 25:3000-3007,1986; and Louie et al., J. Mol. Biol. 201:755-764, 1988). In the Englander procedure, native hemoglobin in the oxygenated state is on-exchanged in tritiated water. The hemoglobin is then deoxygenated (inducing allosteric change), transferred to tritium-free buffers by gel permeation column chromatography, and then allowed to off-exchange for 10-50 times the on-exchange time. On-exchanged tritium present on peptide amides which experience no change in exchange rate subsequent to the induced allosteric change in hemoglobin structure off-exchanges at rates identical to its on-exchange rates, and therefore is almost totally removed from the protein after the long off-exchange period. However, peptide amides which experience slowing of their exchange rate subsequent to the induced allosteric changes preferentially retain the tritium label during the period of off-exchange.

To localize (in terms of hemoglobin's primary sequence) the slowed amides bearing the residual tritium label, Englander then proteolytically fragments the off-exchanged hemoglobin with the protease pepsin, separates, isolates and identifies the various peptide fragments by reverse phase high pressure liquid chromatography (RP-HPLC), and determines which fragments bear the residual tritium label by scintillation counting. However, as the fragmentation of hemoglobin proceeds, each fragment's secondary and tertiary structure is lost and the unfolded peptide amide hydrogens become freely accessible to $H_2O$ in the buffer. At physiologic pH (>6), any amide-bound tritium label would leave the unfolded fragments within seconds. Englander therefore performs the fragmentation and HPLC peptide isolation procedures under conditions which minimize peptide amide proton exchange, including cold temperature (4° C.) and use of phosphate buffers at pH 2.7. This technique has been used successfully by Englander to coarsely identify and localize the peptide regions of hemoglobin α and β chains which participate in deoxygenation-induced allosteric changes. The ability of the Englander technique to localize tritium labeled amides, while an important advance, remains low; at best, Englander reports that his technique localizes amide tritium label to hemoglobin peptides 14 amino acids or greater in size, without the ability to further sublocalize the label. Moreover, in Englander's work, there is no appreciation that a suitably adapted exchange technique might be used to identify the peptide amides which reside in the contacting surface of a protein receptor and its binding partner. Instead, these Englander disclosures are concerned with the mapping of allosteric changes in hemoglobin.

Unfortunately, acid proteases are very nonspecific in their sites of cleavage, leading to considerable HPLC separation difficulties. Englander tried to work around these problems, for the localization of hemoglobin peptides experiencing allosteric changes, by taking advantage of the fact that some peptide bonds are somewhat more sensitive to pepsin than others. Even then, the fragments were "difficult to separate cleanly". They were also, of course, longer (on average), and therefore the resolution was lower. Englander concludes, "At present the total analysis of the HX (hydrogen exchange) behavior of a given protein by these methods is an immense task. In a large sense, the best strategies for undertaking such a task remain to be formulated. Also, these efforts would benefit from further technical improvements, for example in HPLC separation capability and perhaps especially in the development of additional acid proteases with properties adapted to the needs of these experiments" (Englander et al., *Anal. Biochem.* 147:234-244, 1985).

Over the succeeding years since this observation was made, no advances have been disclosed which address these critical limitations of the medium resolution hydrogen exchange technique. Most acid-reactive proteases are in general no more specific in their cleavage patterns than pepsin. Efforts to improve the technology by employing other acid reactive proteases other than pepsin have not significantly improved the technique.

Allewell and co-workers have disclosed studies utilizing the Englander techniques to localize induced allosteric changes in the enzyme *Escherichia coli* aspartate transcarbamylase (Burz et al., *Biophys. J.* 49:70-72, 1986; Mallikarachchi et al., *Biochemistry* 28:5386-5391, 1989). Burz et al. is a brief disclosure in which the isolated R2 subunit of this enzyme is on-exchanged in tritiated buffer of specific activity 100 mCi/ml, allosteric change induced by the addition of ATP, and then the conformationally altered subunit off-exchanged. The enzyme R2 subunit was then proteolytically cleaved with pepsin and analyzed for the amount of label present in certain fragments. Analysis employed techniques which rigidly adhered to the recommendations of Englander, utilizing a single RP-HPLC separation in a pH 2.8 buffer.

ATP binding to the enzyme was shown to alter the rate of exchange of hydrogens within several relatively large peptide fragments of the R2 subunit. In a subsequent more complete disclosure (Mallikarachchi, supra), the Allewell group discloses studies of the allosteric changes induced in the R2 subunit by both ATP and CTP. They disclose on-exchange of the R2 subunit in tritiated water-containing buffer of specific activity 22-45 mCi/ml, addition of ATP or CTP followed by off-exchange of the tritium in normal water-containing buffer. The analysis comprised digestion of the complex with pepsin, and separation of the peptide fragments by reverse phase HPLC in a pH 2.8 or pH 2.7 buffer, all of which rigidly adheres to the teachings of Englander. Peptides were identified by amino acid composition or by N-terminal analysis, and the radioactivity of each fragment was determined by scintillation counting. In both of these studies the localization of tritium label was limited to peptides which averaged 10-15 amino acids in size, without higher resolution being attempted.

Beasty et al., (*Biochemistry* 24:3547-3553,1985) have disclosed studies employing tritium exchange techniques to study folding of the a subunit of E. coli tryptophan synthetase. The authors employed tritiated water of specific activity 20 mCi/ml, and fragmented the tritium labeled enzyme protein with trypsin at a pH 5.5, conditions under which the protein and the large fragments generated retained sufficient folded structure to protect amide hydrogens from off-exchange during proteolysis and HPLC analysis. Under these conditions, the authors were able to produce only 3 protein fragments, the smallest being 70 amino acids in size. The authors made no further attempt to sublocalize the label by further digestion and/or HPLC analysis. Indeed, under the experimental conditions they employed (they performed all steps at 12° C. instead of 4° C., and performed proteolysis at pH 5.5 instead of pH in the range of 2-3), it would have been impossible to further sublocalize the labeled amides by tritium exchange, as label would have been immediately lost (off-exchanged) by the unfolding of subsequently generated proteolytic fragments at pH 5.5 if they were less than 10-30 amino acids in size. Additional references disclosing tritium exchange methods include Fromageot et al., U.S. Pat. No. 3,828,102, which discloses using hydrogen exchange to tritium label a protein and its binding partner, and Benson, U.S. Pat. Nos. 3,560,158 and 3,623,840, which discloses using hydrogen exchange to tritiate compounds for analytical purposes.

Deuterium Exchange Techniques

Fesik et al. (*Biochem. Biophys. Res. Commun.* 147:892-898,1987) disclose measuring by NMR the hydrogen (deuterium) exchange of a peptide before and after it is bound to a protein. From this data, the interactions of various hydrogens in the peptide with the binding site of the protein are analyzed.

Paterson et al. (*Science* 249:755-759, 1990) and Mayne et al. (*Biochemistry* 31:10678-10685,1992) disclose NMR mapping of an antibody binding site on a protein (cytochrome-C) using deuterium exchange. This relatively small protein, with a solved NMR structure, is first complexed to anti-cytochrome-C monoclonal antibody, and the preformed complex then incubated in deuterated water-containing buffers and NMR spectra obtained at several time intervals. The NMR spectrum of the antigen-antibody complex is examined for the peptide amides which experience slowed hydrogen exchange with solvent deuterium as compared to their rate of exchange in uncomplexed native cytochrome-C. Benjamin et al. (*Biochemistry* 31:9539-0545,1992) employ an identical NMR-deuterium technique to study the interaction of hen egg lysozyme (HEL) with HEL-specific monoclonal antibodies. While both this NMR-deuterium technique, and medium resolution tritium exchange rely on the phenomenon of proton exchange at peptide amides, they utilize radically different methodologies to measure and localize the exchanging amide hydrogens. Furthermore, study of proteins by the NMR technique is not possible unless the protein is small (generally less than 30 kD), large amounts of the protein are available for the study, and computationally intensive resonance assignment work is completed.

Subsequently, others have disclosed techniques in which exchange-deuterated proteins are incubated with binding partner, off-exchanged, the complex fragmented with pepsin, and deuterium-bearing peptides identified by single stage fast atom bombardment (Fab) or electrospray mass spectroscopy (MS) (Thevenon-Emeric et al., *Anal. Chem.* 64:2456-2358,1992; Winger et al., *J. Am. Chem. Soc.* 114: 5897-5989, 1992; Zhang et al., *Prot. Sci.* 2:522-531, 1993; Katta et al., *J. Am. Chem. Soc.* 115:6317-6321, 1993; and Chi et al., *Org. Mass Spectrometry* 7:58-62,1993; Engen and Smith, *Anal. Chem.* 73:256A-265A, 2001; Englander et al., *Protein Sci.* 6: 1101-1109, 1997; Dharmasiri and Smith, *Anal. Chem.* 68:2340-2344, 1996; Smith et al., *J. Mass Spectrometry* 32:135-146, 1997; Deng and Smith, *Biochemistry* 37:6256-6262, 1998). In these studies, only the enzyme pepsin is employed to effect enzymatic fragmentation under slowed exchange conditions, and no attempt made to increase the number and quantity of useful fragments produced and studied beyond employing the methods disclosed by Englander and colleagues some decades prior. The resolution of the deuterium-exchange mass spectrometry work disclosed in these publications therefore remained at the 10-14 amino acid level, with the primary limitation of their art being the ability to generate only a small number of peptides with the endopeptidase pepsin, as they employed it. See FIG. 3 for an overview of this method of exchanged deuterium localization.

U.S. Pat. Nos. 5,658,739; 6,291,189; and 6,331,400 issued to Woods, Jr. (each of which is hereby incorporated by reference herein in its entirety), disclose improved methods of determining polypeptide structure and binding sites utilizing hydrogen-exchange-labeled peptide amides, importantly including a method of increasing the resolution of the technique to the 1-5 amino acid level. This increased ability to more precisely localize exchanged amide hydrogens was afforded by the novel use of acid-resistant carboxypeptidases to effect a subsequent progressive sub-fragmentation of the small number of relatively large-sized pepsin-generated peptides initially produced in the method (see FIG. 4 for an overview of the progressive proteolysis method). In these prior methods, finer localization of the labels is achieved by analysis of subfragments generated by controlled, stepwise, sub-degradation ("progressive degradation") of each pepsin-generated, labeled peptide under slowed exchange conditions. According to these prior methods, the protein or a peptide fragment is said to be "progressively", "stepwise" or "sequentially" degraded if a series of fragments are obtained which are similar to those which would be achieved with an ideal exopeptidase. Carboxypeptidase-P, carboxypeptidase Y, and several other acid-reactive (i.e., enzymatically active under acid conditions) carboxypeptidases are specified for use in said progressive degradation of peptides under acidic conditions. To date, no aminopeptidases have been reported that are acid resistant; as a practicality, the only exopeptidases known or likely to be useful for this method are therefore carboxypeptidases.

By performing such measurement of the exchange rates of peptide amide hydrogens within a protein, one can determine its stability at the individual amino acid level. Ranking and comparison of the exchange rates of a protein's amide hydrogens therefore allows direct identification and localization of structured versus unstructured regions of the protein. Despite the utility of such exchange data, the methods used to obtain it have remained labor intensive and time consuming, with substantial limitations in throughput, comprehensiveness and resolution.

High-resolution structures are required for a fundamental understanding of protein structure and function. It is widely anticipated that access to these important structures will be facilitated by novel high-throughput protein structure determination approaches and improvements to conventional crystallographic methods. Proteomic-scale crystallography is one avenue being vigorously pursued by several groups, involving large-scale global efforts (see, e.g., Stevens and Wilson, *Science* 293:519-520, 2001; and Stevens et al., *Science* 294:89-92, 2001).

Despite the availability of many enhancements that facilitate such efforts, high-throughput production of stable protein constructs that suitably crystallize continues to be a serious bottleneck. While definition of successful constructs for protein production has long been a problem for conventional crystallography, the inadequacies of current approaches are particularly acute and costly for structural genomics efforts that presently show only a 10-20% success rate in target crystallization. Bacterial genomes are currently the focus of many of the structural genomics efforts. However, a switch to higher eukaryotes, such as mouse and human, will entail even lower success rates, due in part to more complex and higher molecular weight proteins.

Thus, there remains a need in the art for improved simple, robust, quick and efficient methods whereby the structure of a protein of interest can be analyzed to efficiently define protein domain boundaries, the location of unstructured or floppy regions between or within domains, as well as disordered regions within single-domain proteins; and then modified in order to refine and optimize the processes of crystallization and crystallographic structure determination in a high-throughput manner.

SUMMARY OF THE INVENTION

The present invention provides methods for crystallographic structure determination of a protein of interest through the use of hydrogen exchange analysis. Preferred methods of the present invention employ novel high resolution hydrogen exchange analysis. In some embodiments of the invention, methods of hydrogen exchange analysis comprise fragmentation of a labeled protein using methods described in U.S. Pat. Nos. 5,658,739; 6,331,400, and 6,291,189, the entire disclosures of which are incorporated herein by reference. In other embodiments of the invention, the hydrogen exchange analysis allows for high-throughput structural determinations due to simplifications of the protein fragmentation methods described in U.S. Pat. Nos. 5,658,739; 6,331,400, and 6,291,189.

According to a first aspect of the present invention, there are provided methods for crystallographic structure determination. Such methods comprise subjecting to crystallization and structure determination one or more modified form(s) of the protein of interest obtained by identifying and deleting unstructured regions of the protein using hydrogen exchange analysis.

In one embodiment, such methods comprise subjecting to crystallization and structure determination one or more modified forms(s) of said protein generated by deleting at least one unstructured region of said protein, wherein said at least one unstructured region is identified by hydrogen exchange analysis. Identifying unstructured regions in the protein by hydrogen exchange analysis preferably comprises the steps of (a) generating a hydrogen exchange stability map of said protein by hydrogen exchange analysis, and (b) identifying unstructured regions of said protein.

The hydrogen exchange analysis comprises determining the quantity of isotopic hydrogen and/or the rate of exchange of hydrogen at a plurality of peptide amide hydrogens exchanged for isotopic hydrogen in a protein labeled with a hydrogen isotope other than $^1H$, such as deuterium or tritium.

In one preferred embodiment, hereinafter referred to as "progressive proteolysis" (as defined in U.S. Pat. No. 6,291,189, column 7, line 58 through column 8, line 33) the process of determining the quantity of isotopic hydrogen and/or the rate of exchange comprises: (a) fragmenting the labeled protein into a plurality of fragments under slowed hydrogen exchange conditions; (b) identifying which fragments of the plurality of fragments are labeled with isotopic hydrogen; (c) progressively degrading each fragment of the plurality of fragments to obtain a series of subfragments, wherein each subfragment of the series is composed of about 1-5 fewer amino acid residues than the preceding subfragment in the series from one end but with preservation of the other end of the subfragment series; (d) measuring an amount of isotopic hydrogen associated with each subfragment; and (e) correlating said amount of isotopic hydrogen associated with each subfragment with an amino acid sequence of the fragment from which said subfragment was generated, thereby determining the quantity of isotopic hydrogen and/or the rate of exchange of a plurality of peptide amide hydrogens exchanged for isotopic hydrogen in a protein labeled with a hydrogen isotope other than $^1H$.

In one aspect of the invention, the step of progressively degrading comprises contacting the fragments with an acid resistant carboxypeptidase, for example, carboxypeptidase P, carboxypeptidase Y, carboxypeptidase W, carboxypeptidase C, or combinations of any two or more thereof.

In another preferred embodiment of the invention, hereinafter referred to as the "improved proteolysis" method, the process of determining the quantity of isotopic hydrogen and/or the rate of exchange comprises: (a) generating a population of sequence overlapping fragments of said labeled protein by treatment with at least one endopeptidase or combination of endopeptidases under conditions of slowed hydrogen exchange, and then (b) deconvoluting fragmentation data acquired from said population of sequence-overlapping endopeptidase-generated fragments. This improved method dramatically speeds and modulates the sites and patterns of proteolysis by endopeptidases so as to produce highly varied and highly efficient fragmentation of the labeled protein in a single step, thereby avoiding the use of carboxypeptidases completely.

In one aspect, endopeptidase fragments are generated by cleaving said protein with at least one endopeptidase selected from the group consisting of a serine endopeptidase, a cysteine endopeptidase, an aspartic endopeptidase, a metalloendopeptidase, and a threonine endopeptidase. In a preferred method, endopeptidase fragments are generated by cleaving said protein with pepsin. Alternatively, endopeptidase fragments may be generated by cleaving said protein with newlase or *Aspergillus* protease XIII, or by more than one endopeptidase used in combination.

In preferred embodiments, invention methods measure the mass of peptide fragments, for example, utilizing mass spectrometry, to determine the presence or absence and/or quantity of an isotope of hydrogen on an endopeptidase fragment. Fragmentation data is deconvoluted by comparing the quantity and rate of exchange of isotope(s) on a plurality of sequence-overlapping endopeptidase-generated fragments with the quantity and rate of exchange of isotope(s) on at least one other endopeptidase fragment, wherein said quantities are corrected for back-exchange in an amino acid sequence-specific manner.

According to another aspect of the present invention, there are provided methods for crystallographic structure determination of a protein comprising: (a) generating one or more modified forms of said protein by deleting at least one unstructured region of said protein identified by hydrogen exchange analysis; and (b) subjecting to crystallization and structure determination said one or more modified forms of said protein.

According to another aspect of the present invention, there are provided methods for crystallographic structure determination of a protein comprising: (a) identifying unstructured regions in the said protein by hydrogen exchange analysis: (b) generating one or more modified forms of said protein by deleting at least one of said unstructured regions of said protein; and (c) subjecting to crystallization and structure determination said one or more modified forms of said protein.

According to another aspect of the present invention, there are provided methods for crystallographic structure determination of a protein comprising: (a) selecting a protein that is resistant to crystallization, or that forms crystals that do not diffract X-rays sufficient for structure determination; (b) identifying unstructured regions in said protein by hydrogen exchange analysis; (c) generating one or more modified forms of said protein by deleting at least one of said unstructured regions of said protein; and (d) subjecting to crystallization and structure determination said one or more modified forms of said protein.

According to another aspect of the present invention, there are provided methods of refining a crystallographic structure determination of a protein of interest. Such methods comprise comparing an initial crystallographic structure determined using crystal(s) of the protein to at least one other crystallographic structure determined using crystal(s) of at least one modified form of the protein. The modified form(s) of said protein is(are) obtained by generating a hydrogen exchange stability map of the native protein and identifying unstructured regions of the protein and boundaries between structured and unstructured regions of the protein using hydrogen exchange analysis. At least one unstructured region thus identified, or a portion thereof is then deleted to prepare modified forms of the protein.

According to another aspect of the present invention, there are provided methods of crystallization of a protein of interest. Such methods comprise comparing an initial hydrogen exchange stability map of the protein to at least one other hydrogen exchange stability map of at least one modified form of the protein. One or more modified form(s) of the protein that exhibit an improved hydrogen exchange stability map are then subjected to crystallization. According to a further aspect of the present invention, there are provided methods of crystallographic structure determination of a protein of interest, comprising comparing an initial hydrogen exchange stability map of the protein to at least one other hydrogen exchange stability map of at least one modified form of the protein. Modified form(s) of the protein that exhibit an improved hydrogen exchange stability map are then subjected to crystallization and structure determination.

According to another aspect of the present invention, there are provided methods of characterizing conformational differences between a protein in a solution and the same protein in crystal form, comprising comparing a characterization of said protein in solution to a characterization of said protein in crystal form. The characterization of the protein in solution is obtained by hydrogen exchange analysis. The characterization of the protein in crystal form is obtained by hydrogen exchange analysis after incubating the protein in crystal form in a microcrystalline suspension in deuterated water, under conditions where dissolution of the protein in crystal form is inhibited.

BRIEF DESCRIPTION OF THE FIGURES

FIG. 12 illustrates the fragmentation map of RIIβ (SEQ ID NO: 5).

FIG. 14A shows percent deuteration for residues 2-19 (SEQ ID NO: 6). The top bar for each ligand state represents t=10 s and the bottom bar represents t=3000 s. Secondary structure assignments are labeled above the sequence. FIG. 14B plots the number of deuterons incorporated as a function of time for residues 15-19 in cAMP-free (●), cAMP-bound (■), and C-subunit bound (▲) conformations of RIIβ.

FIG. 5A shows percent deuteration for residues 28-130 (SEQ ID NO: 7). The top bar for each ligand state represents t=1 0 s and the bottom bar represents t=3000 s. Secondary structure assignments are labeled above the sequence. FIG. 15 plots the number of deuterons incorporated as a function of time for residues 102-115 in cAMP-free (●), cAMP-bound (■), and C-subunit bound (▲) conformations of RIIβ.

FIG. 16A is a ribbon diagram of cAMP-binding domains highlighting residues 222-224 (cA:αP), 228-233 (cA:PBC), 341-353 (cB:β6/αP), and 354-363 (cB:PBC) (SEQ ID NOs: 8 and 9). FIG. 16B shows percent deuteration for residues of cAMP-binding pockets. The top bar for each ligand state represents t=10 s and the bottom bar represents t=3000 s. Secondary structure assignments are labeled above the sequence. FIG. 16C plots the number of deuterons incorporated as a function of time for sample residues 228-233 in cAMP-free (●), cAMP-bound (■), and C-subunit bound (▲) conformations of RIIβ. This plot is representative of all 4 peptides.

FIG. 17A is a ribbon diagram of the cB domain highlighting residues 303-312 (cB:β3) 321-325 (cB:β4), 377-379 (cB:αB) 390-396 (cB:αC), and 399-401 (cB:αC). FIG. 17B shows percent deuteration for each ligand state at t=10 s (top bar) and t=3000 s (bottom bar) (SF0 ID NOs: 10-12. respectively in order of appearance). Secondary structure assignments are labeled above the sequence. FIG. 17C plots the number of deuterons incorporated as a function of time in cAMP-free (●), cAMP-bound (■), and C-subunit bound (▲) conformations of RIIβ for residues 390-396 and 399-401. The plot for residues 390-396 is representative of the remaining 3 peptides.

FIG. 18A is a ribbon diagram of cAMP-binding domains highlighting residues 150-152 (αX$_n$'), 253-268 (cA:αC,αC'), 271-277 (cA:αc "), 278-281 (cB:αA), and 381-387 (cB:αB/αC). FIG. 18B shows percent deuteration for each ligand state at t=10 s (top bar) and t=3000 s (bottom bar) (SEQ ID NOs: 13-15, respectively in order of appearance). Secondary structure assignments are labeled above the sequence. FIG. 18C plots the number of deuterons incorporated as a function of time for cAMP-free (●), cAMP-bound (■), and C-subunit bound (▲) conformations of RIIβ.

FIG. 19 collectively illustrates the exchange maps of the Thermotoga maritima proteins studies herein. Percentages indicate the amount of rapid exchange in amino acid segments of four or more residues, as a percentage of the entire sequence.

DETAILED DESCRIPTION OF THE INVENTION

Figure 1:
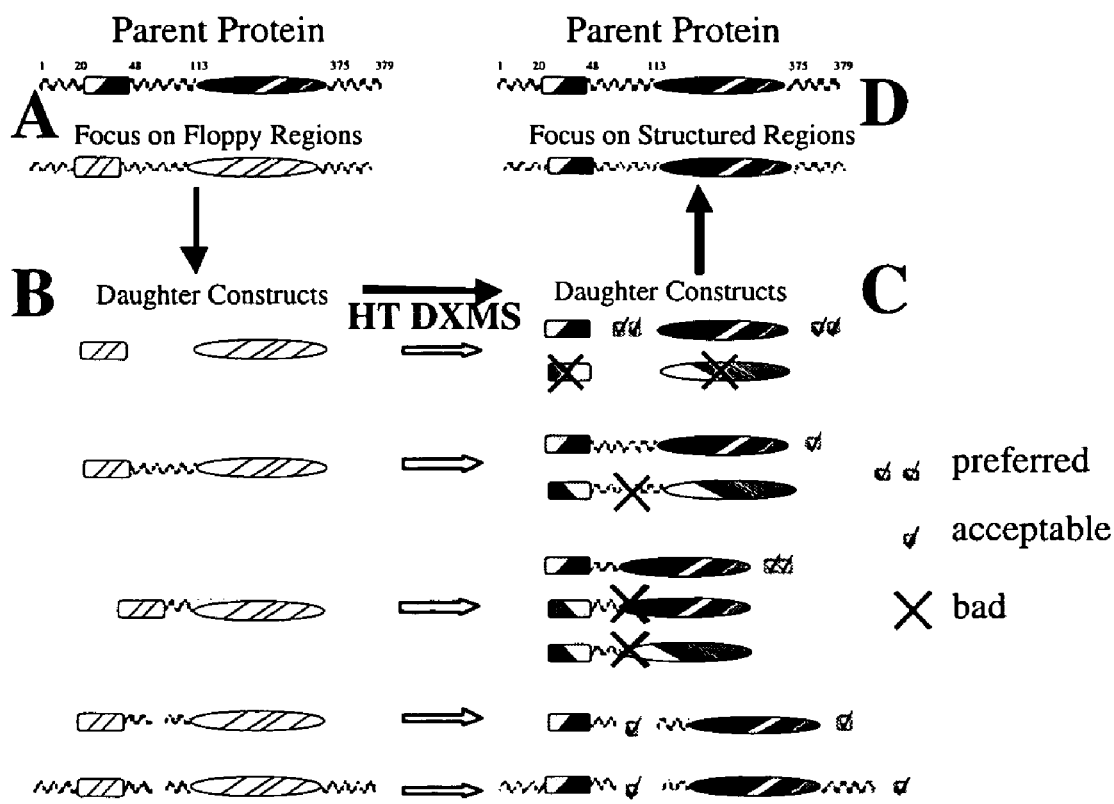
FIG. 1 shows the use of sequential hydrogen exchange analyses to examine multiple mutations (daughter constructs) of the original protein (parent). In Step A, amide hydrogen exchange data is acquired on the parent protein (in this example, the cAPK RIα protein) to determine a stability map (shaded in gray-scale). In Step B, a variety of daughter constructs are created based on the interpretation of the parent stability map, selectively depleted of unstructured regions. Small quantities of each of these daughter proteins is then produced and purified, and each is subjected to hydrogen exchange analysis to determine the stability map of each daughter construct (Step C). The stability map of each daughter construct is then compared to the stability map of the parent (Step D) to identify daughter proteins that have preserved the conformational structures of the retained regions of the parent protein. These "faithful" daughter proteins are then subjected to high-throughput crystallization and structure determination.

In a first aspect, the present invention provides methods for crystallographic structure determination of a protein of interest, said method comprising subjecting to crystallization and structure determination one or more modified form(s) of said protein obtained by deleting unstructured regions of said protein, wherein said unstructured regions are identified by hydrogen exchange analysis.

As used herein, the phrase "crystallographic structure determination" refers to any method of obtaining the three-dimensional structure or model of a protein of interest through the use of protein crystallography. Methods of crystallographic structure determination, in particular X-ray diffraction crystallographic methods, are well known in the art, and frequently are provided at large shared facilities once crystals are obtained. The methods of the present invention provide a novel method of performing crystallographic structure determination through the use of hydrogen exchange analysis. Hydrogen exchange analysis can be integrated into any known or novel methods of crystallography available in the art.

Many proteins which appear well-structured overall, contain unstructured regions (see, e.g., Wright and Dyson, *J. Mol. Biol*. 293:321-331,1999). While such regions may serve a function within the protein in some context, they can inhibit or prevent crystallization of the well-folded regions. This problem has been apparent for years, but its full extent is difficult to discern from the published literature. In some instances, proteins may crystallize with some floppy regions, either at their ends or within short internal stretches. In many other instances, it is not known why a particular protein does not crystallize, even with seemingly pure protein. Using the methods of the present invention, crystallographic structure determination is facilitated by the ability to rapidly and precisely define structured and unstructured regions of a target that could then be used to produce expression constructs and proteins containing structured domains in their native conformation, but otherwise depleted of the unstructured regions (e.g., "disorder-depleted" proteins).

This capability to define structured and unstructured region of a protein of interest can enhance crystallographic structure determination through several mechanisms. It can increase the homogeneity of protein preparations. Moreover, unstructured regions of proteins are particularly susceptible to inadvertent degradation by contaminating cellular proteases in the course of purification and storage. The energetics and kinetics of protein crystallization are facilitated by selective deletion of unstructured sequences (see, e.g., Kwong et al., *J. Biol. Chem*. 274:4115-4123,1999). Smaller constructs should result in better diffracting crystals in a significant percent of the cases (see, e.g., Cohen et al., *Prot. Sci*. 4:1088-1099,1995), that consequently can result in higher resolution data more amenable to automated map fitting procedures (see, e.g., Lamzin and Perrakis, *Nature Str. Biol*. Nov. 7, 2000 Suppl.:978-981, 2000).

A number of approaches to obtain information defining structured and unstructured protein regions, ranging from stability-dependent protein expression screens, to computation of stability from primary structure have been reported and used, but each has requirements that limit utility (see, e.g., Dunker et al, *Pac. Symp. Biocomp*. 3:473484, 1998; Garner et, al., *Genome Inform*. 9:201-214,1998; and Romero et al., *Pac. Symp. Biocomp*. 3:473-484, 1998). With NMR spectroscopy, protein quantity, concentration, time needed, and size are limiting. Limited proteolysis coupled to mass spectrometry is presently one of the preferred approaches to refining construct definition for conventional crystallographic efforts (see, e.g. Cohen et al., supra). As such, its use is time consuming, frequently requiring that multiple proteolytic reactions be refined for optimal cleavage. The interpretation of the results of limited proteolysis is confounded by the possibility that proteolysis may clip internal loops, leading to destabilization and subsequent further proteolytic degradation of what was actually a structured region.

It is often known in advance that a particular protein is likely made up of several domains that are connected by flexible linkers. Examples of this are DNA binding proteins such as the lambda repressor C-terminal (Bell and Lewis, *J. Mol. Biol*. 314:1127-1136, 2001) and the TRHF dimerization domain of the human telomeric protein (Fairall et al, *Mol. Cell*. 8:351-361, 2001). Unfortunately, the experimental definition of domain boundaries, even when they are anticipated, is often problematic, as it was for these proteins, and is usually addressed through trial and error, by making many expression constructs and protein preparations and testing the outcome to determine quantity and quality of expression, solubility, crystallization and structure determination.

Finally, there is no facile method to confirm that the expression constructs and proteins designed on the basis of any of these approaches have faithfully retained the stable or structured elements of the original parent protein. When "disorder-depleted" modified forms of the parent are produced, uncertainty remains concerning the degree to which they recapitulate the structure of stable portions of the parent. Taken together, these several shortcomings have rendered the foregoing methods of designing modified forms of a protein of interest of little utility in the context of large-scale crystal structure determination efforts, where throughput and cost are dominating considerations (see, e.g., Chen et al., *Prot. Sci*. 7:2623-2630, 1998).

The methods of the present invention allow for the measurement of peptide amide hydrogen exchange rates that can provide precisely the information needed for reliable expression construct design. The methods of the present invention comprise generating a hydrogen exchange stability map. The hydrogen exchange stability map shows unstructured regions of the protein and precisely shows the location of boundaries between structured and unstructured regions of the protein. This information provides the guide for preparation of modified forms of the protein wherein all or part of at least one unstructured region of the protein is removed. The modified protein, wherein all or part of at least one unstructured region of the protein is removed, is then subjected to a crystallization procedure. Unstructured regions of a protein structure are known to inhibit the formation of crystals, and to inhibit the formation of crystals suitable for crystal structure determination. Daughter construct proteins, modified to remove all or part of at least one specific regions identified by hydrogen exchange analysis as unstructured, are expected to demonstrate improved crystallization characteristics.

Methods of the invention are also provided, wherein a hydrogen exchange stability map of a daughter construct, i.e., a protein modified by excising all or part of at least one unstable or unstructured region of the protein, may be compared to a hydrogen exchange stability map of the parent protein. This comparison serves to characterize the degree to which the modified protein faithfully retains the stable or structured elements of the parent protein.

As used herein, the phrase "hydrogen exchange analysis" refers to any method by which measurement of the exchange rates of a peptide amide hydrogen with an isotope of hydrogen (for example, deuterium or tritium), present in the environment surrounding the protein (whether in soluble or crystalline form), are used to gain insight to the structure or stability of a protein as a whole, or portions or regions thereof. For more than 40 years, peptide amide hydrogen-exchange techniques have been employed to study the thermodynamics of protein conformational change and to probe the mechanisms of protein folding (see, e.g., Englander and Englander, *Meth. Enzymol*. 232:2642, 1994; and Bai et al., *Meth. Enzymol*. 259:344, 1995). More recently, they have proven to be increasingly powerful methods by which protein dynamics, domain structure, regional stability and function can be studied (see, e.g., Englander et al., *Prot. Sci*. 6:1101-1109, 1997). The principle of hydrogen-exchange reflects the fact that many hydrogens (commonly known as acidic hydrogens such as —OH, —$NH_2$, —SH, and peptide amide hydrogens) are not permanently attached to the protein, but continuously and reversibly interchange with hydrogen present in their external immediate environment. Most acidic hydrogen exchanges occur too rapidly to be experimentally useful. An important exception is the more slowly exchanging peptide amide hydrogen (main-chain amide hydrogen) present in every amino acid except proline, thereby providing a way of examining protein structure and stability.

By an "improved hydrogen exchange stability map" is meant that the hydrogen exchange stability map of the modified form of the protein demonstrates a reduction in the unstructured portion of the protein. An "improved hydrogen exchange stability map" is predictive that the modified form is (a) more likely to form crystals than the unmodified protein of interest, and/or (b) more likely to form crystals that are suitable for crystal structure determination than the unmodified protein of interest.

The hydrogen exchange reaction can be experimentally followed by using tritiated or deuterated solvent. The chemical mechanisms of the exchange reactions are understood, and several well-defined factors can profoundly alter exchange rates. One of these factors is the extent to which a particular exchangeable hydrogen is exposed or accessible to solvent. The exchange reaction proceeds efficiently only when a particular peptide amide hydrogen is fully exposed to solvent. In a completely unstructured polypeptide chain, all peptide amide hydrogens are maximally accessible to water and exchange at their maximal possible rate, which is approximately (within a factor of 30) the same for all amides; a half-life of exchange in the range of one second at 0° C. and pH 7.0. Exact exchange rates expected for particular amide hydrogens in fully unstructured segments can be reliably calculated from knowledge of the temperature, pH and the primary amino acid sequence involved (see, e.g., Molday et al., *Biochemistry* 11:150, 1972; and Bai et al., *Proteins: Str. Funct. Gen*. 17:74-86, 1993).

In a folded protein, most peptide amide hydrogens are slower (up to $10^9$ fold slower) than this maximal exchange rate, as they are not efficiently exposed to solvent. The ratio of exchange rates for a particular amide hydrogen, before and after protein folding, is referred to as the exchange protection factor, and directly reflects the free energy change in the atomic environment of that particular hydrogen upon folding. In this sense, amide hydrogens can be treated as atomic scale sensors of highly localized free energy change throughout a protein and the magnitude of free energy change reported from each of a protein's amide hydrogens in a folded versus unfolded state is precisely equal to $-RT \ln$ (protection factor) (Bai et al., supra). In effect, each peptide amide hydrogen's exchange rate in a folded protein directly and precisely reports the protein's thermodynamic stability at the individual amino acid scale. Ranking and comparison of the exchange rates of a protein's amide hydrogens therefore allows direct and unambiguous identification and localization of structured and unstructured regions of the protein. As used herein, unstructured regions of a protein are those where contiguous stretches of primary sequence exhibit fast exchange rates, indicative of complete and continuous solvation of the amide hydrogens in such segments. Further, as used herein, very unstructured regions refer to linear stretches of primary sequence in which the rates of exchange of each amide hydrogen in the segment is very fast, typically greater than about 90% of amide hydrogens are saturation-deuterated in about 10 seconds or less at 0° C. At least one unstructured region, or a portion thereof, is then targeted for deletion in accordance with the methods of the present invention.

Deuterium exchange methodologies coupled with liquid chromatography mass spectrometry (LCMS), developed over the past 10 years, presently provide the most effective approach to study proteins larger than 30 kDa in size (see, e.g., Engen and Smith, *Anal. Chem.* 73:256-65, 2001). Proteolytic and/or collision-induced dissociation (CID) fragmentation methods allow exchange behavior to be mapped to subregions of the protein (Engen and Smith, supra; Hoofnagle et al., *Proc. Natl. Acad. Sci. USA* 98:956-961, 2001; Resing et al., *L. Am. Soc. Mass Spectrom.* 10:685-702, 1999; and Mandel et al., *Anal. Chem.* 70:3987-3995, 1998).

In order to proceed with crystallizing a protein of interest, a substantially pure protein preparation is first made. The following terms are defined in order to facilitate the discussion of protein preparation, modification, and crystallization.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

"Unnatural amino acid" and "unnatural R-group" includes amino acids that are not naturally found in proteins. Examples of unnatural amino acids included herein are racemic mixtures of selenocysteine and selenomethionine. In addition, unnatural amino acids include the D or L forms of, for example, nor-leucine, para-nitrophenylalanine, homophenylalanine, para-fluorophenylalanine, 3-amino-2-benzylpropionic acid, homoarginines, D-phenylalanine, and the like.

"R-group" refers to the substituent attached to the α-carbon of an amino acid residue. An R-group is an important determinant of the overall chemical character of an amino acid. There are nineteen natural R-groups found in proteins, which make up the twenty naturally occurring amino acids.

One of the twenty naturally occurring amino acids, glycine, is alpha unsubstituted and achiral. "α-carbon" refers to the chiral carbon atom found in an amino acid residue. Typically, four different substituents will be covalently bound to said α-carbon including an amine group, a carboxylic acid group, a hydrogen atom, and an R-group.

"Positively charged amino acid" and "positively charged R-group" includes any naturally occurring or unnatural amino acid having a positively charged side chain under normal physiological conditions. Examples of positively charged, naturally occurring amino acids include arginine, lysine, histidine, and the like.

"Negatively charged amino acid" and "negatively charged R-group" includes any naturally occurring or unnatural amino acid having a negatively charged side chain under normal physiological conditions. Examples of negatively charged, naturally occurring amino acids include aspartic acid, glutamic acid, and the like.

"Hydrophobic amino acid" and "hydrophobic R-group" includes any naturally occurring or unnatural amino acid having an uncharged, nonpolar side chain that is relatively insoluble in water. Examples of naturally occurring hydrophobic amino acids are alanine, leucine, isoleucine, valine, proline, phenylalanine, tryptophan, methionine, and the like.

"Hydrophilic amino acid" and "hydrophilic R-group" includes any naturally occurring or unnatural amino acid having a charged polar side chain that is relatively soluble in water. Examples of naturally occurring hydrophilic amino acids include serine, threonine, tyrosine, asparagine, glutamine, cysteine, and the like.

Modified forms of a protein of interest include forms having one or more R-group modifications to the amino acids of the parent protein or having a substitution of one or more amino acids, either conservative or non-conservative substitutions, that result in a modification of the protein amino acid sequence. For example, a modified form of a protein will have an R-group on one or more α-carbon other than the prescribed arrangements of R-groups associated with one or more α-carbon of the parent protein. As used herein. A "conservative substitution" is an amino acid change that does not affect the three dimensional structure of the protein, as is known in the art, for example, substitution of a polar for a polar residue, a non-polar for a non-polar residue, etc.

Modifications and substitutions are not limited to replacement of amino acids. As used herein, "mutant", "mutated", "modified" or "daughter" forms of the protein of interest also include for example, deletion(s), replacement(s) or addition(s) of portions of the parent protein. For a variety of purposes, such as increased stability, solubility, or configuration concerns, one skilled in the art will recognize the need to introduce these and other such modifications. Examples of such other modifications include incorporation of rare amino acids, dextra-amino acids, glycosylation sites, cytosine for specific disulfide bridge formation, and the like. The modified peptides can be chemically synthesized, or the isolated gene can be subjected to site-directed mutagenesis, or a synthetic gene can be synthesized and expressed in bacteria, yeast, baculovirus, tissue culture, and so on.

Modified forms of the proteins contemplated for use in the practice of the present invention may be prepared in a number of ways available to the skilled artisan. For example, the gene encoding a parent protein may be mutated or modified at those sites identified by the hydrogen exchange methods described herein as corresponding to amino acid residues in unstructured areas by means currently available to the artisan skilled in molecular biological techniques. Such techniques include oligonucleotide-directed mutagenesis, deletion, chemical mutagenesis, and the like. The protein encoded by the mutant gene is then produced by expressing the gene in, for example, a bacterial, mammalian, insect or plant expression system.

Alternatively, modified forms may be generated by site specific-replacement of a particular amino acid with an unnaturally occurring amino acid or mimetic. As such, modified forms may be generated through replacement of an amino acid residue or a particular cysteine or methionine residue with selenocysteine or selenomethionine. This may be achieved by growing a host organism capable of expressing either the wild-type or mutant polypeptide on a growth medium depleted of natural cysteine or methionine or both and growing on medium enriched with either selenocysteine, selenomethionine, or both. These and similar techniques are described in Sambrook et al., (Molecular Cloning, A Laboratory Manual, 2$^{nd}$ Ed. (1989) Cold Spring Harbor Laboratory Press).

Another suitable method of creating modified forms of a protein for use in the methods of the present invention is based on a procedure described in Noel and Tsai, *J. Cell. Biochem.*, 40:309-320,1989. In so doing, the nucleic acids encoding the protein can be synthetically produced using oligonucleotides having overlapping regions, said oligonucleotides being degenerate at specific bases so that mutations are induced.

In designing the nucleic acid sequences to encode a protein of interest, it may be desirable to reengineer the gene for improved expression in a particular expression system. For example, it has been shown that many bacterially derived genes do not express well in plant systems. In some cases, plant-derived genes do not express well in bacteria. This phenomenon may be due to the non-optimal G+C content and/or A+T content of said gene relative to the expression system being used. For example, the very low G+C content of many bacterial genes results in the generation of sequences mimicking or duplicating plant gene control sequences that are highly A+T rich. The presence of A+T rich sequences within the genes introduced into plants (e.g., TATA box regions normally found in promoters) may result in aberrant transcription of the gene(s). In addition, the presence of other regulatory sequences residing in the transcribed mRNA (e.g. polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords mRNA stability and translation accuracy for a particular expression system.

Due to the plasticity afforded by the redundancy of the genetic code (i.e., some amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon:intron junctions, polyA addition signals, or RNA polymerase termination signals.

Genes encoding the protein of interest can be placed in an appropriate vector and can be expressed using a suitable expression system. An expression vector, as is well known in the art, typically includes elements that permit replication of said vector within the host cell and may contain one or more phenotypic markers for selection of cells containing the gene. The expression vector will typically contain sequences that control expression such as promoter sequences, ribosome binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see U.S. Pat. Nos. 4,762,785; 5,451,513 and 5,545,817, which are each incorporated herein by reference in their entirety) or other sequences that increase the ease of peptide purification, such as an affinity tag.

A wide variety of expression control sequences are useful in expressing native/parent or modified forms of the protein of interest when operably linked thereto. Such expression control sequences include, for example, the early and late promoters of SV40 for animal cells, the lac system, the trp system, major operator and promoter systems of phage S, and the control regions of coat proteins, particularly those from RNA viruses in plants. In *E. coli*, a useful transcriptional control sequence is the T7 RNA polymerase binding promoter, which can be incorporated into a pET vector as described by Studier et al., *Methods Enzymology* 185:60-89, 1990.

For expression, a desired gene should be operably linked to the expression control sequence and maintain the appropriate reading frame to permit production of the desired protein or modified form thereof. Any of a wide variety of well-known expression vectors are of use in the methods of the present invention. These include, for example, vectors comprising segments of chromosomal, non-chromosomal and synthetic DNA sequences such as those derived from SV40, bacterial plasmids including those from *E. coli* such as col E1, pCR1, pBR322 and derivatives thereof, pMB9, wider host range plasmids such as RP4, phage DNA such as phage S, NM989, M13, and other such systems as described by Sambrook et al., (Molecular Cloning, A Laboratory Manual, 2$^{nd}$ Ed. (1989) Cold Spring Harbor Laboratory Press), which is incorporated by reference herein.

A wide variety of host cells are available for expressing mutants of the present invention. Such host cells include, for example, bacteria such as *E. coli, Bacillus* and *Streptomyces*, fungi, yeast, animal cells, plant cells, insect cells, and the like.

"Purified" or "isolated" refers to a protein or nucleic acid that has been separated from its natural environment. Contaminant components of its natural environment may include enzymes, hormones, and other proteinaceous or non-proteinaceous solutes. In one embodiment, the isolated molecule, in the case of a protein, will be purified to a degree sufficient to obtain at least 15 residues of N-terminal or internal amino acid sequence or to homogeneity by SDS-PAGE under reducing or non-reducing conditions using Coomassie blue or silver stain. In the case of a nucleic acid the isolated molecule will preferably be purified to a degree sufficient to obtain a nucleic acid sequence using standard sequencing methods.

By a "substantially pure polypeptide" or "substantially pure protein" is meant a polypeptide or protein which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, polypeptide. A substantially pure protein or polypeptide may be obtained, for example, by extraction from a natural source; by expression of a recombinant nucleic acid encoding a polypeptide; or by chemically synthesizing the protein. Purity can be measured by any appropriate method (e.g., column chromatography, polyacrylamide gel electrophoresis, or by HPLC analysis).

"Degenerate variations thereof" refers to changing a gene sequence using the degenerate nature of the genetic code to encode proteins having the same amino acid sequence yet having a different gene sequence. Degenerate gene variations thereof can be made encoding the same protein due to the plasticity of the genetic code, as described herein.

"Expression" refers to transcription of a gene or nucleic acid sequence, stable accumulation of nucleic acid, and the translation of that nucleic acid to a polypeptide sequence. Expression of genes also involves transcription of the gene to make RNA, processing of RNA into mRNA in eukaryotic systems, and translation of mRNA into proteins. It is not necessary for the genes to integrate into the genome of a cell in order to achieve expression. This definition in no way limits expression to a particular system or to being confined to cells or a particular cell type and is meant to include cellular, transient, in vitro, in vivo, and viral expression systems in both prokaryotic, eukaryotic cells, and the like.

"Foreign" or "heterologous" genes refers to a gene encoding a protein whose exact amino acid sequence is not normally found in the host cell.

"Promoter" and "promoter regulatory element", and the like, refers to a nucleotide sequence element within a nucleic acid fragment or gene that controls the expression of that gene. These can also include expression control sequences. Promoter regulatory elements, and the like, from a variety of sources can be used efficiently to promote gene expression. Promoter regulatory elements are meant to include constitutive, tissue-specific, developmental-specific, inducible, subgenomic promoters, and the like. Promoter regulatory elements may also include certain enhancer elements or silencing elements that improve or regulate transcriptional efficiency. Promoter regulatory elements are recognized by RNA polymerases, promote the binding thereof, and facilitate RNA transcription.

Once a substantially pure protein of interest is prepared, it is subjected to crystallization to obtain the protein in crystalline form, of sufficient quality to determine the three-dimensional structure of the protein by X-ray diffraction methods. X-ray crystallography is a method of solving the three-dimensional structures of molecules. The structure of a molecule is calculated from X-ray diffraction patterns using a crystal of the protein studied as a diffraction grating. Three-dimensional structures of protein molecules arise from crystals grown from a concentrated solution of that protein. The process of X-ray crystallography can include the following steps:

(a) preparing and isolating a polypeptide;

(b) growing a crystal from a solution comprising the polypeptide with or without a compound, substrate, substrate mimic, modulator, ligand, or ligand analog; and (c) collecting X-ray diffraction patterns from the crystal(s), determining unit cell dimensions and symmetry, determining electron density, fitting the amino acid sequence of the polypeptide to the electron density, and refining the structure.

The term "crystalline form" refers to a crystal formed from a solution comprising a purified polypeptide corresponding to all or part of a protein of interest. In preferred embodiments, a crystalline form may also be formed from a purified polypeptide corresponding to all or part of a protein of interest in a complex with one or more additional molecules selected from the group consisting of substrates, products, substrate mimics, and inhibitors of the protein.

The present invention allows for the characterization of proteins and modified forms thereof by crystallization followed by X-ray diffraction. Polypeptide crystallization occurs in solutions where the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Compounds known as "precipitants" are often used to decrease the solubility of the polypeptide in a concentrated solution by forming an energetically unfavorable precipitating layer around the polypeptide molecules (Weber, *Adv. Prot. Chem.* 41:1-36, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2,4-pentanediol, many of the polyglycols (such as polyethylene glycol), and the like.

Commonly used polypeptide crystallization methods include the following techniques: batch, hanging drop, seed initiation, dialysis, and the like. In each of these methods, it is important to promote continued crystallization after nucleation by maintaining a supersaturated solution. In the batch method, polypeptide is mixed with precipitants to achieve supersaturation, the vessel is sealed, and set aside until crystals appear. In the dialysis method, polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, *J. Biol. Chem.* 6300-6306, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization involves introducing a nucleation site into a concentrated polypeptide solution. Generally, a concentrated polypeptide solution is prepared and a seed crystal of the polypeptide is introduced into this solution. If the concentration of the polypeptide and any precipitants are correct, the seed crystal will provide a nucleation site around which a larger crystal forms. In typical embodiments, the crystals of the present invention are formed in hanging drops with 15% PEG 8000; 200 mM magnesium acetate or magnesium chloride, 100 mM 3-(N-morpholino)-2-hydroxypropanesulfonic acid (pH 7.0), and 1 mM dithiothreitol as precipitant.

Some proteins may be recalcitrant to crystallization. However, several techniques are available to the skilled artisan. Quite often the removal of polypeptide segments at the amino or carboxy terminal end of the protein is necessary to produce crystalline protein samples. These procedures are guided in the methods of the present invention by hydrogen exchange stability maps of the protein. Said procedures involve either treatment of the protein with one of several proteases including trypsin, chymotrypsin, substilisin, and the like. This treatment often results in the removal of flexible polypeptide segments that are likely to negatively affect crystallization. Alternatively, the removal of coding sequences from the protein's gene facilitates the recombinant expression of shortened proteins that can be screened for crystallization.

In particular, unstructured regions that have been identified by hydrogen exchange analysis may be deleted from the protein of interest. Various possibilities for creating modified forms of the protein exist. Some or all such unstructured stretches of amino acid sequence at the N- or C-terminus of the protein can be deleted, or particular combinations may be selected. Optionally, internal stretches that exceed 15-20 amino acid residues in length may be deleted. In preferred embodiments, several (preferably more than 10) different deletion constructs are prepared from each parent protein of interest. Variations of modified forms may be prepared, including different amounts of the unstructured segment left behind (for example, in a 30 amino acid very fast exchanging stretch one could delete the entire 30 amino acids, leave a 5 amino acid "flexible linker", etc.). Comparative information provided by the hydrogen exchange studies of these daughter constructs allows progressive improvement in the ability to identify deletion strategies that result in constructs, and in turn proteins, that retain the hydrogen exchange profile, herein referred to as the "hydrogen exchange stability map", of the original parent protein, reflecting fidelity of structure in the daughter proteins.

Once crystals are obtained from the protein of interest and/or modified forms thereof, the crystals are subjected to crystallographic structure determination utilizing X-ray diffraction techniques as are known in the art. Diffraction patterns are used to determine the atomic or structure coordinates that define the three-dimensional structure of a protein molecule.

"Structure coordinates" refers to Cartesian coordinates (x, y, and z positions) derived from mathematical equations involving Fourier synthesis as determined from patterns obtained via diffraction of a monochromatic beam of X-rays by the atoms (scattering centers) of a polypeptide in crystal form. Diffraction data are used to calculate electron density maps of repeating protein units in the crystal (unit cell). Electron density maps are used to establish the positions of individual atoms within a crystal's unit cell. The term "crystal structure coordinates" refers to mathematical coordinates derived from mathematical equations related to the patterns obtained on diffraction of a monochromatic beam of X-rays by the atoms (scattering centers) of a polypeptide in crystal form. The diffraction data are used to calculate an electron density map of the repeating unit of the crystal. The electron density maps are used to establish the positions of the individual atoms within the unit cell of the crystal.

The term "selenomethionine substitution" refers to the method of producing a chemically modified form of the crystal of a protein. The protein is expressed by bacteria in media that is depleted in methionine and supplemented with selenomethionine. Selenium is thereby incorporated into the crystal in place of methionine sulfurs. The location(s) of selenium are determined by X-ray diffraction analysis of the crystal. This information is used to generate the phase information used to construct a three-dimensional structure of the protein.

"Heavy atom derivatization" refers to a method of producing a chemically modified form of a crystal. In practice, a crystal is soaked in a solution containing heavy atom salts or organometallic compounds, e.g., lead chloride, gold thiomalate, thimerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel, T. L., and Johnson, N. L., Protein Crystallography, Academic Press (1976), which is incorporated herein by reference.

"Unit cell" refers to a basic parallelepiped shaped block. Regular assembly of such blocks may construct the entire volume of a crystal. Each unit cell comprises a complete representation of the unit pattern, the repetition of which builds up the crystal. "Space group" refers to the arrangement of symmetry elements within a crystal.

"Molecular replacement" refers to generating a preliminary model of a protein whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., Meth. Enzymol. 11:55-77, 1985; Rossmann, M G., ed., "The Molecular Replacement Method" 1972, Int, Sci. Rev. Ser., No. 13, Gordon & Breach, New York).

The above-described procedures of protein preparation, crystallization and structure determination are combined with powerful information obtained by hydrogen exchange analysis. A protein or polypeptide of interest is first labeled with an isotope of hydrogen other than $^1H$, for example deuterium ($^2H$) or tritium ($^3H$). This labeling is accomplished under essentially physiologic conditions by incubating the protein of interest in solutions substantially containing water composed of the isotope. The phenomenon of hydrogen exchange is used to substitute an isotope of hydrogen for at least one of the amide hydrogens on the amino acids of the protein of interest.

The term "protein" or "polypeptide" is used herein in a broad sense which includes, for example, polypeptides and oligopeptides, and derivatives thereof, such as glycoproteins, lipoproteins, and phosphoproteins, and metalloproteins. The essential requirement is that the protein contains one or more peptide (—NHCO—) bonds, as the amide hydrogen of the peptide bond (as well as in the side chains of certain amino acids) has certain properties which lends itself to analysis by proton exchange. The protein may be identical to a naturally occurring protein, or it may be a binding fragment or mutant of such a protein. The fragment or mutant may have the same or different binding characteristics relative to the parent protein.

Alternatively, hydrogen exchange data may be obtained from already formed crystals by creating microcrystalline suspensions of the protein incubating in deuterated water, under conditions where dissolution of the crystals is inhibited (for example, by employing a protein-saturated solution in $D_2O$). During this time deuterated water soaks rapidly into the crystals, and then further exchanges onto amides on the crystalline form of the protein at rates that depend on the three-dimensional structure of the protein in the crystal. At the end of the desired on-exchange time, the on-exchanged crystals are washed or filtered free of the bulk of solution phase protein. Deuterated, crystalline protein is then solubilized in a predominantly non-deuterated solvent, under hydrogen exchange quench conditions (for example, at about pH 2.7-3 and cold temperature of about 0-10° C.). Exchange rates can then be compared with those observed when the protein is on-exchanged in solution phase. This comparison allows direct identification of regions of the protein that are identical or different in structure in fluid versus crystal phase. This is an enormously powerful method, as at present, the only way to get this comparative information is to perform a complete NMR study on fluid-phase protein, a difficult and very time-consuming task Solvent accessible peptide amide hydrogens of a polypeptide or protein of interest are on-exchanged by contacting the polypeptide or protein with an isotope of hydrogen under conditions wherein the native solvent-accessible peptide amide hydrogens are replaced with the isotope (for example, deuterium or tritium), such as, for example, physiological conditions wherein the polypeptide or protein is folded into its native conformation. Peptide amide protons that are relatively inaccessible to solvent, such as those that are buried within the interior of the polypeptide or protein structure or those that participate in intramolecular hydrogen-bonding interactions, do not readily exchange with the isotopic hydrogens in the solvent. Thus, those peptide amide hydrogens that are more solvent-accessible are selectively labeled.

The numerous small peptide fragments that are produced and analyzed by the methods of the present invention are likely to all be in random coil configuration: they are small, with little opportunity for structure-forming interactions, and are continuously contacted with several structure-breaking denaturants. According to certain invention methods, deuterated proteins are shifted to slowed exchange conditions (that include a very acidic pH), admixed with denaturing guanidinium salts, optionally disulfide-reduced, subject to proteolysis to generate a population of small fragments, and then admixed with acetonitrile, again under very acid conditions. As these fragments are in random coil configuration, the rates of exchange of each amide, in each peptide, under the slowed exchange ("quench") conditions as employed herein can be calculated from a knowledge of the amino acid sequence of each fragment (Bai et al., supra) as well as determined experimentally by fragmentation-LC-MS analysis of initially equilibrium-deuterated protein or peptides. As demonstrated herein, such calculations and measurements are employed to provide precise corrections for deuterium losses from peptides that occur in the course of the analysis, and to provide an adjunctive method for further localizing deuterium on peptide amides, when the fragmentation data alone is insufficient to achieve the desired resolution.

The protein of interest is first labeled under conditions wherein native hydrogens are replaced by the isotope of hydrogen (this is the "on-exchange" step). The reaction conditions are then altered to slowed hydrogen exchange conditions, or exchange "quench" conditions for further analysis of exchange rates. The phrase "slowed hydrogen exchange conditions" as used herein, refers to conditions where the rate of exchange of normal hydrogen for an isotope of hydrogen at amide hydrogens freely exposed to solvent is reduced substantially, i.e., enough to allow sufficient time to determine, by the methods described herein, exchange rates and the location of amide hydrogen positions which had been labeled with heavy hydrogen. The hydrogen exchange rate is a function of such variables as temperature, pH and solvent, in addition to protein structure. The rate is decreased three fold for each 10° C. drop in temperature. In water, the minimum hydrogen exchange rate is at a pH of 2-3. The use of a temperatures in the range of about 0-10° C., and a pH in the range of about 2-3 is preferred. Most presently preferred are conditions of about 0° C. and pH 2.2. As conditions diverge from the optimum pH, the hydrogen exchange rate increases, typically by 10-fold per pH unit increase or decrease away from the minimum. Use of high concentrations of a polar, organic cosolvent shifts the pH min to higher pH, potentially as high as pH 6 and perhaps, with certain solvents, even higher.

At pH 2.2 and 0° C., the typical half life of a deuterium label at an amide position freely exposed to solvent water is about 70 minutes. Preferably, the slowed conditions of the present invention result in a half-life of at least 10 minutes, more preferably at least 60 minutes.

To achieve labeling of the protein of interest, the protein is incubated in buffer supplemented with deuterated water (preferably $^2H_2O$), preferably of high concentration, preferably greater than 25% mole fraction deuterated water. This results in the time dependent reversible incorporation of deuterium label into every peptide amide on the surface of the protein through the mechanism of hydrogen exchange. These amides are referred to herein as "solvent accessible". A suitable buffer is phosphate buffered saline (PBS; 0.15 mM NaCl, 10 mM $PO_4$ (pH 7.4)). The use of small incubation volumes (about 0.1-10 μl) containing high concentrations of protein (about 2-10 mg/ml) is preferred. This can be done, for example, by adding protein and buffer together in a tube, or by injecting an aliquot of protein solution into a flowing stream of isotope-containing buffer in a manner that results in the rapid mixing of the converging streams.

It is not necessary that the hydrogen exchange analysis rely on only a single choice of "on-exchange" time. Rather, the skilled worker may carry out the experiment using a range of on-exchange times, preferably spanning several orders of magnitude (seconds to days) to allow selection of on-exchange times which allow efficient labeling of the various peptide amides present in the protein, and at the same time minimize background labeling of other amide positions after off-exchange is completed.

In general, comparisons of the exchange behavior of alternative forms of a protein can be performed by either: (i) on-exchanging, in parallel, each of the forms of the protein, quenching exchange, performing localization studies on each form of the protein, and then comparing the deuteration patterns seen across the set of protein forms; and (ii) on-exchanging one form of the protein, transforming the protein to its alternative form (for example, inducing a conformation change, binding a ligand, etc.) and then off-exchanging the protein, said off-exchange terminated by quenching exchange. In both methods of analysis, the ratio of the exchange rates observed at any amide position is termed its exchange "protection factor", and this ratio is related to the change in free energy ("delta G") in the atomic environs of said amide by the relationship Delta G=−T ln (protection factor).

For off-exchange, the labeled protein is transferred to physiologic buffers identical to those employed during on-exchange, but which are substantially free of isotope. The incorporated isotopic label on the protein then exchanges off the protein at rates identical to its on-exchange rate everywhere except at amides which have been slowed in their exchange rate, for example, by virtue of the interaction of protein with a binding partner, or by conformational change.

In general, off-exchange is allowed to proceed for 2 to 20 times, more preferably about 10 times longer than the on-exchange period, as this allows off-exchange from the protein of greater than 99% of the on-exchanged isotope label.

In preferred embodiments, the off-exchange procedure may be accomplished by use of perfusive HPLC supports that allow rapid separation of peptide/protein from solvent (e.g., Poros™ columns, PerSeptive Biosystems, Boston, Mass.), or by simple dilution into undeuterated solvent.

Determination of amide exchange rates in proteins requires performing studies across a broad range of on and off-exchange intervals. For brief on- and off-exchange intervals (1-2 minutes or less), the time necessary for binding protein to be applied to the matrix-containing column and both bind to binding partner and start off-exchange may be excessively long with the above approach. While the above approach will work well with on and off-exchange intervals as short as 1-2 minutes, limits to the ability of support matrices to promote the rapid molecular interaction of binding protein with binding partner will make study of exchange intervals shorter than this problematic with the above approach. While homogenous liquid phase reactions between a receptor and ligand may be quite fast (less than $1/10^{th}$ of a second), if one of the pair has been previously attached to a surface, then limitations to "transport processes" can substantially slow the binding interaction (to seconds).

To overcome this difficulty, the following modified approach is utilized for study of brief exchange intervals. Binding protein is contacted with isotope-containing solvent as above, but at the end of the desired on-exchange interval, the solution is contacted with a small volume of liquid phase binding partner. As both binding components are in homogenous liquid phase, complex formation occurs at intervals well less than one second. An excess of aqueous solvent devoid of heavy hydrogen is then optionally added to the binding protein-binding partner complex mixture to effect a substantial dilution ($1/10$ to $1/1000$, preferably $1/100$) of the isotope in the mixture, thereby initiating off-exchange. This mixture is then rapidly applied to a support matrix column (preferably by the flowing stream method) that is capable of binding and attaching the binding partner by any of a variety of methods that are operative at physiologic pH, including the avidin-biotin interaction (in this case the binding partner having been previously biotinylated and the matrix support bearing previously attached avidin) or by way of other well-characterized binding pair interactions.

Continued flow of solvent without isotope over the binding protein-binding partner-bound support matrix further initiates off-exchange. At the end of off-exchange, binding protein is then eluted and removed from the column with an appropriate buffer capable of dissociating the binding protein-binding partner complex; the binding partner-solid support interaction; or both. Preferably one employs procedures that are capable of selectively disrupting the binding protein-binding partner complex without disrupting the support matrix-binding partner interaction (for example, the avidin-biotin interaction) as this will result in the preferred specific elution and recovery from the column of pure off-exchanged binding protein, unadulterated with confounding binding partner.

A preferred embodiment employs binding protein that is first contacted with isotope-containing solvent, and, at the end of the desired on-exchange interval, this solution is contacted with a solution of a previously biotinylated binding partner, with such prior biotinylation being accomplished by any of a number of well known procedures. Complex formation between biotinylated binding partner and binding protein is allowed to occur, generally being complete in less than a second, and then this mixture is optionally diluted to initiate off-exchange, and injected into a flowing stream of physiologic aqueous solvent flowing over a column of support matrix consisting of avidin covalently bound to the matrix. The avidin utilized may variously consist of streptavidin, egg white avidin, or monomeric avidin, or other modified forms of avidin. The linkage to matrix may be by way of any of a variety of functionalities including sodium cyanoborohydride-stabilized Schiff base or that resulting from the cyanogen bromide procedure as applied to carbohydrate matrices. The solid matrices may consist of cross-linked agarose particles or preferably perfusive supports such as those (Poros products) provided by the Perceptive Biosystems company (solid support 20-AL and the like).

For many binding pairs off-exchange may be terminated and selective elution of binding protein accomplished by simply shifting pH to about 2.2 at 0° C. These conditions disrupt many types of binding protein-binding partner complexes but do not disrupt the avidin-biotin interaction, thereby allowing retention on the column of biotinylated binding partner. If shifting to acidic conditions by itself does not result in elution of a particular binding protein, then one of a variety of additional denaturants can be added to the elution solvent, including urea, guanidine hydrochloride, and guanidine thiocyanate at concentrations (preferably 2-4 M guanidine hydrochloride, 1-2 M guanidine thiocyanate) sufficient to elute binding protein but not at the same time disrupt the avidin-biotin interaction and thereby co-elute the binding partner. In general, these conditions do not disrupt the avidin-biotin interaction, even at room temperature. Finally, as above, reductants, such as TCEP, can optionally be admixed with the elution solvent so that it will be present in the binding partner sample when desired.

An additional advantage of the support matrix approach to exchange reactions is that certain embodiments require that the binding protein and binding partner of interest be on-exchanged, complexed with each other, and off-exchanged while present within a mixture of other proteins and biomolecules. In these embodiments, as off-exchange proceeds, it is necessary to isolate the specific binding pair complex of interest. In a preferred embodiment this is accomplished with support matrices as follows. Previously biotinylated binding partner is contacted with a sample containing a mixture of proteins, perhaps a suspension of intact, living cells, or a whole cell extract or digest, or a biologic fluid, such as serum, plasma or blood that also contains the binding protein of interest. Said contacting and mixing results in formation of the biotinylated binding partner-binding protein complex. This mixture, of which the binding pair may be a minor component, is then passed over the aforementioned support matrix containing avidin, wherein the biotinylated complex of interest will specifically attach to the matrix. Washing of the support with aqueous solvent continues (or when desired may initiate) off-exchange and removes from the matrix the irrelevant proteins that were present in the initial mixture, and thereby purifies the binding protein-binding partner complex. At the end of the off-exchange interval, the purified binding protein is simultaneously eluted and shifted to slow exchange conditions as above with an aliquot of appropriate eluent.

Certain target proteins require lipid or detergent environments for expression of their physiologic structure and function. Slowed-exchange-compatible proteolysis of such protein targets can be accomplished with current methods, but further analysis (c18 reversed-phase chromatography, ESI-MS) is not possible because of interference from the associated lipids and/or detergents. The use of microfluidic devices allows such interfering substances to be efficiently and rapidly separated from the peptide fragments, allowing their effective analysis, for example using deuterium exchange-mass spectrometry (DXMS).

Through the use of microfluidic devices, solutions containing target proteins have their buffer composition changed by allowing effective diffusion of the smaller buffer components ($^2H_2O$, $H_2O$, salts, ligands) without effective diffusion of the target protein. In one embodiment, small regenerated cellulose microdialysis fibers (13,000 or 18,000 MWCO, approximately 200 u ID; Spectrum Inc.) are encased in PEEK tubing ($^{15}/_{1000}$ inch ID) with end fittings that allow a countercurrent sheath solvent flow of exchange solvent while the protein solution flows through the microdialysis fiber. Such devices are capable of very efficient $^2H_2O$ exchange in short times, for example, effecting change to 95% $^2H_2O$ in three seconds at room temperature. Typical flow rates to achieve this end consist of 50 μl/minute for protein solution and 1000 μl/minute for sheath solution.

Such microfluidic devices can also be used to semipurify peptide mixtures that are contaminated with interfering lipids and detergents, such as proteolytic digests of membrane protein preparations. In this application, the proteolytic digest of such a protein is passed through the bore of the microdialysis fiber (flow 5-50 μl/minute) while the countercurrent sheath flow (100-400 μl/min), into which peptide fragments can transfer, (but not the more slowly diffusing and non-dializable lipid/detergent micelles), is directed to and collected on the c18 column for subsequent acetonitrile-gradient elution and MS. The result is that the digest peptides can be analyzed without interference from the lipid/detergent.

Non-constrained devices which utilize differential diffusion to effect changes in buffer composition (such as the "H-reactor" patented by Micronics, Inc.) can also be employed for these purposes. With these devices, flow of sample and exchange buffer is concurrent, not countercurrent, and exchange is therefore necessarily less efficient for a given volume of exchange buffer employed.

Protein Fragmentation Methods

A. Improved Proteolysis Fragmentation

Figure 3:
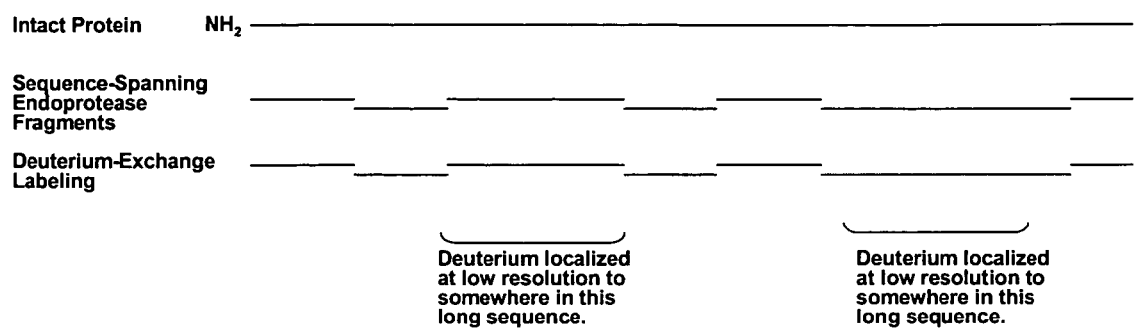
FIG. 3 outlines an exemplary deuterium label localization method. Given the limited ability of pepsin to produce varied fragments under these conditions, the goal of the method is to produce one peptide from each region of the target protein's primary sequence.
Figure 4:
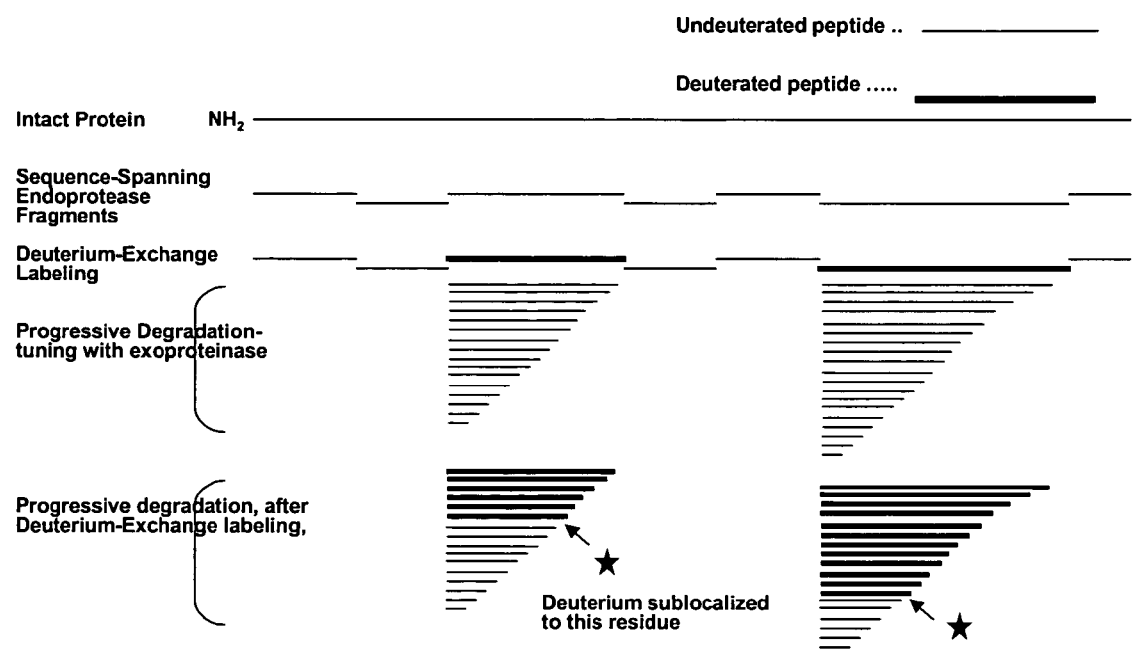
FIG. 4 depicts a progressive degradation method for deuterium localization in which a target protein is first subjected to endopeptidase-dependent fragmentation as in FIG. 3, followed by carboxypeptidase-dependent sub-fragmentation.

In one preferred method of hydrogen exchange analysis, improved proteolysis fragmentation is employed. In this improved proteolysis method, a simple endopeptidase proteolysis is used to generate a dense sequence-overlapping population of protein fragments for analysis. Prior teachings had found that the common acid-resistant endopeptidases alone, such as pepsin, were not useful in highly localizing amide hydrogen exchange due to insufficient ability to fragment target proteins under acceptable slowed exchange conditions. Pepsin, as employed in the prior art typically had generated a relatively small number of fragments, generally 10-25 amino acids long. The label incorporated on these few useable pepsin-generated peptides was then used to infer the location of label, at best localizing within a range of about 10-25 amino acids (see FIG. 3). Subsequent art taught the use of acid-resistant carboxypeptidases (progressive degradation) after an initial employment of endopeptidases, to localize the labeled amino acid positions within peptides generated when a detailed resolution, such as within 1-5 amino acid residues, is desired (see FIG. 4).

Figure 5:
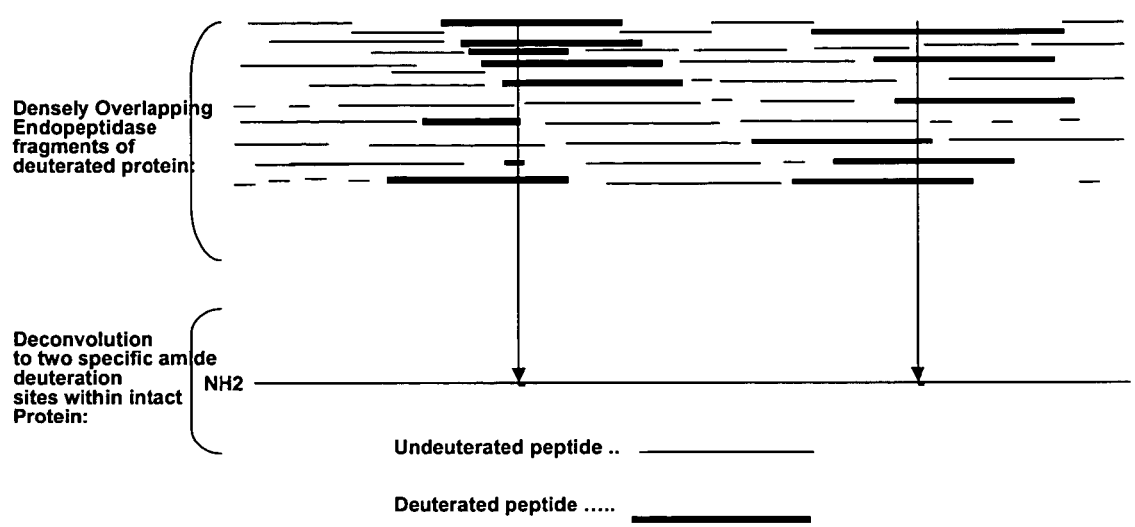
FIG. 5 depicts a simplified schematic of exemplary methods of high resolution hydrogen exchange analysis for use in invention methods, in which a densely overlapping set of target protein fragments is generated in a single step by enhanced use of endoproteinases. In this schematic, the functionally labeled protein was tagged with two sequence-discontinuous deuterons, and every deuterated peptide produced by subsequent endopeptidase fragmentation was found to bear one deuteron.

In accordance with the present invention, improved methods that dramatically speed proteolysis, and modulate the sites and patterns of proteolysis by endoproteinases are employed so as to produce highly varied and highly efficient fragmentation of the labeled protein in a single step, thereby avoiding the use of carboxypeptidases completely, an improvement which simplifies the fragmentation and affords a considerable savings of time and cost (see FIG. 5). While these improvements work best in combination with each other, they can be grouped into 3 categories: (i) use of denaturants (systematically varying the type, concentration, duration of denaturation, type of endoproteinase)s) employed, and the duration of endopeptidase digestion) to greatly speed proteolysis and modulate the resulting pattern of fragmentation; (ii) use of solid-state proteolysis with acid-resistant endopeptidases selected for their efficiency and distinctive fragmentation preferences with respect to each other under optimal quench conditions; and (iii) use of water-soluble phosphines to effect rapid and efficient disulfide reduction under quench conditions The use of such endopeptidases under optimized conditions described herein routinely results in the generation of a population of endopeptidase-generated fragments substantially spanning the full length of the majority of proteins studied to date, and, as importantly, yields a large number of additional peptides that partially and mutually overlap in sequence with each other, all obtainable in useful yield. Preferably, the population of fragments contains sequence-overlapping fragments wherein more than half, more preferably 60%-80%, of the members of the population have sequences that are overlapped by the sequences of other members by all but 1-5 amino acid residues. In addition, it is preferable that a majority of members of the population of fragments is present in an analytically sufficient quantity to permit its further characterization, for example, by LC-MS analysis.

An example of the application of this improved proteolysis method and the power of deuterium exchange-mass spectrometry (DXMS) to elucidate protein structure and organization can be found in Hamuro et al., *J. Mol. Biol.* 321:703-714, 2002. Additional references include Hamuro and Woods, *J. Cell. Biochem.*, 37:89-98, 2001; Hamuro et al., *J. Mol. Biol.* 323:871-881, 2002; Hamuro et al., *J. Mol. Biol.* 327:1065-1076, 2003; Englander et al., *Proc. Natl. Acad. Sci. USA* 100:7057-7062, 2003; and Zawadzki et al., *Protein Sci.* 12:1980-1990, 2003.

B. Progressive Proteolysis Fragmentation

In another preferred method of hydrogen exchange analysis, progressive proteolysis (as defined above) is employed to produce protein fragments for label localization. The protein is subjected to a first fragmentation, e.g., with an acid stable proteolytic enzyme, e.g., an endopeptidase such as, for example, pepsin, under slow hydrogen exchange conditions to generate protein fragments. Following the first fragmentation, the resolution of the isotopic hydrogen labeled amides is equivalent to the protein fragment size. Finer localization of the labels is achieved by analysis of subfragments of the protein fragments, which subfragments are generated by progressive degradation of each isolated, labeled protein fragment under slowed exchange conditions. Alternatively, if the protein is smaller than about 30 kDa, the intact protein may be subjected to progressive degradation.

For the purpose of the present invention, a protein or a protein fragment is said to be "progressively" (or "stepwise" or "sequentially") degraded if a series of fragments are obtained which are similar to the series of fragments which would be achieved using an ideal exopeptidase, as defined and described in U.S. Pat. No. 6,291,189, column 7, line 58 through column 8, line 33. An ideal exopeptidase will only remove a terminal amino acid. Thus, if the n amino acids of a protein fragment were labeled $A_1$ to $A_n$ (the numbering starting at the terminus at which the degradation occurs), the series of subfragments produced by an ideal exopeptidase would be $A_2 \sim\!\sim\!\sim A_n$, $A_3 \sim\!\sim\!\sim A_{n-1}$-$A_n$, and finally $A_n$.

Preferably each subfragment of the series of subfragments obtained is shorter than the preceding subfragment in the series by a single terminal amino acid residue. However, it is to be understood that exopeptidases do not necessarily react in an ideal manner. Thus, for purposes of the present invention, a protein fragment is said to be progressively degraded, if the series of subfragments generated thereby is one wherein each subfragment in the series is composed of about 1-5 fewer terminal amino acid residues from one end than the preceding subfragment in the series, with preservation of the common other end of the subfamily members. The analyses of the successive subfragments are correlated in order to determine which amino acids of the parent protein fragment were isotopically labeled.

Protein Fragmentation

When the progressive proteolysis protein fragmentation method is employed, the protein is subjected to acid proteolysis with high concentrations of at least one protease that is stable and proteolytically active in the aforementioned slowed hydrogen exchange conditions, e.g., a pH of about 2-3, and a temperature of about 0-4° C., followed by C-terminal subfragmentation with an acid resistant carboxypeptidase, or N-terminal degradation with an acid resistant aminopeptidase. Suitable proteases for the first step include, for example, pepsin (Rogero et al., *Meth. Enzymol.* 131:508-517,1986.), cathepsin-D (Takayuki et al., *Meth. Enzymol.* 80:565-581, 1981) *Aspergillus* proteases (Krishnan et al., *J. Chromatography* 329:165-170, 1985; Xiaoming et al., *Carlsberg Res. Commun.* 54:241-249, 1989; Zhu et al., *App. Envir. Microbiol.* 56:837-843, 1990), thermolysin (Fusek et al., *J. Biol. Chem.* 265:1496-1501, 1990) and mixtures of these proteases. In one preferred embodiment, pepsin is used, preferably at a concentration of 10 mg/mL pepsin at a temperature of about 0° C. and a pH of about 2.7 for about 5-30 minutes, preferably about 10 minutes.

Separation of Protein Fragments

In one embodiment of the invention, proteolytically fragmented, isotopic hydrogen-labeled protein fragments are separated prior to progressive degradation by means capable of resolving the protein fragments. Preferably, separation is accomplished by reverse phase high performance liquid chromatography (RP-HPLC) utilizing one or more of a number of potential chromatographic supports including $C_4$, $C_{18}$, phenol and ion exchange, preferably $C_{18}$.

Separating the isotopically labeled fragments from the many unlabeled peptides generated by fragmentation of the protein is done under conditions which minimize off-exchange of isotopic hydrogen from the labeled amide sites of the protein fragments. Small protein fragments have little secondary structure, thus amide hydrogens therein freely exchange with hydrogen from the solvent. Conditions for proteolysis and protein fragment separation must therefore be adjusted to slow off-exchange of isotopic hydrogen in order for the isotopic label to remain in place for a time sufficient to complete the method.

The RP-HPLC separation is preferably performed at a pH of about 2.1-3.5 and at a temperature of about 0-4.0° C., more preferably, at a pH of about 2.7 and at a temperature of about 0° C. The preferred separation conditions may be generated by employment of any buffer systems which operate within the above pH ranges, including, for example, citrate, phosphate, and acetate, preferably phosphate. Protein fragments are eluted from the reverse phase column using a gradient of similarly buffered polar co-solvents including methanol, dioxane, propanol, and acetonitrile, preferably acetonitrile. Eluted protein fragments are detected, preferably by ultraviolet light absorption spectroscopy performed at frequencies between about 200 and about 300 nM, preferably about 214 nM. The isotopic label is detected in a sampled fraction of the HPLC column effluent, preferably via either scintillation counting for a tritium label or by mass spectrometry for a deuterium label.

Acid proteases in general have broad cleavage specificity. Thus, they fragment the protein into a large number of different peptides. RP-HPLC resolution of co-migrating multiple peptides is substantially improved by employing a two-dimensional RP-HPLC separation. Preferably, the two sequential RP-HPLC separations are performed at substantially different pH's, for example, a pH of about 2.7 for one separation and about 2.1 for the other sequential separation.

HPLC fractions from a first separation, containing isotopically labeled protein fragments, are then optionally subjected to a second dimension RP-HPLC separation. The second separation may be performed at a pH of from about 2.1 to about 3.5 and at a temperature of from about 0 to about 4° C., more preferably, at a pH of about 2.1 and at a temperature of about 0° C. The pH conditions for the chromatographic separation are maintained by employing a buffer system which operates at this pH, including citrate, chloride, acetate, phosphate, more preferably TFA (0.1-0.115%). Protein fragments are eluted from their reverse phase column with a similarly buffered gradient of polar co-solvents including methanol, dioxane, propanol, more preferably acetonitrile. Eluted protein fragments are detected, the content of isotopic label is measured, and labeled peptides identified as in the first HPLC dimension described above. Labeled protein fragments are isolated by collection of the appropriate fraction of column effluent. Elution solvents are removed by evaporation. The remaining purified protein fragments are each characterized as to primary amino acid structure by conventional techniques such as, for example, amino acid analysis of complete acid hydrolysates or gas-phase Edman degradation microsequencing. The location of the labeled protein fragments within the primary sequence of the intact protein may then be determined by referencing the previously known amino acid sequence of the intact protein. Residual phosphate frequently interferes with the chemical reactions required for amino acid analysis and Edman degradation. This interference is eliminated by the use of trifluoroacetic acid (TFA) in the second dimension buffer so that no residual salt, i.e., phosphate remains after solvent evaporation In one embodiment, proteolytically fragmented, isotopic hydrogen-labeled protein fragments are first separated at pH 2.7 in phosphate buffered solvents and each eluted fragment peak fraction which contains isotopically-labeled amides is identified, collected, and then subjected to a second HPLC separation performed in TFA-buffered solvents at pH 2.1.

High Resolution Sublocalization of Labeled Amides Within Label-Bearing Protein Fragments 1. Subfragmentation of Protein Fragments To localize an isotopic hydrogen labeled peptide amide to the single amino acid level, every peptide bond within a purified label-bearing protein fragment is systematically cleaved. Acidic conditions must be used for this proteolysis because the small protein fragments and subfragments generated have no stable conformational structure and rapid loss of isotopic hydrogen label from the amides would occur if rates of exchange were not slowed by ambient acidic pH.

Progressive degradation is preferably achieved by treatment with at least one acid stable exopeptidase enzyme, more preferably with at least one carboxypeptidase. The progressive degradation is performed at acidic pH to minimize isotopic hydrogen losses. Thus, enzymes that are substantially inactivated by the required acidic buffers are of limited use in the method of the invention. However, several carboxypeptidases are enzymatically active under acid conditions, and thus are suitable for proteolysis of protein fragments under acidic conditions, e.g., pH 2-3.

Most known acid-reactive proteases cleave peptides in a nonspecific manner similar to pepsin. One class of acid-reactive proteases, the carboxypeptidases, is able to generate all required subfragments of proteolytically-generated protein fragments in quantities sufficient for high resolution localization of an isotopic hydrogen label. Many carboxypeptidases are active at pH 2-3 and sequentially cleave amino acids from the carboxy terminus of protein fragments. Such enzymes include, for example, carboxypeptidases P, Y, W, and C (Breddam, *Carlsberg Res. Commun.* 51:83-128, 1986). The need to minimize isotopic hydrogen losses precludes the use of carboxypeptidases which are inactive in acidic (pH 2.7) buffers, such as carboxypeptidases A and B.

Progressive degradation of purified isotopic hydrogen label-bearing protein fragments is preferably performed with one or more acid resistant carboxypeptidase under conditions that produce a complete set of amide-labeled subfragments, wherein each subfragment is shorter than the preceding subfragment by 1-5 carboxy terminal amino acids, preferably by a single carboxy-terminal amino acid. HPLC analysis of the resulting series of subfragments allows the reliable assignment of label to a particular amide position within the parent labeled protein fragment.

In one preferred embodiment, isotopic hydrogen-labeled proteins are nonspecifically fragmented with pepsin or one or more pepsin-like proteases. The resulting labeled protein fragments are isolated by two-dimensional HPLC. These labeled protein fragments are then exhaustively subfragmented by progressive degradation with one or more acid-reactive carboxypeptidases. The resulting digests are then analyzed via RP-HPLC performed at a temperature of about 0° C. in TFA-containing buffers (pH about 2.1). Each of the generated subfragments (typically 5-20) is then identified as to its structure and content of isotopic hydrogen label. The isotopic hydrogen label is thereby assigned to specific peptide amide positions.

Controlled progressive degradation from the carboxy-terminus of isotopic hydrogen labeled protein fragments with carboxypeptidases can be performed under conditions which result in the production of analytically sufficient quantities of a series of carboxy-terminal truncated subfragments, each shorter than the preceding subfragment by a single carboxy-terminal amino acid. As each carboxy-terminal amino acid of the labeled protein fragment is sequentially cleaved by the carboxypeptidase, the peptide amide nitrogen which exhibits slow hydrogen exchange under the process conditions is converted to a secondary amine which exhibits rapid hydrogen exchange. Thus any isotopic hydrogen label at that nitrogen is lost from the protein subfragment within seconds, even at acidic pH. A difference in the molar quantity of label associated with any two sequential subfragments indicates that the isotopic label is localized at the peptide bond amide between the two subfragments.

2. Location of the Isotopic Hydrogen Label

In one preferred embodiment, synthetic peptides are produced (by standard peptide synthesis techniques) that are identical in primary amino acid sequence to each of the labeled proteolytically-generated protein fragments. The synthetic peptides may then be used in preliminary carboxypeptidase subfragmentation at a pH of about 2.7 and a temperature of about 0° C., and HPLC (in TFA-buffered solvents) studies to determine: 1) the optimal conditions of proteolysis time and protease concentration which result in the production and identification of all possible carboxypeptidase products of the protein fragment under study; and 2) the HPLC elution position (mobility) of each carboxypeptidase-generated subfragment of synthetic peptide.

In one preferred aspect thereof, a set of synthetic peptides may be produced containing all possible carboxy-terminal truncated subfragments which an acid carboxypeptidase could produce upon treatment of a "parent" protein fragment. These synthetic peptides serve as HPLC mobility identity standards and enable the identification of carboxypeptidase-generated subfragments of the labeled protein fragment. Certain subfragments may be enzymatically produced by carboxypeptidase in quantities insufficient for direct amino acid analysis or sequencing. However, the quantity of the carboxypeptidase-generated subfragments is sufficient for identification by measuring HPLC mobility of such subfragments and comparing to the mobility of the synthetic peptides. Protein fragments and subfragments can be detected and quantified by standard in-line spectrophotometers (typically UV absorbance at 200-214 nM) at levels well below the amounts needed for amino acid analysis or gas-phase Edman sequencing.

After these preliminary studies, the proteolytically-generated HPLC-isolated, isotopically-labeled protein fragment is subfragmented with a carboxypeptidase and analyzed under the foregoing experimentally optimized conditions. The identity of each fragment is determined (by peptide sequencing or by reference to the mobility of synthetic peptide mobility marker) and the amount of isotopic hydrogen associated with each peptide subfragment is determined.

Denaturation and Disulfide Reduction

With some proteins, there is an absolute requirement for the employment of denaturants to effect fragmentation under quench conditions. An example of a protein with such an absolute dependency is Hen Egg White Lysozyme (HEL). In a preferred embodiment, the labeled protein is exposed, before fragmentation, to denaturing conditions compatible with slow hydrogen exchange and sufficiently strong to denature the protein enough to render it adequately susceptible to the intended proteolytic treatment. If these denaturing conditions would also denature the protease, then, prior to proteolysis, the denatured protein is switched to less denatured conditions (still compatible with slow H-exchange) sufficiently denaturing to maintain the protein in a protease-susceptible state but substantially less harmful to the protease in question. Preferably, the initial denaturant is guanidine thiocyanate, and the less denaturing condition is obtained by dilution with guanidine hydrochloride. Guanidine hydrochloride is an effective denaturant at a concentration of about 0.05-4 M.

In previous studies by Englander et al. and others recited above, proteolytic fragmentation of labeled proteins under slowed-exchange conditions was suitably accomplished by simply shifting the protein's pH to 2.7, adding high concentrations of liquid phase pepsin, followed by (10 minute) incubation at 0° C. With the proteins studied and reported by others to date, simply shifting pH from that of physiologic (7.0) to 2.7 was sufficient to render them sufficiently denatured as to be susceptible to pepsin proteolysis at 0° C. Furthermore, these reported proteins, in general, did not contain disulfide bonds that interfered with effective denaturation by such (acid) pH conditions or contain disulfide bonds within portions of the protein under study with the technique.

However, in accordance with the present invention, it has been found that other proteins (for example, HEL) are negligibly denatured and are not substantially susceptible to pepsin proteolysis when continuously incubated at comparable acidic pH and depressed temperature (10-0° C.) for several hours. This is likely the consequence of the existence of a thermal barrier to denaturation for many proteins incubated in many denaturants; i.e., denaturation of proteins at lower temperatures (10-0° C.), an absolute requirement for hydrogen exchange quench, is often inefficient and a slow process, incompatible with the requirement of medium resolution hydrogen exchange techniques that manipulations be performed rapidly, such that the attached label is substantially retained at functionally labeled amides of the protein.

Using the methods of the present invention, it has been discovered that such proteins become extraordinarily susceptible to pepsin proteolysis at 0° C. when they are treated with the sequential denaturation procedure described below.

While proteins are often subjected to purposeful denaturation with agents other than a pH shift prior to digestion with pepsin, this has never been done at depressed temperatures (10-0° C.) before, and the it has been discovered herein that while guanidine thiocyanate at the indicated concentrations is sufficient to suitably denature and render susceptible to pepsin proteolysis proteins at 10-0° C., several other strong denaturants, including urea, HCl, sodium dodecyl sulfate (SDS) and guanidine HCl, were, at least when used alone, unable to adequately denature lysozyme at these low temperatures. However, the concentrations of guanidine thiocyanate required for such denaturation are incompatible with pepsin digestion; i.e., they denature the pepsin enzyme before it can act on the denatured binding protein. When the guanidine thiocyanate is removed (at 10-0° C.) from the solution after protein denaturation has been accomplished in an attempt to overcome this inhibition of pepsin activity, the protein rapidly refolds and/or aggregates, which renders it again refractory to the proteolytic action of pepsin.

It has been discovered herein that if proteins are first denatured in about 1.5-4 M (preferably $\geq$2M) guanidine thiocyanate at 0° C. and the concentration of thiocyanate then reduced to preferably $\leq$0.5 M, while at the same time the guanidine ion is maintained at about 0.05-4 M (preferably $\geq$2M) (by diluting the guanidine thiocyanate-protein mixture into guanidine hydrochloride solution), the denatured protein remains in solution, remains denatured, and the enzyme pepsin remains proteolytically active against the denatured protein in this solution at 0° C. The denatured (or denatured and reduced) protein solution is then passed over a pepsin-solid-support column, resulting in efficient and rapid fragmentation of the protein (in less than 1 minute). The fragments can be, and usually are, immediately analyzed on RP-HPLC without unnecessary contamination of the peptide mixture with the enzyme pepsin or fragments of the enzyme pepsin. Such contamination is problematic with the technique as taught by Englander et al., as high concentrations of pepsin (often equal in mass to the protein under study) are employed, to force the proteolysis to occur sufficiently rapidly at 0° C.

The stability of pepsin-agarose to this digestion buffer is such that no detectable degradation in the performance of the pepsin column employed by the methods of the present invention has occurred after being used to proteolyze more than 500 samples over 1 year. No pepsin autodigestion takes place under these conditions. Denaturation without concomitant reduction of the binding protein may be accomplished by contacting it (at 0-5° C.) with a solution containing $\geq$2M guanidine thiocyanate (pH 2.7), followed by the addition of an equal volume of 4 M guanidine hydrochloride (pH 2.7).

Subsequent to this discovery of the extraordinary stability to denaturation of HEL under quench conditions, and the foregoing remedy, it has been found that all other proteins studied to date by methods of the present invention are susceptible, at least to a minimal degree, to pepsin proteolysis under simple quench conditions, but that the speed and extent of fragmentation can be dramatically increased by the addition of suitable concentrations of guanidine hydrochloride (GuHCl) alone, without the use of guanidine thiocyanate. There is considerable virtue in avoiding the use of thiocyanate when possible: there is a variable (often severe) aggregation and precipitation of some of the denatured protein as the thiocyanate is diluted out prior to proteolysis, greatly confounded automated sample processing.

Figure 6:
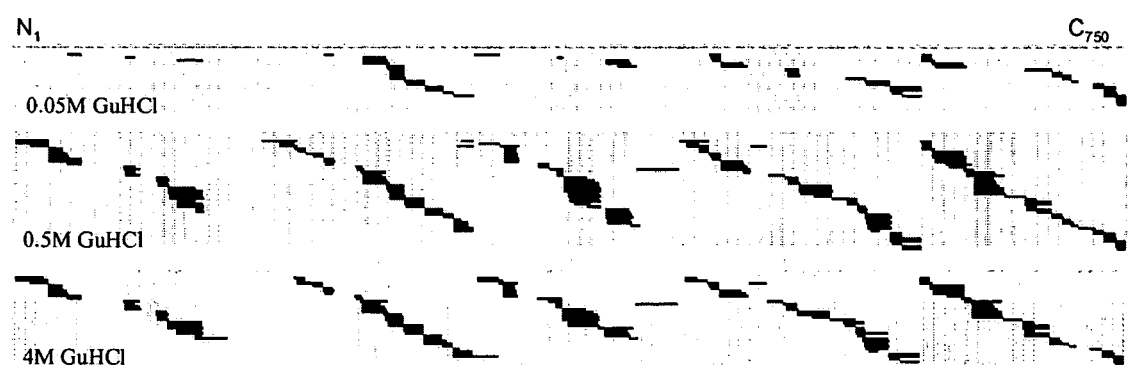
FIG. 6 illustrates the effect of varying concentrations of guanidine hydrochloride (0-4 M GuHCl) on the fragmentation of protein phospholipase A2, under quench conditions (pH 2.2, 0° C.), with solid-phase pepsin. When no GuHCl was used, less than 15 peptides in sufficient yield were identified (data not shown). When 0.05 M GuHCl was used, more than 70 high quality peptides were obtained, with further improvement when 0.5 M denaturant was employed. While 4.0 M denaturant resulted in the identification of additional peptides, some were also lost when compared to the 0.5 M digest.

FIG. 6 presents the fragmentation patterns seen when the protein phospholipase A2, under quench conditions (pH 2.2, 0° C.), is incubated with varying concentrations of GuHCl (0-4M) for 20 seconds, and then contacted with a pepsin-solid support column (30 mg/ml, Poros 20-AL media; 66 microliters bed volume) for an additional 30 seconds. Fragments were contemporaneously loaded on a microbore c18 column and then eluted with an acetonitrile gradient over 10 minutes, again at pH 2.2, 0° C., with the effluent directed to a Finnigan LCQ mass spectrometer operating at a capillary temperature of 200° C. Data was acquired in both data dependent MS2 mode (to allow peptide identification) and in MS1 mode (to assess the suitability of the isotopic envelope data for subsequent deuterium quantification (signal, signal to noise, spectral overlap with confounding fragments). When no GuHCl was used, less than 15 peptides in sufficient yield were identified (data not shown). When 0.05 M GuHCl was used, more than 70 high quality peptides were obtained, with further improvement when 0.5 M denaturant was employed. While 4.0 M denaturant resulted in the identification of additional peptides, some were also lost when compared to the 0.5M digest.

Figure 2:
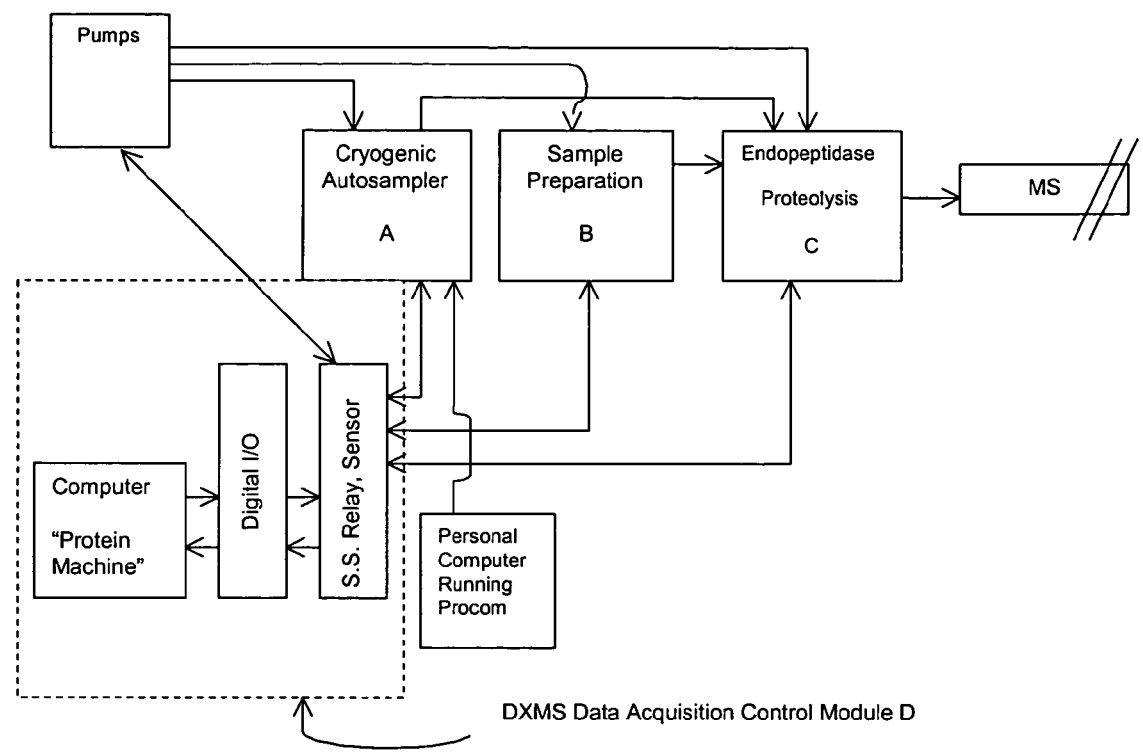
FIG. 2 is a schematic of an exemplary automated high resolution hydrogen exchange apparatus useful in the methods of the present invention.

In accordance with the present invention, it has been found that several variables behave independently in determining the speed and pattern of digestion, and that their effects are distinctive for each target protein studied. Typically, up to 30 combinations of these variables are evaluated (employing the automated features of the hydrogen exchange apparatus described herein, see FIG. 2) to establish optimal fragmentation conditions for the protein under study. These independent variables include the type of denaturant (e.g., GuSCN versus GuHCl); its concentration preferably (0.05-4M); the time the denaturant is allowed to act on the protein prior to fragmentation (preferably 0 to 3 minutes); the type(s) of endoproteinases employed; and the time allowed for digestion (preferably 20 seconds to 2 minutes). For most proteins studied, GuHCl, at a concentration of 0.5M and 30 seconds fragmentation on a pepsin column as above is near-optimal, though more extensive tuning will likely improve the fragmentation map.

Figure 7:
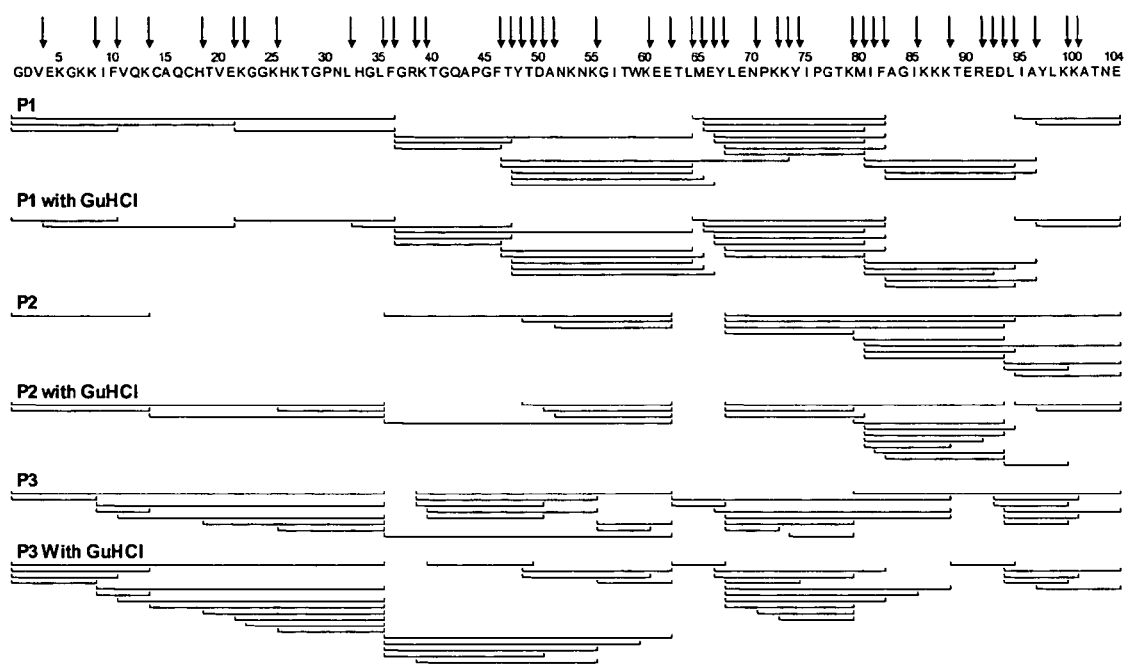
FIG. 7 presents results obtained when horse cytochrome c was quenched with or without 0.5M GuHCl, and then fragmented with either pepsin (P 1), Newlase (P2) or Fungal Protease XIII (P3) coupled to perfusive supports (20-30 mg/mi). Considerable variation in digestion pattern and yield is seen with the varying conditions. The arrows at the top of the figure indicates the positions of the C- and N-termini of the aggregate peptides produced, highlighting the extreme degree of overlap of the set of peptide fragments produced (SEQ ID NO: 1).

FIG. 7 presents results obtained when horse cytochrome c was quenched with or without 0.5M GuHCl, and then fragmented with either pepsin (P1), Newlase (P2) or Fungal Protease XIII (P3) coupled to perfusive supports (20-30 mg/ml), and analyzed as in FIG. 6. Considerable variation in digestion pattern and yield is seen with the several conditions. The arrows at the top of the figure indicate the positions of the C- and N-termini of the aggregate peptides produced, highlighting the extreme degree of overlap of the resulting set of peptide fragments. Even when denaturant is omitted the results of the solid state pepsin digestions were superior to those disclosed by others in which cytochrome c was fragmented with liquid-phase pepsin, where fewer than 15 useful peptides were obtained in a 10 minute digestion.

Figure 8:
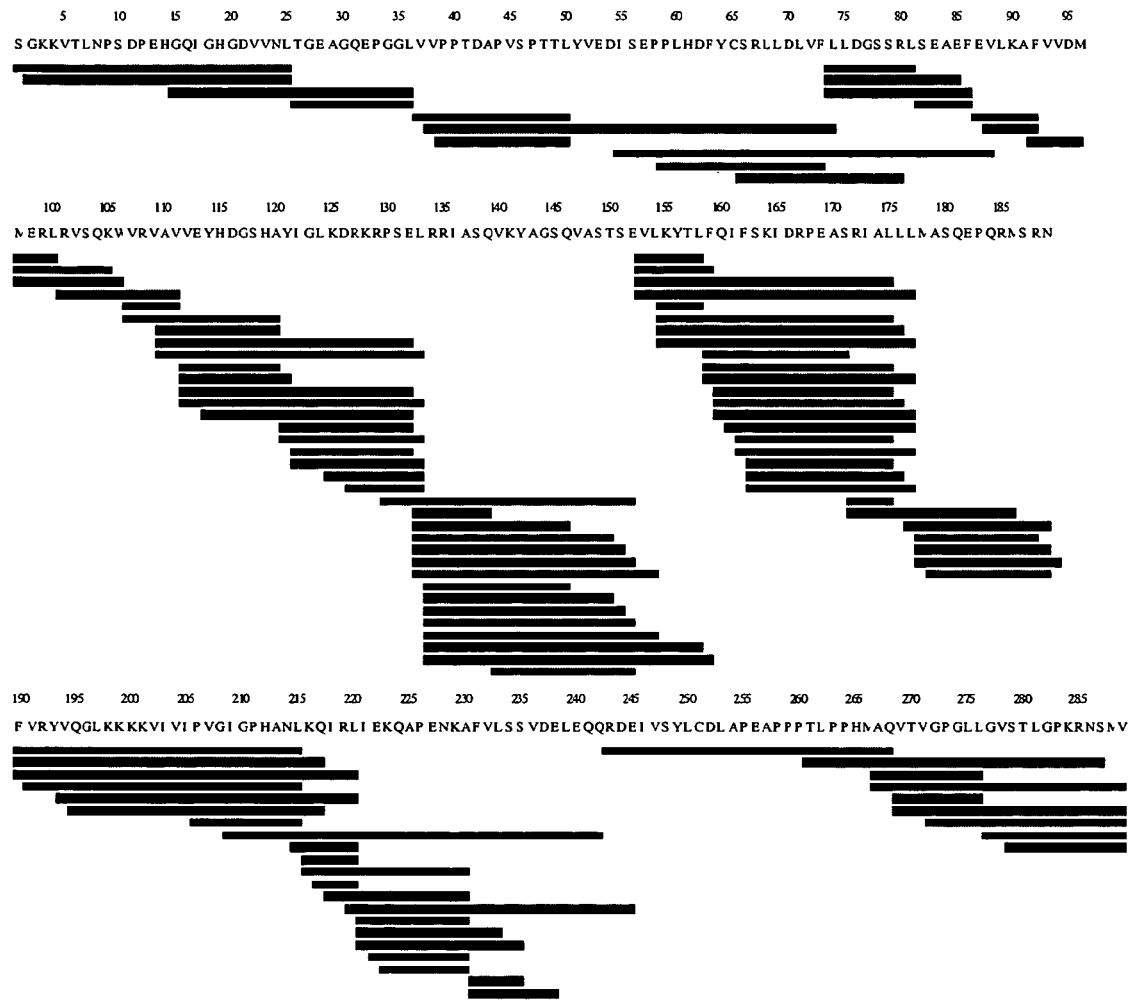
FIG. 8 presents the fragmentation map obtained for a human von Willebrand Factor construct (denatured in 0.5 M GuHCl) employing a 40 second digestion on a pepsin column. In this study it was necessary to simultaneously reduce an internal disulfide bond by mixing TCEP (1.0 M final concentration) with the denaturant (SEQ ID NO: 2).

FIG. 8 presents the fragmentation map obtained for a human von Willebrand Factor construct (denatured in 0.5 M GuHCl) employing a 40 second digestion on a pepsin column. In this study it was found useful to simultaneously reduce an internal disulfide bond by mixing TCEP (1.0 M final concentration) with the denaturant.

It is to be emphasized that the speed of generation (typically in 30 seconds) and the yield and extent of the highly overlapping fragmentation seen using the high resolution hydrogen exchange methods presented herein is unprecedented in the previously disclosed art, and was unanticipated until these recent results. There was no expectation that the art of modulating endopeptidase activity-both in terms of producing the needed varied fragmentation and yield could be enhanced enough to be useful by itself for high resolution localization of label. Heavy hydrogen label is quickly lost from proteolytic fragments during analysis, even under quench conditions: thus, all steps of analysis should be performed as quickly as possible, including protease digestion. The methods developed and available prior to 1997 required pepsin degradation durations that were already at the upper limits of acceptable times (approximately 10 minutes). For example in U.S. Pat. No. 6,291,189, it is stated that: "In a preferred embodiment, pepsin is used, preferably at a concentration of 10 mg/ml pepsin at 0° C., pH 2.7 for 5-30 minutes, preferably 10 minutes." It was therefore unanticipated that more extensive digestions could be obtained with pepsin with or without other endoproteinases given the time constraints of amide hydrogen exchange study.

Figure 9:
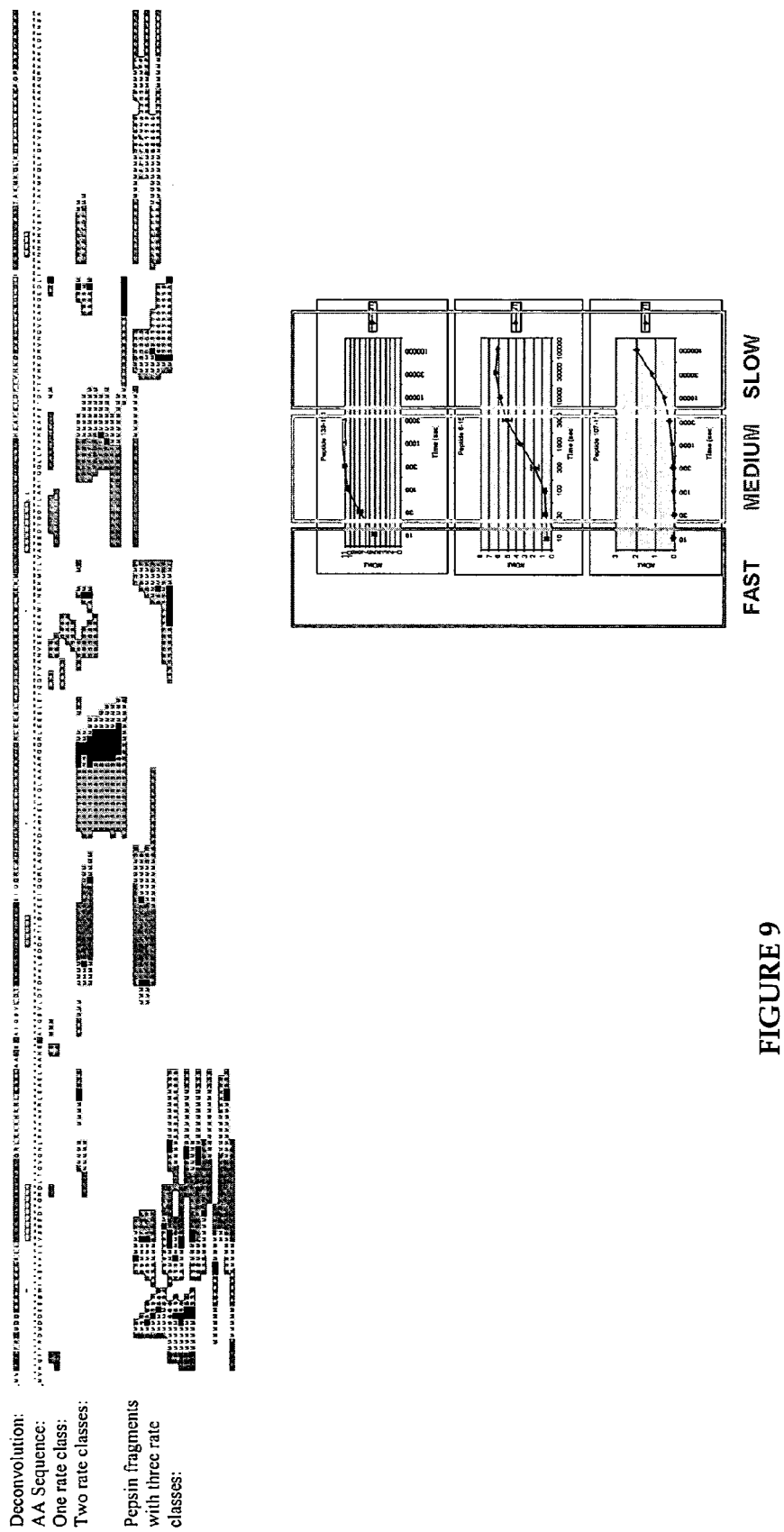
FIG. 9 presents the results of a deconvolution of fragmentation data obtained from chicken brain spectrin analyzed by high resolution hydrogen exchange. The deuterium content of the 113 useful peptides resulting from such fragmentation was determined from the raw mass spectroscopy data. Plots of deuterium buildup versus time were constructed for each peptide, and the number of amides exchanging in arbitrary "fast, medium and slow" classes (light, medium, and dark grey colors respectively in the figure) determined for each peptide. An initial map of rates versus amino acid sequence was then constructed from this information, employing a strategy in which "pieces" (fragments) with uniform rate class (color), were first placed in register, and subsequent placement of more complexly colored pieces (two color then three color), and performed in a manner that required that the several "colors" in these peptides be reconciled vertically to conform with color placement of the preceding pieces. The average color (rate class) at each amide position was then determined and used to construct the initial map. Unmeasurable amide hydrogens (approximately 10% of the total amides in the 113 fragments, unmeasured either because of errors incurred because of the approximate (average) back-exchange calculation method employed, or because the very slowest exchanging amides were not measured in this experiment) were then fit to the provisional map in a manner that minimized deviation from said map, and a final map constructed by averaging this final placement of "pieces" (SEQ ID NOs: 3 and 4).

Accordingly, the methods of the present invention analyze endopeptidase fragments that are generated by cleaving the labeled protein with an endopeptidase selected from the group consisting of a serine endopeptidase, a cysteine endopeptidase, an aspartic endopeptidase, a metalloendopeptidase, and a threonine endopeptidase (a classification of endopeptidases by catalytic type is available on the world wide web at the URL "chem.qmul.ac.uk/iubmb/enzyme/EC34"; by the Nomenclature Committee of the International Union of Biochemistry and Molecular Biology). Presently preferred endopeptidases include pepsin, newlase and acid tolerant *Aspergillus* proteases such as *Aspergillus* protease XIII. FIGS. 8 and 9 demonstrate the distinctive fragmentation patterns that can be obtained with each of the endoproteinases employed in methods of the present invention. It has further been found that the fragmentation patterns resulting from simultaneous, and/or sequential proteolysis by combinations of these enzymes are additive in their effect on fragmentation. Therefore, more than one endopeptidase may be used in combination. Optimally, endopeptidase fragments are generated at a pH of about 1.8-3.4, preferably 2-3, more preferably in the range of about 2.1-2.3 or 2.5-3.0.

In preferred embodiments, the endopeptidase may be coupled to a perfusive support material to facilitate manipulation of digestions, as an alternative to liquid phase digestions. This allows the reuse of endopeptidase materials and separates the enzyme from the fragments for further analysis. Exemplary perfusive support matrices include Poros 20 media, wherein digestion of the labeled protein is accomplished by contacting a solution of the labeled protein with said matrix, followed by elution of generated fragments from the matrix. With the use of the solid support, sample digestion under slowed exchange conditions can be performed that results in no detectable endoproteinase autodigestive fragments being released into the digestion product, i.e., the population of labeled protein fragments. Furthermore, the endoproteinases remain fully active and available for subsequent repeated use as a digestive medium for additional samples.

In accordance with the present invention, it has been discovered herein that the judicious admixture of denaturants with substrate protein results in the ability to greatly promote and "tune" substrate fragmentation. Unfortunately, these same denaturants retard and/or inhibit the activity of the enzymes unless denaturants are partially removed prior to proteolysis. However their removal allows the substrates to re-fold, negating the benefit of the denaturant. Gradual manual dilution of the substrate-enzyme-denaturant mixture allowed an initially slow proteolysis to proceed. With subsequent dilution, partially degraded substrate is unable to refold; and because of denaturant dilution, protease activity increases, further fragmenting the initial large substrate fragments. Success in this method required multiple manual additions of reagents, denaturants, and timed addition of diluents, all very labor intensive. The improved methods of the present invention use solid-state enzymes on perfusive supports and column chromatography, enabling samples to be applied to the column already mixed with denaturant, and the necessary dilution of denaturant automatically occurs as the substrate slug passes down the column, now progressively diluted with the fluid in the column void volume as proteolysis proceeds. This results in tremendous labor savings, and is readily automated. There is thus an unanticipated ease and simplification of use of the necessary denaturants when solid phase proteases are employed.

A variety of acid-reactive endoproteinases can be covalently coupled to any of a number of available support matrices including, for example, cross-linked dextran, cross-linked agarose, as well as more specialized supports suitable for modern HPLC chromatography, preferably the Poros line of perfusive support materials supplied by Perceptive Biosystems, such as "20-AL" and the like. These latter supports are particularly advantageous for invention methods as they allow rapid interaction of substrate with bound peptidases. The coupling of endoproteinases to matrices can be achieved by any of a number of well-known chemistries capable of effecting such couplings, including, for example, aldehyde-mediated (sodium cyanoborohydride-stabilized Schiff base), carbodiimide, and cyanogen bromide-activated couplings. Conditions, including pH, conducive to the continued stability of particular peptidases may optionally be employed, and could readily be implemented by one of skill in the art.

An exemplary preparation of coupled endopeptidase is as follows. The endopeptidase is obtained as a lyophilized powder, reconstituted with distilled water, and dialyzed against a coupling buffer containing 50 mM citrate (pH 4.4). The peptidase is then coupled to Perceptive Biosystems Poros media 20-AL following the manufacturer's recommended coupling procedures, including "salting out" with high sodium sulfate concentrations. Couplings can be performed at a ratio of 5 to 30 mg of peptidase per ml of settled 20-AL matrix, preferably 30 mg/ml. The coupled matrix can then be stored in the presence of sodium azide to minimize bacterial contamination.

While any of a number of batchwise or column chromatographic approaches might be employed to effect matrix-bound endopeptidase digestion of labeled protein under slowed exchange conditions, the following approach has been found to work well and to be preferable. A stainless steel column (length 2 cm, width 2.2 mm, internal volume approximately 66 microliters) was packed with endoproteinase-derivatized 20-AL support coupled with protein at 30 mg/ml) and flow established with a solvent consisting of 0.5% formic acid (for pepsin, newlase, or *Aspergillus* protease XIII), said column being operated at 0° C. Care must be taken to employ buffers with a pH compatible with rapid peptidase action: buffers with a pH of 2.7-3.0 (room temperature measurement) work well. An aliquot of labeled protein to be fragmented was contacted with the column matrix typically in a volume of 10-300 microliters, preferably 100 microliters, and the sample allowed to reside on the column for a time determined (by preliminary titration studies) to result in the desired degree of fragmentation. It has been surprisingly found herein that digestion times of 13 seconds to 5 minutes, preferably less than a minute, more preferably, less than 40 seconds to be optimal. Prior knowledge of endopeptidase digestion suggested that digestion times of greater than 10 minutes would be required to produce sufficient fragmentation. The sample was then flushed from the column onto either an analytical reverse phase HPLC column for subsequent separation and analysis of the peptide fragments, or directly without additional purification or chromatography onto a mass spectrometer for analysis. During this analysis period, the column is flushed (with the effluent going to waste) with an excess of solvent to remove any peptide or subfragments which nonspecifically adhere or are otherwise retained in the matrix, thereby preparing the column for a repeated use. Such washing buffers can be any of a wide variety of buffers including the buffers used for digestion. The column-washing step (between each sample digestion) is preferable but not absolutely required for success.

In an additional embodiment, a column containing one of these solid state proteases can be used to further digest peptides on-line as they each independently exit the reversed phase (RP) HPLC column during gradient elution. This approach has the considerable advantage of producing a much less complex mixture of peptides to analyze than when two enzymes act on the substrate before RP-HPLC. To use these enzymes in this post-chromatography manner, it may be useful to reduce the acetonitrile concentration in the effluent stream prior to passage over the protease column, as acetonitrile can reversibly (and irreversibly) inhibit these enzymes.

In addition, disulfide bonds, if present in the protein to be digested, can also interfere with analysis. Disulfide bonds can hold the protein in a folded state where only a relatively small number of peptide bonds are exposed to proteolytic attack. Even if some peptide bonds are cleaved, failing to disrupt the disulfide bonds would reduce resolution of the peptide fragments still joined to each other by the disulfide bond; instead of being separated, they would remain together. This would reduce the resolution by at least a factor of two (possibly more, depending on the relationship of disulfide bond topology to peptide cleavage sites).

In one embodiment, water soluble phosphines, for example, Tris (2-carboxyethyl) phosphine (TCEP) may be used to disrupt a protein's disulfide bonds under "slow hydrogen exchange" conditions. This allows much more effective fragmentation of large proteins which contain disulfide bonds without causing label to be lost from the protein or its proteolytic fragments (as would be the case with conventional disulfide reduction techniques which must be performed at pHs which are very unfavorable for preservation of label).

High resolution localization of label-bearing amides with the use of endoproteinases requires the proteolytic generation of numerous sequence-overlapped fragments under conditions which allow the label to remain in place (e.g., 0° C., pH 2.2). The ability of any protease to fragment a protein or peptide is limited by the accessibility of the protease to susceptible peptide bonds. While denaturants such as acidic pH, urea, detergents, and organic co-solvents can partially denature proteins and expose many otherwise structurally shielded peptide bonds, pre-existing disulfide bonds within a protein can prevent sufficient denaturation with these agents alone. In conventional protein structural studies, disulfides are usually cleaved by reduction with 2-mercaptoethanol, dithiothreitol, and other reductants which unfortunately require a pH greater than 6 and elevated temperature for sufficient activity, and are therefore not useful for the reduction of disulfides at pH 2.7 or below. For this reason, the hydrogen exchange art has not attempted any form of disulfide bond disruption, has for the most part been restricted to the study of proteins without intrinsic disulfide bonds, and has accepted the low resolution achievable without disulfide bond disruption.

It has been recognized and demonstrated herein that acid-reactive phosphines such as Tris (2-carboxyethyl) phosphine (TCEP) can be used to disrupt disulfides under the acidic pH and low temperature constraints required for hydrogen exchange analysis. These manipulations disrupt these associations and at the same time continue to produce a markedly slowed proton exchange rate for peptide amide protons.

Denatured (with or without reduction) labeled protein is then passed over a column composed of insoluble (solid state) pepsin, whereby during the course of the passage of such denatured or denatured and reduced binding protein through the column, it is substantially completely fragmented by the pepsin to peptides of size range 2-20 amino acids at 0° C. and at pH 2.7. The effluent from this column (containing proteolytically-generated fragments of labeled protein) is directly and immediately applied to the chromatographic procedure employed to separate and analyze protein fragments, preferably analytical reverse-phase HPLC chromatography and/or mass spectrometry.

In preferred embodiments, proteins containing disulfide bonds may be first physically attached to solid support matrices, and then contacted with solutions containing TCEP at acidic pH and low temperature for more rapid reactions than are possible in solution. In this preferred embodiment, with all steps performed at 5-0° C., preferably 0° C., the protein in aqueous solution, with or without prior denaturation and under a wide variety of pH conditions (pH 2.0-9.0) is first contacted with a particulate silica-based reverse-phase support material or matrix typically used to pack HPLC columns, including C4 and C18 reversed phase silica supports, thereby attaching the protein to the surface of such material. Unbound binding protein may then optionally be washed off the support matrix with typical aqueous HPLC solvents, (0.1% trifluoroacetic acid, (TFA) or 0.1-0.5% formic acid in water, buffer A). An aliquot of a substantially aqueous buffer containing TCEP at a pH between 2.5 and 3.5, preferably 2.7 is then contacted with the protein that is attached to the support material and allowed to incubate with the attached protein near 0° C. and preferably for short periods of time (0.5-20 minutes, preferably 5 minutes) and then the TCEP-containing buffer removed from the support matrix by washing with buffer A, followed by elution of the reduced binding protein from the support matrix by contacting the support with eluting agents capable of disrupting the support-protein binding interaction, but also compatible with continued slow hydrogen exchange (pH 2.0-3.5; temperature 0-5° C.).

An example of this preferred embodiment to achieve disulfide reduction prior to pepsin fragmentation is as follows. Labeled protein is applied to a reverse phase silica-based C18 HPLC support matrix in a column (for example, Vydac silica-based C18, catalog #218TP54, or Phenominex silica-based C18 Jupiter 00B4053-B-J) that has been pre-equilibrated with HPLC solvent A (0.1% TFA or 0.1-0.5% formic acid at 0-5° C. After substantial binding of the lysozyme has occurred (usually within seconds), additional buffer A is passed through the column to remove small quantities of unattached binding protein. A solution containing TCEP (50-200 micrometers of TCEP (0.05-2.0 M in water at a pH of 2.5-3.5, preferably 3.0) is then applied to the column in a manner that results in its saturation of the portion of the column to which the binding protein has been previously attached. Flow of solvent on the support is then stopped to allow incubation of the TCEP solution with the support matrix-attached binding protein. At the end of this incubation time (variously 0.5 minutes-20 minutes, preferably 5 minutes) flow of solvent A is resumed, resulting in the clearance and washing of the TCEP solution from the support matrix. This is followed by application of an amount of solvent B (20% water, 80% acetonitrile, 0.1% TFA) sufficient to release the binding protein from the support (typically 30-50% solvent B in solvent A). This eluted and reduced protein is then passed over a pepsin column to effect its fragmentation under slowed exchange conditions. The protein fragments resulting from the action of the pepsin column on the reduced protein are then contacted with another analytical HPLC column, preferably a reverse phase HPLC support, and the fragments sequentially eluted from the support with a gradient of solvent B in solvent A.

An example of an alternative preferred embodiment to achieve disulfide reduction after pepsin fragmentation is as follows. This alternative approach is to first denature the protein under slow exchange conditions, pass it over a pepsin column to effect fragmentation, apply the resulting fragments to a HPLC support matrix, effect reduction of the support-bound peptide fragments by contacting them with the aforementioned TCEP solution, followed by sufficient incubation at 0° C., finally followed by elution of the reduced fragments from the column with increasing concentrations of solvent B. The advantage of this second alternative method is that an entire HPLC support matrix attachment-detachment step is avoided, resulting in a simplification of the manipulations and equipment required for the procedure, as well as savings in elapsed time. This approach is not probable when a particular protein requires substantial prior reduction of disulfides to become substantially susceptible to the digestive actions of pepsin. Certain proteins are sufficiently stabilized by their contained disulfide bonds that they may not become substantially susceptible to pepsin even in the presence of strong denaturants. In such cases it will be preferable to apply the first method of reduction (above), where the protein is first reduced "on column", eluted, fragmented on the pepsin column, and the fragments then optionally applied to an additional column matrix to effect separation from each other.

Additionally, it has been found herein that the simultaneous use of denaturants and reductants (TCEP) results in synergistic enhancement of both protein denaturation and reduction, not seen when employed separately, or even sequentially.

Deconvolution of Endopeptidase-Generated Fragments in Methods Employing Improved Proteolysis Fragmentation Mass spectroscopy has become a standard technology by which the amino acid sequence of proteolytically generated peptides can be rapidly determined. It is commonly used to study peptides which contain amino acids which have been deuterated at carbon-hydrogen positions, and thereby determine the precise location of the deuterated amino acid within the peptide's primary sequence. This is possible because mass spectroscopic techniques can detect the slight increase in a particular amino acid's molecular weight due to the heavier mass of deuterium. McCloskey (*Meth. Enzymol.* 193:329-338, 1990) discloses use of deuterium exchange of proteins to study conformational changes by mass spectrometry. The methods of the present invention include measuring the mass of endopeptidase-generated fragments to determine the presence or absence, and/or the quantity of deuterium on the endopeptidase-generated fragments. Preferably, mass spectrometry is used for mass determination of these peptide fragments. This allows determination of the quantity of labeled peptide amides on any peptide fragment.

According to the methods of the present invention, proteolytically generated fragments of protein functionally labeled with deuterium may be identified, isolated, and then subjected to mass spectroscopy under conditions in which the deuterium remains in place on the functionally labeled peptide amides. Standard peptide sequence analysis mass spectroscopy can be performed under conditions which minimize peptide amide proton exchange: samples can be maintained at 4° C. to 0° C. with the use of a refrigerated sample introduction probe; samples can be introduced in buffers which range in pH between 1 and 3; and analyses are completed in a matter of minutes. MS ions may be made by MALDI (matrix-assisted laser desorption ionization) electrospray, fast atom bombardment (FAB), etc. Fragments are separated by mass by, e.g., magnetic sector, quadrupole, ion cyclotron, or time-of-flight methods. For MS methods generally, see Siuzdak, G., Mass Spectrometry for Biotechnology (Academic Press 1996).

Once the endopeptidase fragmentation data is acquired on functionally deuterated protein, it is then deconvoluted to determine the position of labeled peptide amides in an amino acid specific manner. In general, the term "deconvoluted" as used herein refers to the mapping of deuterium quantity and location information obtained from the fragmentation data onto the amino acid sequence of the labeled protein to ascertain the location of labeled peptide amides, and optionally their rates of exchange. Deconvolution may comprise comparing the quantity and/or rate of exchange of isotope(s) on a plurality of endopeptidase-generated fragments with the quantity and rate of exchange of isotope(s) on at least one other endopeptidase fragment in the population of fragments generated, wherein said quantities are corrected for back-exchange in an amino acid sequence-specific manner. Labeled peptide amides can optionally be localized in an amino acid sequence-specific manner by measuring rates of off-exchange of functionally attached label under quenched conditions. The determination of the quantity and rate of exchange of peptide amide hydrogen(s) may be carried out contemporaneously with the generation of the population of endopeptidase-generated fragments.

Although several alternative methods for effecting such deconvolution may be available, at least one useful method has been implemented and demonstrated herein. FIG. 9 presents the results of such a deconvolution. A protein construct composed of a two repeat segment (16-17) of chicken brain spectrin was on-exchanged in deuterated buffer for varying times (10 to 100,000 seconds, at 22° C.). Samples were then exchange-quenched, in 0.5 M GuHCl, pH 2.2, and otherwise processed as shown in FIG. 6. The deuterium content of the 113 useful peptides resulting from such fragmentation was determined from the raw MS data, with corrections for back-exchange made employing the inexact "peptide average" method of Zhang and Smith (Zhang et al., *Prot. Sci.* 2:522-531,1993).

Plots of deuterium buildup versus time were constructed for each peptide, and the number of amides exchanging in arbitrary "fast, medium and slow" classes (light, medium, and dark grey shading respectively in the figure) determined for each peptide. An initial map of rates versus amino acid sequence was then constructed from this information, employing a strategy in which "pieces" (fragments) with uniform rate class (each class given a color), were first placed in register, and subsequent placement of more complexly colored pieces (two colors then three colors) performed in a manner that required that the several "colors" in these peptides be reconciled vertically to conform with the color placement of the preceding pieces. The average color (rate class) at each amide position was then determined and used to construct the initial map. Unmeasureable amide hydrogens (approximately 10% of the total amides in the 113 fragments, unmeasured either because of errors incurred because of the approximate (average) back-exchange calculation method employed, or because the very slowest exchanging amides were not measured in this experiment) were then fit to the provisional map in a manner that minimized deviation from said map, and a final map constructed by averaging this final placement of "pieces".

The choice of three rate classes was arbitrary, and done to simplify the "piece placement" work, which was done manually in this example. Assignment of amides in each peptide to each of 9 rate classes (9 time points were employed in this experiment) would considerably improve the resolution of the deconvolution, but is conveniently performed by automated (computational) means, and with incorporation of more precise back-exchange corrections as discussed below. Further fragmentation of this protein construct with pepsin plus Fungal protease XIII has resulted in a 50% increase in the number of spectrin fragments, which will preferably be deconvoluted through linear programming-mediated approaches.

The essential attributes of a preferred deconvolution algorithm for such high density, overlapping endopeptidase fragment data include that: (i) it takes as inputs the measurements of the quantity of label on the numerous overlapping endopeptidase-generated fragments correlated with their amino acid (aa) sequence; (ii) it more precisely corrects for back-exchange (that is, label lost subsequent to initiation of quench, during the analysis step) than the presently employed method that calculates an average correction factor for all amides in a peptide (Zhang et al., *Prot. Sci.* 2:522-531, 1993) and instead employs a correction that is sub-site-specific (specific for 1-5 contiguous amides, depending on the resolving power of the aggregate endopeptidase fragments available). This can be done both computationally (by reference to the Bai/Englander-algorithm; Bai et al., *Proteins: Struct. Funct. Genet.* 17:75-86, 1993) or alternatively experimentally by measuring back exchange, under quench conditions, of the substantially random coil fragments resulting from identical endoproteolysis of a fully (equilibrium) deuterated sample of the protein in a manner that allows the rate(s) of loss of deuterium to be measured over time for each resolvable sequence region. Either approach affords precise calculation of the label lost through back exchange from each peptide, and, by comparison, that lost in each aa segment that differs between aa sequence-overlapping peptides. Corrections for these losses are made for each peptide/aa overlap difference value; (iii) it compares the (corrected) label content of each peptide with the label content of all peptides with which it (or immediately adjoining peptides) share any part of aa sequence, said comparisons being performed in a manner which allows differences in label content to be assigned to regions of aa sequence difference, with the preferred algorithm seeking to fit deuterium location and quantity at each location in a manner that optimizes agreement between results obtained from the plurality of fragments; and (iv) it optionally makes use of measurements of off-exchange rates of label on quenched fragments, which, by reference to the above noted site-specific rate (under quench conditions) prediction or empirical determination from endoproteinase fragmentation data of equilibrium-deuterated protein) can be employed to further sublocalize label at regions unresolved by analysis of fragments alone at one quench condition duration.

Automation of Hydrogen Exchange Analyses

The high resolution hydrogen exchange methods of the present invention may be performed using an automated procedure. Automation may be employed to perform isotope-exchange labeling of proteins as well as subsequent proteolysis and MS-based localization procedures. The use of such automation allows one to manipulate proteolysis conditions under quench conditions, largely by employing solid-state chemistries as described above. The following discussion refers to modules as designated in the exemplary deuterium exchange-mass spectrometry (DXMS) apparatus illustrated in FIG. 2.

The fluidics of the DXMS apparatus contains a number of pumps, high pressure switching valves and electric actuators, along with connecting tubing, mixing tees, and one way flow check valves and that direct the admixture of reagents and their flow over the several small stainless steel columns containing a variety of proteins and enzymes coupled to perfusive (Poros 20) support material.

While there is a standard configuration of these various components, the pattern of the several elements can be quickly changed to suit particular experimental requirements. DXMS fluidics contains a "cryogenic autosampler" module (A), a "functional deuteration" or sample preparation module (B) used for automated batched processing of manually prepared samples, and a "endopeptidase proteolysis" module (C). Precise temperature control is achieved by enclosing the valves, columns, and connecting plumbing of modules A, B, and C in a high thermal-capacity refrigerator kept at about 3.8° C. (the freezing point of deuterated water), and components that have no contact with pure deuterated water are immersed in melting (regular) ice.

Module A, the "cryogenic autosampler" allows a sample set (in the range of about 10-50 samples) to be prepared manually in autosampler vials, quenched, denatured, and samples frozen at −80° C., conditions under which loss of deuterium label in the prepared samples is negligible over weeks. This allows a large number of deuterated samples to be manually prepared, and then stored away for subsequent progressive proteolysis. This capability also allows samples to be manually prepared at a distant site, and then shipped frozen to the DXMS facility for later automated analysis. This module contains a highly modified Spectraphysics AS3000® autosampler, partially under external PC control, in which the standard pre-injection sample preparation features of the autosampler are used to heat and melt a frozen sample rapidly and under precise temperature control. Under computerized control, the autosampler's mechanical arm lifts the desired sample from the −80° C. sample well, and places it in the autosampler heater/mixer/vortexer which rapidly melts the sample at 0-5° C. The liquified sample is then automatically injected onto the HPLC column.

Optional modifications to a such a standard autosampler may include: modification of the sample basin to provide an insulated area in which dry ice can be placed, resulting in chilling of the remaining areas of the sample rack to −50 to −80° C.; placement of the autosampler within a 0-5° C. refrigerator, and "stand-off" placement of the sample preparation and sample injection syringe assemblies of the autosampler outside the refrigerator, but with otherwise nominal plumbing and electrical connection to the autosampler. An external personal computer (PC) (running Procom, and a dedicated Procrom script "Asset1"), delivers certain settings to firmware within the autosampler, allowing: (i) a much shortened subsequent post-melting dwell time of samples in the chilled basin, avoiding re-freezing of sample prior to injection; and (ii) allowing its heater/mixer to regulate desired temperatures when they are less than the default minimum temperature of 30° C.

The "sample preparation" module (B), automatically performs the "functional deuteration" or sample preparation manipulations, quench, and denaturation in large part through use of the solid-state inventions as described earlier herein, for example, using a protein conjugated to solid phase beads. Several components of this module will benefit from the microfluidics inventions also described earlier.

Typically, deuterated samples are manually prepared (both at 0° C., and at room temperature) by diluting 1 μL of protein stock solution with 19 μL of deuterated buffer (150 mM NaCl, 10 mM HEPES, pD 7.4), followed by "on-exchange" incubation for varying times (10 sec, 30 sec, 100 sec, 300 sec, 1000 sec, 3000 sec) prior to quenching in 30 μL of 0.5% formic acid, 2 M GuHCl, 0° C. These functionally deuterated samples are then subjected to DXMS processing, along with control samples of undeuterated and fully deuterated protein (incubated in 0.5% formic acid in 95% $D_2O$ for 24 hours at room temperature). The centroids of probe peptide isotopic envelopes are then measured using appropriate software. In order to obtain the deuteration levels of each peptide corrected to the values after "on-exchange" incubation, but before DXMS analysis, the corrections for back-exchange are made employing the methods of Zhang and Smith as previously described.

Regardless of the manner of sample preparation, quenched samples are then automatically directed to the "proteolysis" module (for methods employing progressive proteolysis fragmentation), or alternatively the "endopeptidase proteolysis" module (C) (for methods employing improved proteolysis fragmentation), in which proteolysis is accomplished using a battery of solid-state protease columns, variously pepsin, fungal protease XIII, newlase, etc. as desired, with the resulting peptide fragments being collected on a small reversed-phase HPLC column, with or without the use of a small c18 collecting pre-column. This column(s) is then acetonitrile gradient-eluted, with optional additional post-LC on-line proteolysis. The effluent is then directed to the electrospray head of the mass spectrometer (a Finnegan ion trap or a Micromass Q-TOF) which protrudes into a hole drilled in the side of the refrigerator. Several components of this module lend themselves to microfluidic devices as described earlier.

In a preferred embodiment, the proteolysis module contains four high pressure valves (Rheodyne 7010); with valve 1 bearing a 100 μL sample loop; valve 2 bearing a column (66 μl bed volume) packed with porcine pepsin coupled to perfusive HPLC support material (Upchurch Scientific 2 mm×2 cm analytical guard column; catalog no. C.130B; porcine pepsin, Sigma catalog no. p6887, coupled to Poros 20 μL media at 40 mg/mL, in 50 mM sodium citrate, pH 4.5, and packed at 9 mL/min according to manufacturer's instructions); valve 3 bearing a C18 microbore (1 mm×5 cm) reversed phase HPLC column (Vydac catalog no. 218MS5105), and valve 4 connected to the electrospray head of a mass spectrometer. Inline filters (0.05 μm, Upchurch catalog no. A.430) are placed on each side of the pepsin column, and just before the C18 column (Vydac prefilter, catalog no. CPF 10) to minimize column fouling and carryover from aggregated material.

In this configuration, four HPLC pumps (Shimadzu LC-10AD, operated by a Shimadzu SCL-10A pump controller) supplied solvents to the valves; with pumps C and D providing 0.05% aqueous TFA to valve 1 and valve 2 respectively; pumps A (0.05% aqueous TFA) and B (80% acetonitrile, 20% water, 0.01% TFA) are connected through a microvolume mixing tee (Upchurch catalog no. P.775) to provide valve 3 with the C18 column-eluting gradient. All valves are connected to Two-Position Electrical Actuators (Tar Designs Inc.).

A typical sample is processed as follows: a 20 μL of hydrogen exchanged protein solution is quenched by shifting to pH 2.2-2.5, 0° C. with a 30 μL of quenching stock solution chilled on ice. The quenched solution is immediately pulled into the sample loading loop of valve 1, and then the computer program (see below) started. Pump C flow (0.05% TFA at 200 μL/min) pushes the sample out of injection loop onto the C18 HPLC column via the solid-state pepsin column at valve 2 (digestion duration of about 26 seconds). After two minutes of pump C solvent flow, the C18 column is gradient-eluted by pumps A and B (linear gradient from 10 to 50% B over 10 minutes; 50 μL/min; pumps A, 0.05% TFA; pump B, 80% acetonitrile, 20% water, 0.01% TFA), with effluent directed to the mass spectrometer. During data acquisition, pump D (aqueous 0.05% TFA 1 mL/min, 10 minutes) back-flushes the pepsin column to remove retained digestion products.

The timing and sequence of operation of the foregoing DXMS fluidics may be controlled by a personal computer running a highly flexible program in which sequential commands to targeted solid state relays can be specified, as well as variably timed delays between commands, as illustrated in the "DXMS Data Acquisition Control Module" (D). Certain command lines may access an array matrix of on- and off-exchange times, and the entire sequence of commands may be set to recycle, accessing a different element of the array with each cycle executed. Certain command lines may be set to receive "go" input signals from peripherals, to allow for peripheral-control of cycle progression. A library of command sequences may be prepared, as well as a library of on/off time arrays. An exemplary protein machine program can be configured to execute a supersequence of command sequence-array pairs.

An exemplary protein machine program (written in LabView I, National Instruments, Inc) controls the state(s) of a panel of solid-state relays on backplanes (SC-206X series of optically isolated and electromechanical relay boards, National Instruments, Inc.) with interface provided by digital input/output boards (model no. PCI-DIO-96 and PCI-6503, with NI-DAQ software, all from National Instruments, Inc.). The solid-state relays in turn exert control (contact closure or TTL) over pumps, valve actuators, and mass spectrometer data acquisition. Each of these peripherals are in turn locally programmed to perform appropriate autonomous operations when triggered, and then to return to their initial conditions. The autosampler and HPLC column pump controller are independently configured to deliver a "proceed through delay" command to the Digital I/O board as to insure synchronization between their subroutines and the overall command sequence.

In order to optimize or "tune" endopeptidase proteolysis, preliminary proteolytic "tuning" studies are performed to establish the fragmentation conditions (compatible with slowed exchange) optimal for peptide generation from the target polypeptide. Two major parameters that are often optimized are the concentration of GuHCl in quenching buffer and the pump C flow rate over the pepsin column. Typically, a 1 ml stock solution of protein (10 mg/ml, pH 7.0) is diluted with 19 mL of water and then quenched with 30 mL of 0.5% formic acid containing various concentrations of GuHCl (0-6.4 M). The quenched sample is then pulled into the sample loading loop, and the DXMS program sequence triggered immediately after sample loading. The flow over the pepsin column is varied (100 µL/min-300 µL/min) to adjust the duration of proteolytic digestion.

In order to quickly identify pepsin generated peptides for each digestion condition employed, spectral data is preferably acquired in particular modes, for example designated herein as "triple play" and "standard double play" modes, which have been empirically tuned to optimize the number of different parent ions upon which MS2 is performed. This data is then analyzed by appropriate software.

Triple play contains three sequentially executed scan events; first scan, MS1 across 200-2000 m/z; second scan, selective high resolution "zoom scan" on most prevalent peptide ion in preceding MS1 scan, with dynamic exclusion of parents previously selected; and third scan, MS2 on the same parent ion as the preceding zoom scan. The triple play data set or double play data set is then analyzed employing the Sequest software program (Finnigan Inc.) set to interrogate a library consisting solely of the amino acid sequence of the protein of interest to identify the sequence of the dynamically selected parent peptide ions.

This tentative peptide identification is verified by visual confirmation of the parent ion charge state presumed by the Sequest program for each peptide sequence assignment it made. This set of peptides is then further examined to determine if the "quality" of the measured isotopic envelope of peptides was sufficient (adequate ion statistics, absence of peptides with overlapping m/z) to allow accurate measurement of the geometric centroid of isotopic envelopes on deuterated samples.

According to an additional aspect of the present invention, it may be useful to perform in vivo analysis of a polypeptide of interest, for example, in situ analysis of protein-binding partner interactions. In such applications, the protein, while present in its native environment as a component of an intact living cell, or as a component of a cellular secretion such as blood plasma, is on-exchanged by incubating cells or plasma in physiologic buffers supplemented with tritiated or deuterated water. Optionally, the binding partner is then added, allowed to complex to the cell or plasma-associated protein, and then off-exchange initiated by returning the cell or plasma to physiologic conditions free of tritiated or deuterated water. During the off-exchange period (hours to days) the formed protein or complex is isolated from the cell or plasma by any purification procedure which allows the protein or complex to remain continuously intact. At the end of the appropriate off-exchange period, fragmentation and analysis of purified protein or complex proceeds as above. This analytic method is especially appropriate for proteins which lose substantial activity as a result of purification, as binding sites may be labeled prior to purification.

According to another aspect of the present invention, binding site analysis may be performed using indirect hydrogen exchange. In the methods described above, the entire surface of the protein is labeled initially, and label is then removed from those surfaces which remain solvent exposed after formation of the complex of the binding protein and its binding partner. The binding site of the protein is occluded by the binding partner, and label is therefore retained at this site.

When the complex is formed, the binding protein may undergo changes in conformation (allosteric changes) at other sites, too. If these changes result in segments of the protein being buried which, previously, were on the surface, those segments will likewise retain label.

It is possible to distinguish binding site residues from residues protected from "off-exchange" by allosteric effects. In essence, the binding partner, rather than the binding protein, is labeled initially. The binding protein is labeled indirectly as a result of transfer of label from the binding partner to the binding protein. Such transfer will occur principally at the binding surface.

This procedure will functionally label receptor protein amides if they are slowed by complex formation and are also in intimate contact with the binding partner in the complexed state. Receptor protein amides that are slowed because of complex formation-induced allosteric changes in regions of the protein which are not near the protein-binding partner interaction surface will not be labeled. This procedure may be performed as follows. First, binding partner is added to labeled water (preferably of high specific activity) to initiate exchange labeling of the binding partner.

After sufficient labeling is achieved, binding partner is then separated from the excess of solvent isotope under conditions which produce minimal loss of label from the binding partner. This can be accomplished, for example, by shifting the buffer conditions to those of slowed exchange (0° C., acidic pH) followed by G-25 spin column separation of the binding partner into isotope-free buffer, or by employing stopped-flow techniques in which the on-exchange mixture is rapidly diluted with large volumes of isotope free buffer.

The labeled binding partner, now essentially free of excess solvent isotope, is added to receptor protein and conditions adjusted to allow spontaneous reversible (equilibrium) complex formation to take place between the two.

The conditions of temperature and pH should also allow, and preferably maximize, the specific transfer of label from the labeled binding partner to amides on the binding protein's interaction surface with partner. Typically, the pH will be in the range of about 5-8 (conducive to ligand binding) and a temperature in the range of about 0-37° C. Initially, use of pH 7 and 22° C. is preferable, with the transfer being controlled by controlling the incubation time. A typical trial incubation time would be 24 hours. These conditions of pH, temperature and incubation time may of course be varied.

The complex is then incubated for periods of time sufficient to allow transfer of label from the labeled binding partner to the receptor protein. During this incubation period, label which has on-exchanged to regions of the binding partner that are distant from the receptor-binding partner interaction surface will leave the binding partner by exchange with solvent hydrogen and be rapidly and highly diluted in the large volume of solvent water, thereby preventing its efficient subsequent interaction with the binding protein. However, label that has been attached to binding partner amides present within the (newly formed) protein-binding partner interaction surface will be capable of exchanging off of the binding partner only during the brief intervals when the interaction surface is exposed to solvent water, i.e., when the complex is temporarily dissociated. When so dissociated and solvent exposed, a portion of tritium present on amides within the binding partner's interaction surface will leave the surface and for a brief time, remain within the proximity of the surface. Given the rapid (essentially diffusion limited) rebinding of binding protein and partner, much of the released tritium that (briefly) remains within the environs of the partner's binding surface will in part exchange with amides on the (future) interaction surface of the approaching binding protein molecule that subsequently binds to the binding partner. Once such binding occurs, the transferred label is again protected from exchange with solvent until the complex dissociates again. The result will be the progressive transfer of a portion of the label from the binding partner interaction surface to exchangeable amides on the cognate protein interaction surface.

Amides whose exchange rates are conformationally slowed each time complex formation occurs can also become labeled, but they will do so at a much slower rate than amides within the binding surface, as they are located more distant from the high concentration of label "released" at the interaction surface with each complex dissociation event. The efficiency of transfer is roughly inversely proportional to the cube of the distance between such conformational changes and the binding surface.

The binding protein-labeled binding partner complex incubation conditions are adjusted to optimize specific interaction surface amide tritium transfer (SISATT) for a articular binding protein-partner pair. SISATT is defined as the ratio of the amount of tritium (CPM) transferred from binding partner to binding protein peptide amides previously determined to undergo slowing of amide hydrogen exchange upon binding-protein partner complex formation divided by the total tritium (CPM) transferred from binding partner to all peptide amides in the binding protein.

After an incubation period that allows and preferably maximizes SISATT, the conditions of slow hydrogen exchange are restored, the complex is dissociated and the binding protein fragmented. Fragments of binding protein (as opposed to the initially labeled binding partner) that bear label are identified, and further characterized as previously described. Preferably, deuterium is used instead of tritium as the label. Deuterium has the advantage of allowing a much higher loading of label (since deuterium is much cheaper than tritium).

It is possible, also, to directly label the binding partner with deuterium and the binding protein with tritium. As a result, both the binding site and allosterically buried amides of the binding protein will be tritiated, but only binding site amides will be deuterated.

The indirect method is especially applicable to study of proteins which undergo substantial conformational changes after, or in the course of binding, such as insulin and its receptor.

According to further aspects of the present invention, after determining the binding sites of a binding protein or a binding partner, by the present methods (alone or in conjunction with other methods), the information may be exploited in the design of new diagnostic or therapeutic agents. Such agents may be fragments corresponding essentially to said binding sites (with suitable linkers to hold them in the proper spatial relationship if the binding site is discontinuous), or to peptidyl or non-peptidyl analogues thereof with similar or improved binding properties. Alternatively, they may be molecules designed to bind to said binding sites, which may, if desired, correspond to the paratope of the binding partner.

The diagnostic agents may further comprise a suitable label or support. The therapeutic agents may further comprise a carrier that enhances delivery or other improves the therapeutic effect.

The agents may present one or more epitopes, which may be the same or different, and which may correspond to epitopes of the same or different binding proteins or binding partners.

Alternative embodiments of the present invention are apparent to one of skill in the art. The following embodiments are intended to provide additional useful applications of the crystallography methods of the present invention.

According to another aspect of the present invention, there are provided methods of refining a crystallographic structure determination of a protein of interest, said methods comprising comparing an initial crystallographic structure determined using crystal(s) of said protein to at least one other crystallographic structure determined using crystal(s) of at least one modified form of said protein, wherein said modified form(s) of said protein is(are) obtained by identifying and deleting unstructured regions of said protein using hydrogen exchange analysis.

According to yet another aspect of the present invention, there are provided methods of crystallization of a protein of interest, said methods comprising comparing an initial hydrogen exchange stability map of said protein to at least one other hydrogen exchange stability map of at least one modified form of said protein, wherein said modified form(s) of said protein is(are) obtained by identifying and deleting unstructured regions of said protein, and subjecting to crystallization one or more modified form(s) of said protein exhibiting an improved hydrogen exchange stability map.

According to another aspect of the present invention, there are provided methods of crystallographic structure determination of a protein of interest, said methods comprising comparing an initial hydrogen exchange stability map of said protein to at least one other hydrogen exchange stability map of at least one modified form of said protein, wherein said modified form(s) of said protein is(are) obtained by identifying and deleting unstructured regions of said protein, and subjecting to crystallization and structure determination one or more modified form(s) of said protein exhibiting an improved hydrogen exchange stability map.

The stability map of a protein of interest is defined by structured and unstructured regions of the protein, based on information obtained by the hydrogen exchange analysis performed on the protein. In a comparative sense, an improved stability map or profile is present when the number of unstructured regions or residues is decreased as compared to the original protein. Optionally, the hydrogen exchange stability maps of modified or daughter forms of the protein are also compared to the parent or original protein to identify those modified forms that have an improved stability and have preserved the three-dimensional structure of the retained regions of the parent protein. FIG. 1 shows an exemplary use of comparative hydrogen exchange stability maps to identify and delete unstructured regions, in addition to selecting the best daughter constructs for further crystallographic structure determinations.

The invention will now be described in greater detail by reference to the following non-limiting examples.

EXAMPLE 1

DXMS Analysis used to Elucidate Phosphorylation-Driven Motions in the COOH-Terminal Src Kinase Csk A. Background.

The Src family of nonreceptor protein tyrosine kinases (nrPTKs) bind to receptor protein tyrosine kinases (PTKs) where they phosphorylate down-stream protein targets associated with discrete signaling pathways (Superti-Furga and Courtneidge, *Bioessays*, 17:321-330, 1995; Neet and Hunter, *Genes Cells* 1:147-169, 1996; and Tatosyan and Mizenina, *Biochemistry* 64:49-58, 2000). While the Src enzymes comprise a large subfamily of nrPTKs, all are regulated through a single nrPTK, Csk (COOH terminal Src kinase). Csk down-regulates kinase activity by phosphorylating a single tyrosine residue in the C-terminus of the Src enzymes (Okada et al., *J. Biol. Chem.* 266:24249-24252, 1991; and Bergman et al., *EMBO J.* 11:2919-2924, 1992). Owing to this premier regulatory function, Csk has direct effects on many biological functions including T cell activation, neuronal development, cytoskeletal organization, and cell cycle control (Inomata et al., *J. Biochem.* 116:386-392,1994; Latour and Veillette, *Curr. Opin. Immunol.* 13:299-306, 2001; Taylor and Shalloway, *Bioessays* 18:9-11, 1996; and Zenner et al., *Bioessays* 17:967-975,1995). The general significance of Csk is also evident in the lethality of gene knockouts in mice (Hamaguchi et al., *Biochem. Biophys. Res. Commun.* 224:172-179,1996). Csk contains three structural components essential for in vivo function: a tyrosine kinase domain, an SH2 domain, and an SH3 domain. The structure of the kinase domain, solved by x-ray diffraction, adopts a standard kinase fold with typical nucleotide and substrate binding lobes (Lamers et al., *J. Mol. Biol.* 285:713-715,1999). Unlike Src family nrPTKs, Csk is not upregulated through activation loop phosphorylation. The x-ray structures for c-Src, illustrate that the C-terminus is phosphorylated and interacts tightly with the SH2 domain (Sicheri et al., *Nature* 385:602-609, 1997; Williams et al., *J. Mol. Biol.* 274:757-775,1997; and Xu et al., *Nature* 385: 595-602,1997). In Csk, no such interaction is possible owing to the absence of a phosphorylatable sequence in the C-terminus. As revealed by x-ray diffractions studies, this generates a unique domain organization where the SH2 domain interacts with the small lobe of the kinase core in Csk rather than the large lobe as in c-Src (Ogawa et al., *J. Biol. Chem.* 277:14351-14354, 2002).

Understanding the conformational nature of protein kinases in solution is important for evaluating function since it has been shown that slow structural movements can limit substrate phosphorylation. The first pre-steady-state kinetic studies applied to a protein kinase, cAMP-dependent protein kinase (PKA), revealed that slow conformational changes associated with nucleotide binding and release limit catalytic cycling (Grant and Adams, *Biochemistry* 35:2022-2029, 1996; Shaffer and Adams, *Biochemistry* 38:12072-12079, 1999; and Shaffer and Adams, *Biochemistry* 38:5572-5581, 1999). Since these early investigations, two other protein kinases have been studied using fast mixing kinetic techniques. While the tyrosine kinases Her-2 and Csk rapidly phosphorylate substrates in the active site, rate-limiting events in the catalytic cycle are associated with slow conformational changes linked to ADP release (Shaffer and Adams, *Biochemistry* 40:11149-11155, 2001; and Jan et al., *Biochemistry* 39:9786-9803, 2000). Although more kinetic investigations would aid a broad assessment of function, the detailed investigations into these three protein kinases reveal a common motif for activity regulation. Once ATP and the substrate are appropriately oriented in the active site, phosphoryl transfer occurs with little impediment. In contrast, the regeneration of this active complex occurs partly through slow conformational changes that appear to be linked to ADP release.

Amide hydrogen exchange techniques have proven to be increasingly powerful tools by which protein dynamics, structure and function can be probed. Deuterium exchange methodologies coupled with either MALDI or Electrospray (ESI) Mass Spectrometry, presently provide one of the most effective approaches to study proteins larger than 30 kDa in size. Proteolytic and/or collision-induced dissociation fragmentation methods allow exchange behavior to be mapped to subregions of the protein. In a previous study using such techniques, it was demonstrated that ADP binding induces long-range structural changes in the catalytic subunit of PKA (Andersen et al., *J. Biol. Chem.* 276:14202-14211, 20010. Two of these regions encompass critical loops in the active site, as expected, whereas two other regions are distally located. These regions encompass the C-terminus and helix αC. Based on crystallographic evidence, the latter secondary structural element is known to move in phosphorylation- and subunit-dependent manners in several other protein kinases Jeffrey et al., *Nature* 376:313-320,1995; and Hubbard, *EMBO J.* 16:5572-5581, 1997). The exciting inference derived from these solution studies is that long-range perturbations may be coupled to slow conformational changes detected in the kinetic mechanism for PKA (Shaffer and Adams, supra). Thus, a tangible link between catalytic function and solution structure may now be established.

Prior kinetic studies have shown that conformational changes associated with ADP release provide a regulatory mode for substrate phosphorylation in the nrPTK, Csk. In the study presented herein, the effects of nucleotide binding on the solution conformation of Csk were monitored with DXMS. Earlier amide hydrogen exchange techniques have been successfully applied to two protein kinases, to date; PKA (Andersen et al., supra) and ERK2 (Resing and Ahn, *Meth. Enzymol.* 283:29-44,1997; Resing and Ahn, *Biochemistry* 37:463475, 1998; and Resing et al., *J. Am. Soc. Mass Spectrometry* 10:685-702,1999). Both kinases are structurally simple being composed primarily of kinase domains. In comparison, Csk has more elaborate domain structure with the tyrosine kinase domain flanked by two noncatalytic SH2 and SH3 domains. These domains are thought to limit movements in the kinase core, impair nucleotide access and release and diminish catalytic activity in the structurally related c-Src (Sicheri et al., supra). In this study DXMS demonstrates that nucleotide binding induces long-range changes in the structure of Csk. A comparison of the ATP (AMPPNP)- and ADP-forms reveals unique structural changes induced by the γ phosphate of the nucleotide. These structural effects ramify not only throughout the small and large lobes of the kinase domain but also modify intradomain dynamics.

B. Results of DXMS Analysis of Csk.

i. Tuning of Csk Proteolytic Fragmentation.

Prior to studying the hydrogen exchanged samples, digestion conditions that produced Csk fragments of optimal size and distribution for exchange analysis were established as described earlier. Minimal back-exchange and optimal pepsin digestion for Csk were obtained by diluting one part of the deuterated sample with one and a half parts of quench solution (0.8 M GuHCl in 0.8% formic acid). The quenched sample was then run over immobilized pepsin (66 µl bed volume) at a flow rate of 100 µl/min, resulting in digestion duration of 40 seconds. These conditions generated 28 high quality peptides covering 63% of the Csk sequence. Since both the amino group of the first amino acid and the amide hydrogen of the second amino acid exchange too rapidly to retain deuterons during the experiment, the total number of amide hydrogens followed by DXMS was 223 out of 444 non-proline residues (50%).

ii. Deuterium Incorporation into the Proteolytic Fragment Probes.

Figure 10:
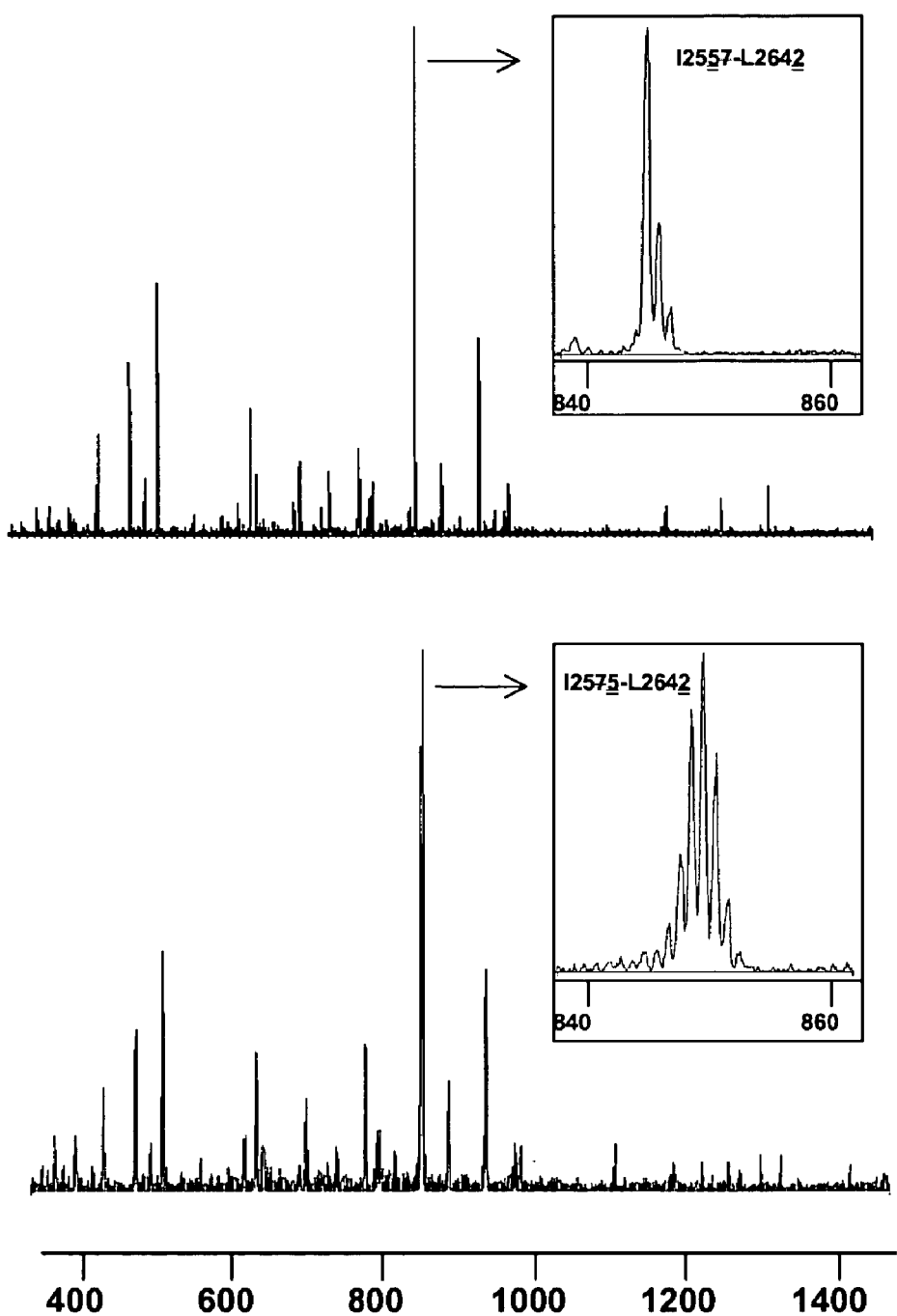
FIG. 10 shows the results of ESI-MS of pepsin-treated Csk before (upper panel) and after (lower panel) incubation with $D_2O$. The peak clusters corresponding to the peptide fragment, 1255-L262, are shown expanded in the insets in the upper and lower panels.

The incorporation of deuterium from solvent $D_2O$ can be monitored using DXMS. FIG. 10 shows the ESI spectra of proteolyzed Csk before and subsequent to dilution into $D_2O$. The insets in this figure highlight one specific peptide fragment, I255-L262. This probe appears as a cluster of peaks owing to the natural isotopic distribution of the atoms in the peptide. After 3 hours of incubation in $D_2O$, the envelope of peaks for the probes increases in overall mass and complexity. The centroids for these two clusters are used to determine the mass of the probe both before and after incubation with solvent deuterium.

iii. Effects of Nucleotide Binding on Deuterium In-Exchange.

Figure 11:
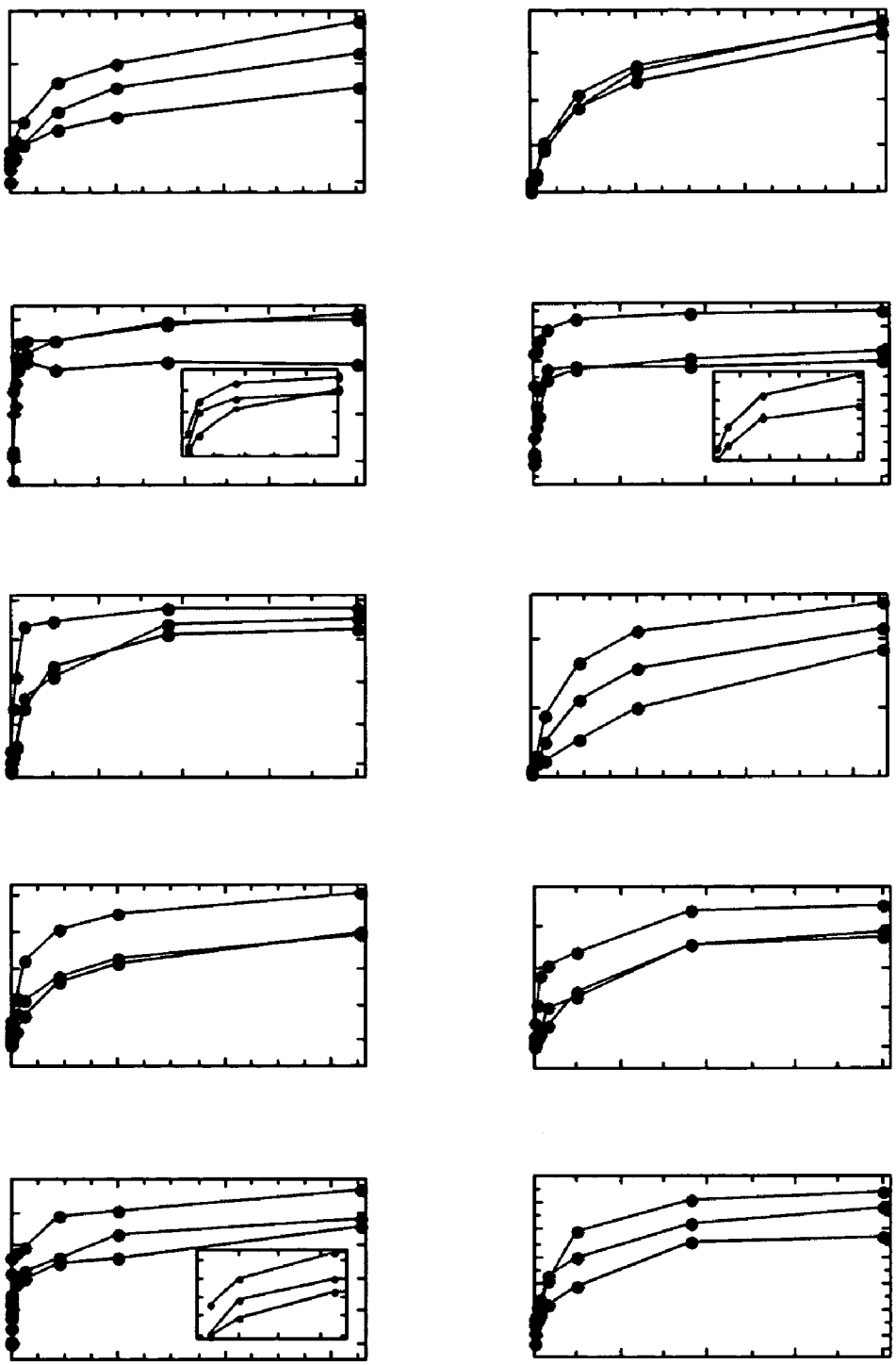
FIG. 11 illustrates the time-dependent deuterium incorporation in several peptide probes in the absence and presence of nucleotides, comparing deuterium incorporation into apo-, AMPPNP-bound, and ADP-bound forms of Csk. The probes in the individual plots correspond to the following structural elements based on the X-ray coordinates of Csk: E93-L103 (αA in SH2), S139-V144, V184-N191 (SH2-kinase linker), L198-M210 (glycine-rich loop), L234-M240 (αC), V249-V254, F310-L321 (catalytic loop), V322-F333, G334-L358 (activation loop), and G383-G402 (αG).

The average mass of each peptide was elucidated by integrating over the full envelope of peaks. To quantify the extent of deuterium incorporation at various time periods, the mass of each probe was converted to a number of in-exchanged deuterons using Equation 1. The in- and back-exchange controls set the zero and infinite time points for D(t). Each peptide fragment is unique with different numbers of exchangeable protons and different intrinsic exchange rates. This method detects total mass changes for each probe without defining the priority of amide exchange within each probe. Deuterium incorporation into the Csk probes was followed as a function of time in the absence and presence of two nucleotides: AMPPNP and ADP. FIG. 11 displays the time-dependent incorporation of deuterium into several typical probes. In some cases (e.g., S139-V144), the presence of either nucleotide has no effect on the incorporation of deuterium over the experimental time frame (10 seconds to 1200 minutes). These probes are considered non-protected by the ligand over the exchange times studied. By comparison, the rate of deuterium incorporation into other probes is impaired by the ligand. These probes are considered protected by the nucleotide. In no cases did the nucleotide increases the rate of deuterium incorporation compared to the apo-enzyme. The definition of whether a probe is protected by the nucleotide over the experimental time frame depends on the accuracy of the mass measurement in the ESI spectrometer. For the set of probes used in these studies kinetic traces that differ by more than 0.5 deuterons in mass at a minimum of two points are defined as experimentally different. Using this criteria, a number of probes have been identified whose deuteration rate is impaired by the presence of the nucleotide (see FIG. 11).

C. Discussion of DXMS Analysis of Csk.

Since the crystallographic solution of the first protein kinase structure approximately one decade ago, it has become apparent that this enzyme family undergoes structural changes that are linked to activity regulation. For example, many protein kinases have been crystallized in both "open" and "closed" forms that differ by domain rotations (Johnson et al., Cell 85:149-158, 1996). Other protein kinases that are regulated through phosphorylation and protein binding display large movements in loop and helical regions upon activation. The cyclin-dependent protein kinase, cdk2, and the insulin receptor kinase undergo large changes in helix αC and the activation loop when a cyclin binds in the former case and upon phosphorylation in the latter case Jeffrey et al., supra; Hubbard, supra; and Hubbard et al., Nature 372:748-754,1994). It has also been demonstrated that discrete structural changes partially or fully limit substrate processing in several protein kinases based on pre-steady-state kinetic measurements (Shaffer et al., supra; Shaffer and Adams, supra; and Jan et al., supra). In this example DXMS is employed to probe the solution conformation of the nonreceptor PTK, Csk. Previous kinetic studies have shown that slow conformational changes limit ADP release. To address whether Csk adopts any unique structural states that may be important for regulation, the solution conformation of the full-length enzyme was studied in the absence and presence of the product, ADP, and a nonhydrolyzable ATP analog, AMPPNP.

i. Effects in the Kinase Domain.

While two regions in the active site of Csk that are expected to interact with ATP (catalytic & glycine-rich loops) are highly protected from deuterium incorporation in the presence of AMPPNP, several regions outside the active site are also protected by nucleotide. For example, the probe encompassing helix αC is protected by AMPPNP by as much as 2 deuterons over intermediate exchange time frames. Such protection has also been observed in PKA upon ADP binding. This helix does not make any direct contacts with the nucleotide but rather contains a conserved residue (Glu-236, Glu-91 in PKA) that forms a salt bridge with another conserved residue (Lys-222, Lys-72 in PKA). Lys-72 in PKA has been shown to form interactions with the αβ phosphates of ATP suggesting that Lys-222 could serve a similar function in Csk. The electrostatic dyad between these two residues (Glu-Lys) is conserved in the enzyme family and also appears to be disrupted in several down-regulated protein kinases. For example, this disruption in the InRK and cdk2 is coordinately linked to movements in helix αC jeffrey et al., supra; and Hubbard, supra). While these motions occur upon cyclin binding for cdk2 and upon activation loop phosphorylation for the InRK, the protection observed in our H-D exchange experiments suggest that movements in this helix may be induced solely by nucleotide binding.

The association of nucleotide with Csk has profound effects on regions in the large lobe of the kinase domain. Protection of a probe containing the activation loop suggests that this region is affected by nucleotide binding. While this loop is not expected to contact ATP directly, a conserved aspartate (Asp-184 in PKA, Asp-332 in Csk) preceding the activation loop chelates the essential, activating $Mg^{2+}$ which stabilizes the γ phosphate of ATP. It is conceivable that protection in the activation loop upon AMPPNP binding in Csk may reflect conformational changes linked to movements in this preceding structural element. The binding of nucleotide to Csk has further effects on the large lobe of the kinase domain. Most notably, the probe containing helix αG is protected from deuterium incorporation by AMPPNP. This helix makes no direct contact with the nucleotide and is even further removed from the active site than helix αC and the activation loop. While it is not clear how AMPPNP can transmit such long-range effects across the kinase domain, space-filling models illustrate that the activation loop packs on top of helix G (Jeffrey et al., supra). Such findings suggest that the binding of the nucleotide has pervasive effects on the kinase domain which ramify from their origins in the small ATP-binding lobe down to the larger substrate-binding lobe.

ii. Inter-Domain Cross-Talk.

Prior kinetic studies have shown that the SH2 and SH3 domains of Csk enhance catalytic activity by approximately two orders of magnitude (Sondhi and Cole, *Biochemistry* 38:11147-11155,1999; and Sun and Budde, *Arch. Biochem. Biophys*. 367:167-172,1999). Such findings suggest that these domains play an important role in organizing the catalytic residues in the active site. Indeed, two regions near the interface between the SH2 and kinase domains display protection in the presence of AMPPNP. Probes corresponding to helix αA in the SH2 domain and a portion of the SH2-kinase linker region are protected by AMPPNP. In Csk, a short helix within the linker makes contacts with the kinase domain through helix αC. The coordinate protection in both the SH2-kinase linker and helix αC suggests that a "communication pathway" between the SH2 domain and active site is critical for catalytic function. Owing to protection by nucleotide of helix αA, this pathway may involve changes in the SH2 domain in addition to rigid domain-domain movements.

iii. Phosphorylation-Driven Motions.

The data presented thus far indicate that AMPPNP and presumably ATP induce both local and long-range movements in the kinase and neighboring SH2 domain. It has been shown that structural changes in Csk limit the rate of release of ADP, a phenomenon which regulates function. To probe whether the ADP-bound complex populates a unique conformation compared to the ATP-bound form, deuterium incorporation into Csk in the presence of ADP was studied. These studies are directed at localizing any structural effects induced by substrate phosphorylation to specific regions in the polypeptide chain, a pursuit that could offer insights into the nature of the slow, rate-limiting structure changes in Csk. While many of the probes protected by AMPPNP are equally protected by ADP, several key probes observe noticeable differences. In the kinase domain, the glycine-rich loop is more protected by ADP than AMPPNP. This could result partly from structural changes in the loop after phosphoryl transfer to the substrate. While it is difficult to know the molecular nature of this change, it is conceivable that the loop more adequately covers the diphosphate moiety of ADP compared to the triphosphate in ATP. Such motions may be necessary for configuring the γ phosphate into a productive form.

In addition to local effects on the glycine-rich loop, ADP has profound effects on the activation loop. In this region, ADP protects the loop to a lower extent than AMPPNP, suggesting that this region of the kinase domain may exhibit higher flexibility or solvent exposure after the delivery of the γ phosphate. This effect is not localized to the activation loop but rather is coupled to other motions within the large lobe. For example, helix αG is less protected in the presence of ADP than AMPPNP, a phenomenon that may reflect synchronous motions in this location. Whatever the cause, it is clear that delivery of the phosphoryl donor has pervasive effects on the kinase domain. These motions are also coupled to changes in two interfacial probes. The probes corresponding to helix αA in the SH2 domain and the SH2-kinase linker are more flexible in the presence of ADP than AMPPNP. Again, as with AMPPNP binding, ADP has long-range effects on the solution conformation of Csk. The nature of these long-range effects are markedly different depending on the presence of the γ phosphate in the nucleotide pocket. Such a striking contrast between hydrogen exchange properties as a function of substrate (AMPPNP) and product (ADP) may result from distinct conformational states. Since conformational dynamics limit substrate processing in this enzyme, the definition of critically affected regions will be useful for the understanding of protein phosphorylation.

EXAMPLE 2

DXMS Analysis used to Elucidate the Effects of cAMP and Catalytic Subunit Binding on cAPK Type IIβ Solvent Accessibility A. Background.

A myriad of physiological processes are controlled by the stimulatory effects of cAMP on cAMP-dependent protein kinase (cAPK). The regulatory (R) subunits of cAPK serve as negative regulators of cAPK, as the inactive kinase exists as a tetramer composed of an R-subunit dimer bound to two catalytic (C) subunits. Binding of two cAMP molecules to each R-subunit causes dissociation of the holoenzyme complex and releases an active C-subunit. The R-subunits are known to exist in either one of two physiological states: in complex with the C-subunit or free and cAMP-saturated. A cAMP-free and C-subunit free state is believed to only exist transiently following translation due to the high affinity for cAMP and the intracellular cAMP concentrations.

Two general classes of R-subunits, type I and type II, are known to exist and differ by autophosphorylation, molecular weight, disulfide cross linkage, and cellular localization. Each type of R-subunit can be further classified as either α or β which differ by tissue distribution and antigenicities. Thus there are four isoforms of the R-subunits. Despite these molecular and cellular differences, all four isoforms possess a conserved and well-defined domain structure comprised of an amino-terminal dimerization/docking domain, two-tandem cAMP binding domains (designated A and B) at the carboxy-terminus, and a variable, interconnecting linker region. The linker region contains a substrate-like inhibitor sequence that docks to the active site cleft of the C-subunit and each cAMP-binding domain contains a highly conserved phosphate binding cassette that binds 1 cAMP molecule. In addition to the molecular and cellular differences, the R-subunit isoforms also exhibit distinct structural differences.

Activation of cAPK is a triad of the C-subunit, cAMP, and the R-subunit. The R-subunit is at the center of this triad, as it toggles between a cAMP-bound state and a C-subunit-bound, cAMP-free state. Understanding the conformational changes induced upon binding of cAMP and the C-subunit binding to the R-subunit is essential in understanding the mechanism of cAPK activation, as a series of conformational changes is believed to be critical for holoenzyme dissociation.

Conformational changes upon cAMP binding to domain A, cA, and domain B, cB, have been observed by numerous methods, including fluorescence, circular dichroism, and cysteine sulfydryl reactivity studies. Binding of cAMP leads to a general tightening of the domain where binding occurs and also alters the conformation of the second domain. This is evidenced by the increased $k_a$ and decreased $K_d$ for the cB domain when the cA domain is vacant. Additionally, when the R-subunit is bound to C-subunit, the cB domain must be saturated before cAMP can bind to the cA domain. The specific conformational changes that occur upon nucleotide binding must be subtle, however, because neutron scattering data of an RIIα N-terminal deletion mutant did not show any large scale conformational changes upon cAMP binding.

Conformational changes in the R-subunits have also been observed upon C-subunit binding. Chemical modification studies on RIIα and RIα and limited proteolysis studies on RIIα identified residues whose reactivity was dependent on the presence or absence of the C-subunit. The C helix of the RIα cA domain was identified as a molecular switch between the cAMP-bound or the C-bound conformations, implying that this helix is essential for toggling between these two distinct conformations. Structural studies, such as neutron scattering, have also highlighted large-scale conformational changes in the R-subunits upon C-subunit binding. Attempts at solving the crystallographic structure of the RIα holoenzyme using molecular replacement of the cAMP-bound nucleotide binding domains were unsuccessful, suggesting a significantly different conformation of the cAMP-free cA domain compared to the cAMP-bound cA domain.

It is clear that conformational changes do occur upon binding of cAMP or the C-subunit but the identity of the specific residues that undergo these changes are still unknown. Amide H/2H exchange measured by mass spectrometry is one technique available for analysis of conformational changes in proteins. In this example, DXMS is used to examine the solvent accessibility of the RIIα isoform in each of the two physiological states: complexed with C-subunit ($R_2C_2$) or free and saturated with cAMP ($R_2cAMP_4$).

In contrast to the ubiqitous and well-characterized RIα isoform, the RIIβ isoform is unique because it is selectively expressed as the predominant R isoform in the brain and adipose tissue of a variety of mammals, with limited expression elsewhere. RIIβ is also believed to be adapted for the metabolic regulation and cell functions in the central nervous system. Knockout of the RIIβ gene in mice underscored the physiological importance of this isoform, as the mice displayed a lean, obesity-resistant phenotype.

Because it is necessary to separate the conformational effects of removing cAMP from the effects of C-subunit binding, three states of the RIIρ isoform have been examined in this example: cAMP-free, cAMP-bound, and C-subunit-bound (holoenzyme) RIIβ. Comparison of the results from these analyses reveals that binding of either cAMP or C-subunit results in unique changes in solvent accessibility within the protein such that a C-subunit bound RIIβ subunit is not conformationally identical to a cAMP-free RIIβ subunit.

B. Results of DXMS Analysis or RIIβ.

i. Tuning of RIIβ Proteolytic Fragmentation.

Digestion conditions that produced RIIβ fragments of optimal size and distribution for exchange analysis were established before the exchange experiments. These conditions generated 82 identified and analyzed peptides (see FIG. 12). Thirty-eight of the identified peptides, still representing >99% of the entire sequence (414 out of 415 amino acids), were used in the following analysis (bold lines in FIG. 12). Since both the amino group of the first amino acid and the amide hydrogen of the second amino acid exchange too rapidly to retain deuterons during the experiment, the total number of amide hydrogens followed by this study was 346 out of 406 non-proline residues (85%). Each peptide was numbered and discussed in terms of the amide residues whose exchange was theoretically observed (i.e., the length of the peptide minus the first 2 amides).

ii. Deuterium Incorporation into cAMP-bound RIIβ.

The hydrogen/deuterium exchange experiment coupled with proteolysis and mass spectrometry revealed the solvent accessibility of full length RIIβ and complemented the NMR and crystallographic studies on the dimerization/docking domain and cAMP-binding domains, respectively. A relatively slow exchanging, N-terminal region corresponded to helices I and II of the D/D domain. An approximately 100 amino acid long fast exchanging region was mapped to the linker region. This region has been found to be extended, perhaps with little or no structure, solvent accessible, and very mobile, thus the fast exchange was not surprising. It is noteworthy that the deletion mutant (Δ1-111) which produced the crystals used in the crystallographic structure lacks this highly dynamic linker region.

A large slow exchanging region corresponded to the cAMP-binding domains. The slowest exchanging regions in cAMP-binding domains are residues 191-200, 222-224, 228-233, 236-242, 245-250, and 341-374, all of which are either β-sheets or α-helices in or near the PBCs. Three fast exchanging regions within the cAMP-binding domains were identified. Residues 276-281 and 390-416 correspond to a loop region and the C-terminus, respectively. Residues 326-338 correspond to a region within the cB domain (residues 326-333) whose electron density is not sufficiently well defined, suggesting that it is a dynamic region with little or no structure.

Figure 13:
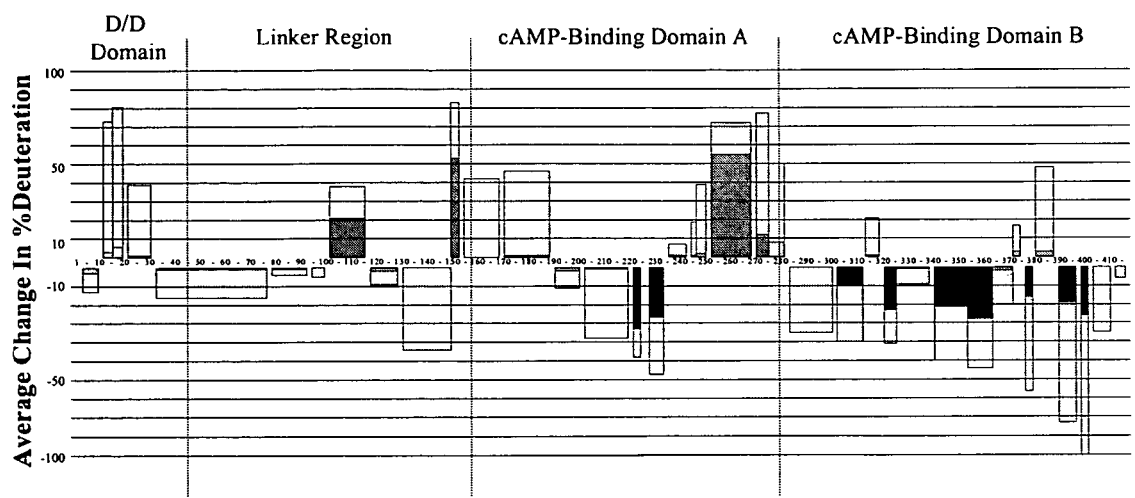
FIG. 13 graphically illustrates the maximum change in % deuteration between cAMP-bound and C-subunit bound conformations of RIIβ. The domain boundaries are shown as dashed lines.

The change in solvent accessibility of the RIIβ peptides upon binding of either cAMP or C-subunit was determined (see Table 1). FIG. 13 shows a graphical representation of the solvent accessibility differences between the two physiological states, cAMP-bound and C-subunit bound. To classify the solvent accessibility of a given peptide as significantly different between these two states, the change in % deuteration must be >10% for at least 2 time points. Peptides within both cAMP-binding domains demonstrated increased deuteration upon C-subunit binding, but the majority of these peptides localized to the cB domain. Peptides that were less deuterated upon C-subunit binding were spread across the entire protein but were concentrated in the cA domain. A number of peptides exhibiting no difference in deuteron incorporation between the cAMP-bound and holoenzyme forms of RIIβ can also be identified in all subdomains.

TABLE 1

Maximum Change in % Deuteration Upon cAMP or C-Subunit Binding to RIIβ

| Peptide[a] | Residues[b] | $R_2(cAMP)_4 - R_2C_2^{cf}$ | $R_2 - R_2(cAMP)_4^{df}$ | $R_2 - R_2C_2^{ef}$ |
|---|---|---|---|---|
| Dimerization/Docking Domain | | | | |
| 2-9 | 4-9 | −7% | 5% | −5% |
| 10-15 | 12-15 | 8% | −12% | −12% |
| 13-19 | 15-19 | 19% | −20% | −3% |
| 20-30 | 22-30 | 2% | −5% | −4% |
| Linker Region | | | | |
| 31-76 | 33-76 | −3% | 1% | 3% |
| 77-92 | 79-92 | −2% | −4% | −5% |
| 93-99 | 95-99 | −4% | −8% | −5% |
| 100-115 | 102-115 | 38% | −3% | 36% |
| 116-128 | 118-128 | −7% | −5% | −6% |
| 129-149 | 131-149 | −3% | 3% | 4% |
| (130-152)-(130-149) | 150-152 | 76% | −27% | 61% |
| cAMP-Binding Domain A | | | | |
| 153-168 | 155-168 | −4% | 3% | −4% |
| 169-188 | 171-188 | 5% | 2% | 5% |
| 189-200 | 191-200 | −4% | −2% | −4% |
| 201-219 | 203-219 | −5% | 6% | 4% |
| 220-224 | 222-224 | −40% | 42% | −29% |
| 226-233 | 228-233 | −36% | 18% | −21% |
| 234-240 | 236-242 | 2% | 4% | 5% |
| 243-246 | 245-246 | 6% | 9% | 11% |
| (243-250)-(243-246) | 247-250 | 7% | −5% | 3% |
| 251-268 | 253-268 | 66% | 6% | 65% |
| 269-275 | 271-275 | 24% | −9% | 28% |
| (269-281)-(269-275) | 276-281 | 19% | 4% | 20% |
| cAMP-Binding Domain B | | | | |
| 282-300 | 284-300 | −4% | 13% | 9% |
| 301-312 | 303-312 | −15% | −10% | −16% |
| 312-318 | 314-318 | 5% | −6% | −4% |
| 324-338 | 326-338 | −3% | −8% | −10% |
| (319-338)-(324-338) | 321-325 | −31% | 7% | −35% |
| 339-353 | 341-353 | −30% | 16% | −14% |
| 352-363 | 354-363 | −36% | 23% | −17% |
| (352-371)-(352-363) | 364-371 | −3% | 9% | 7% |
| (354-374)-(354-371) | 372-374 | 10% | −16% | 12% |
| 375-379 | 377-379 | −33% | 10% | −29% |
| 379-387 | 381-387 | 20% | 10% | 25% |
| 388-396 | 390-396 | −45% | 8% | −42% |
| 397-401 | 399-401 | −55% | 22% | −33% |
| 402-410 | 404-410 | 6% | 7% | 9% |
| 411-416 | 413-416 | −2% | −3% | −4% |

[a]Peptide(s) analyzed. In the case of two peptides, subtraction method was used to sublocalize deuteriums incorporated.
[b]Residues actually monitored by analyzing deuterium incorporation into the peptide.
[c]Deuteration difference between cAMP-bound RIIβ and holoenzyme (positive if cAMP-bound RIIβ is more deuterated).
[d]Deuteration difference between cAMP-free and cAMP-bound RIIβ (positive if cAMP-free RIIβ is more deuterated).
[e]Deuteration difference between cAMP-free RIIβ and holoenzyme (positive if cAMP-free RIIβ is more deuterated).
[f]Numbers in bold are considered to be a significant change.

iii. Dimerization/Docking Domain.

Figure 14:
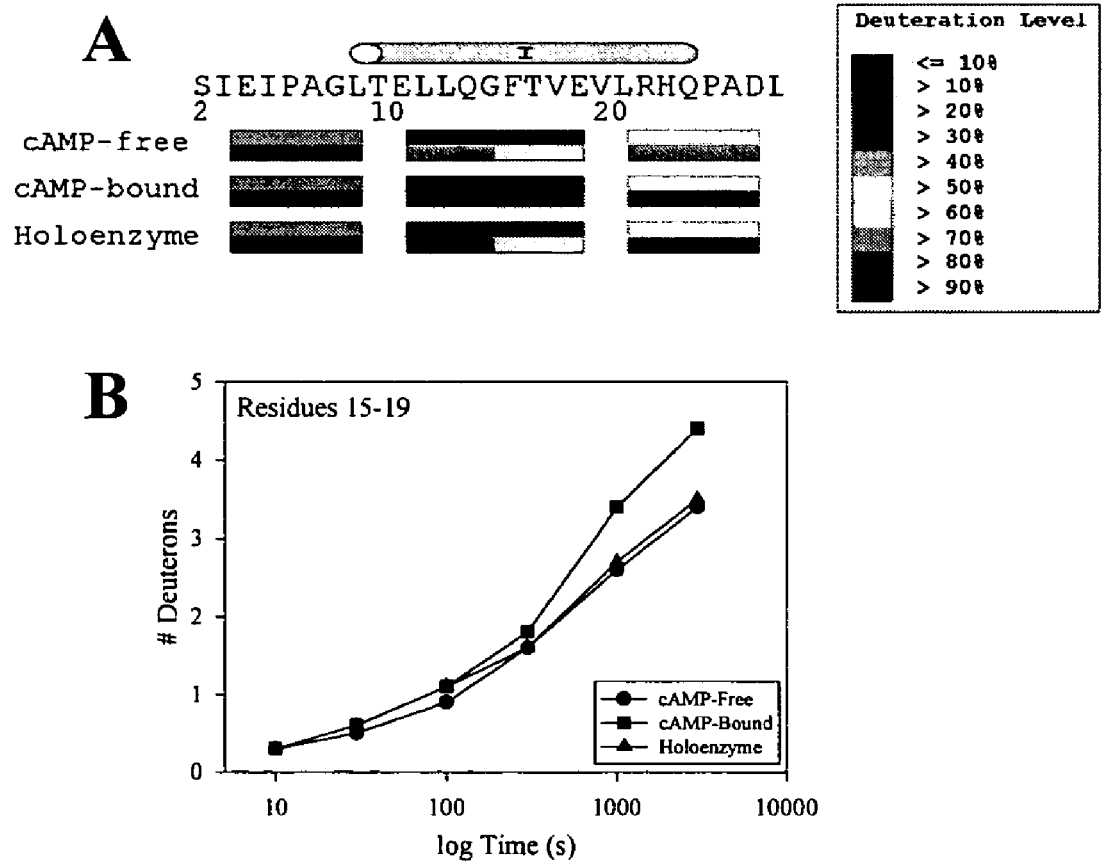
FIG. 14 collectively shows amide exchange of the dimerization/docking domain.

The dimerization/docking domain of RIIβ is comprised of residues 1-45. Helix I is solvent inaccessible and is flanked by a solvent accessible N-terminus and turn that leads into Helix II (see FIG. 14A). Residues 15-19 (Helix I) showed an equivalent level of deuteration for the cAMP-free and holoenzyme forms but an increase in deuteration at the longer time points (1000 s and 3000 s) for the cAMP-bound form (see FIG. 14B). This portion of Helix I, therefore, is sensitive to the addition of cAMP.

iv. Linker Region.

Figure 15:
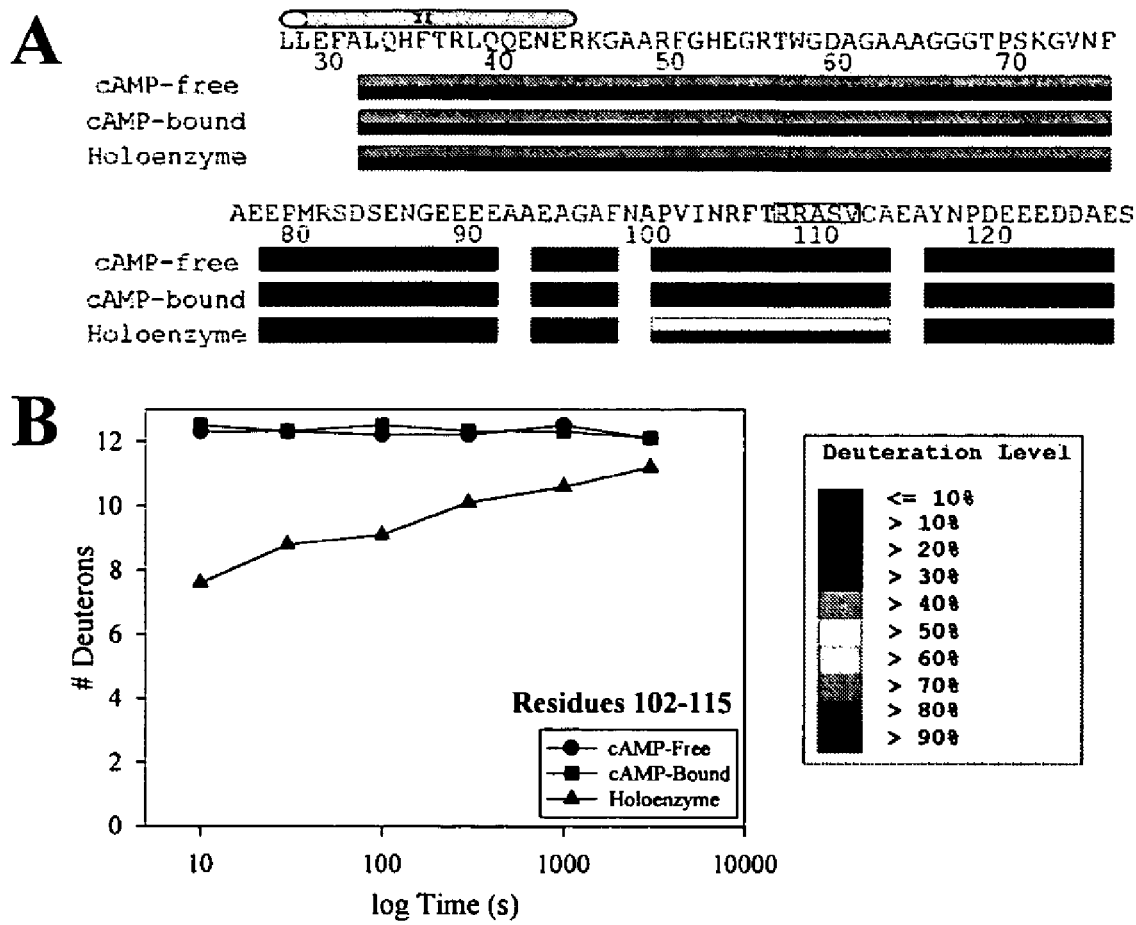
FIG. 15 collectively shows amide exchange of the linker region.

The linker region is highly solvent accessible in all three forms of RIIβ (see FIG. 15A). A localized region of protection (approximately 5 amides) upon C-subunit binding was observed for residues 102-115 (see FIG. 15B). This protection is due exclusively to C-subunit binding, as there was no observed difference in amide exchange between the cAMP-bound and cAMP-free forms. This result is consistent with the fact that this peptide includes the pseudosubstrate site.

v. cAMP-Binding Domains.

Residues within the cAMP-binding domains whose solvent accessibility was monitored are highlighted on the RIIβ crystallographic structure. The structure includes residues 130-157 ($\alpha X_n$ and $\alpha X_n'$), which are technically part of the linker region but for this report will be discussed with the cAMP-binding domains (residues 158-416).

Figure 16:
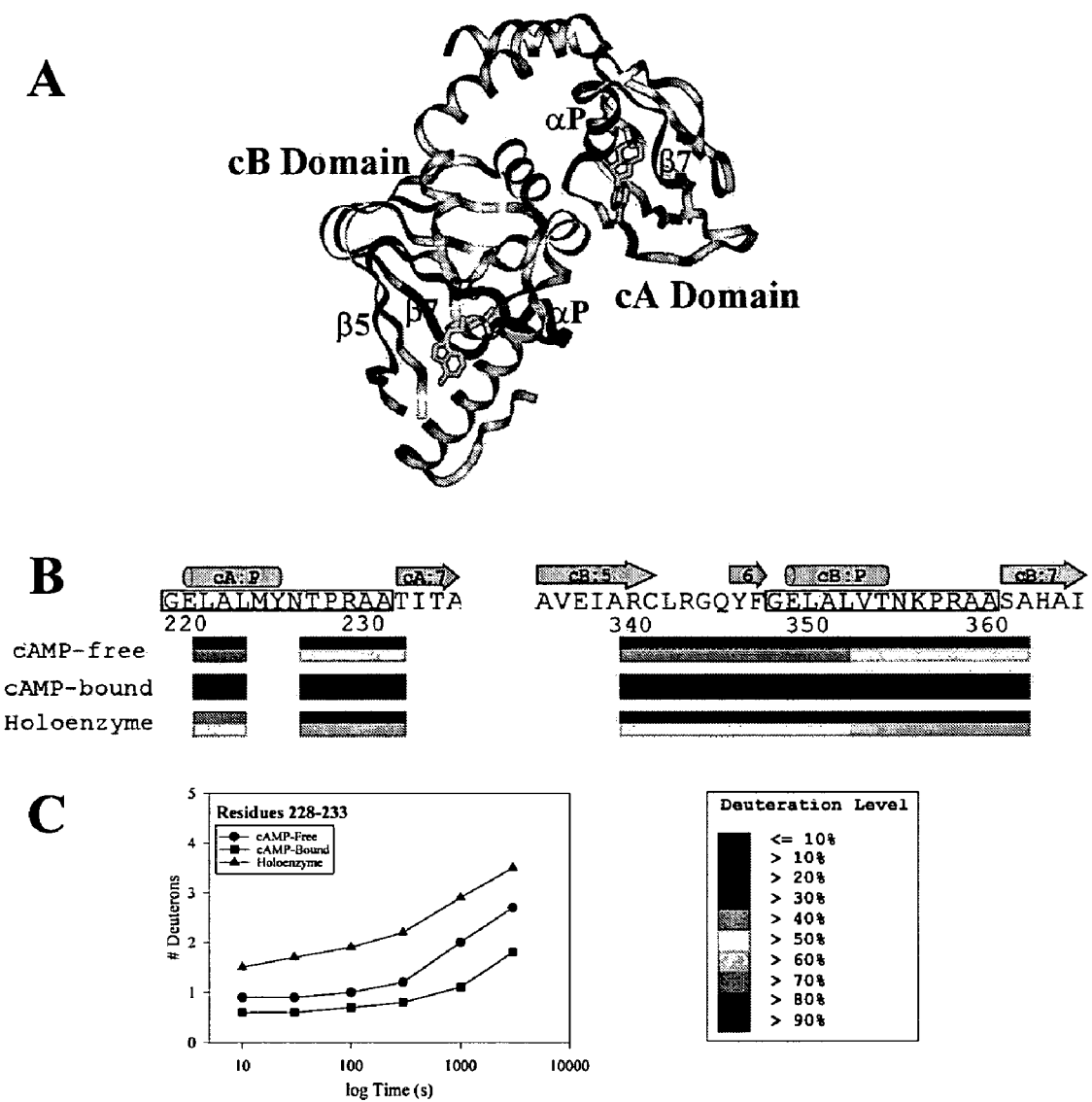
FIG. 16 collectively shows amide exchange of PBCs.

As expected, the removal of cAMP leads to increased deuteration of peptide fragments that comprise the PBCs (see FIG. 16A). These peptides, which include residues 222-224 (cA:αP), 228-233 (cA:PBC), 341-353 (cB:β6/αP), 354-363 (cB:PBC), are generally solvent inaccessible at early time-points (see FIG. 16B). At increasing time points, all of these peptides showed further deuteration upon C-subunit binding than in the cAMP-free state (see FIGS. 16B and 16C), suggesting that formation of the holoenzyme complex leads to a further opening of the PBCs.

Figure 17:
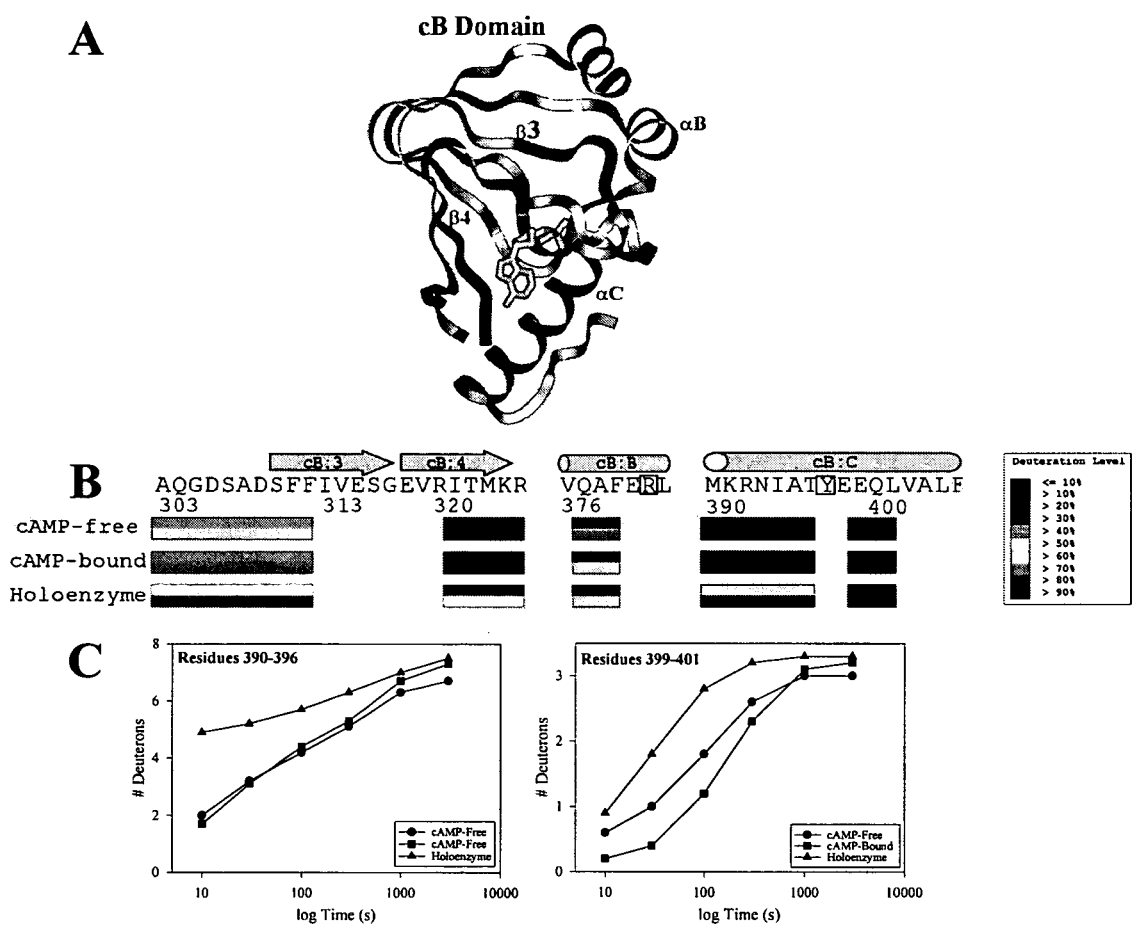
FIG. 17 collectively shows amide exchange of cAMP-binding domain peptides showing increased deuteration upon C-subunit binding.

Additionally, the amide exchange of 5 peptides within the cB domain but not part of the PBC, residues 303-312 (cB:β3), 321-325 (cB:β4), 377-379 (cB:αB), 390-396 (cB:αC), and 399-401 (cB:αC), was affected by C-subunit binding (see FIG. 17A). These residues are moderately solvent accessible (10-40%) at the initial time point (see FIG. 17B) and showed increased solvent accessibility upon C-subunit binding compared to the cAMP-free state during the time course (see FIGS. 17B and 17C). With the exception of residues 399-401, the solvent accessibility of these peptides is increased upon C-subunit binding but is unaffected by just cAMP removal. Residues 399-401, alternatively, are sensitive to both cAMP and C-subunit binding, as removal of cAMP leads to an increase in amide exchange and C-subunit binding leads to further amide exchange than in the cAMP-free state.

A number of peptides demonstrated a decrease in amide exchange upon C-subunit binding (see FIG. 18A). These peptides show low to moderate solvent accessibility at the initial time point (see FIG. 18B). A dramatic decrease in amide exchange is observed in residues 150-152 ($\alpha X_n'$, immediately preceding the cA domain) and 253-268 (cA:αC, cA:αC') upon C-subunit binding (see FIG. 18C). The decrease in exchange for 253-268 appears to be due exclusively to C-subunit binding, as no difference in amide exchange upon cAMP binding was observed. Residues 150-152 showed limited protection from cAMP binding in addition to C-subunit protection. Residues 271-275 (cA:αC'), 276-281 (cB:αA), and 381-387 (cB:βB/αC) also showed decreased amide exchange that appears to be due exclusively to C-subunit binding (see FIG. 18C). The extent of protection by C-subunit, however, is not as large as for residues 150-152 and 253-268.

C. Discussion of DXMS Analysis of RIIβ.

i. Dimerization/Docking Domain is Sensitive to the Absence of cAMP.

The number of deuterons incorporated by residues 15-19 (helix I) was dependent on the presence or absence of cAMP, including cAMP removal by holoenzyme formation. Because this peptide is exclusive of sites where cAMP is known to bind, this indicates that inter-domain "cross talk" exists in RIIβ such that conformational changes upon ligand binding are transmitted from the binding site to other regions within the protein. Additionally, helix I of the dimerization/docking domain provides the docking site for A-Kinase Anchoring Proteins (AKAPs). The sensitivity of residues 15-19 to cAMP binding means that cAMP binding could affect RIIβ subcellular localization by the AKAPs.

ii. Sites of Protection by C-Subunit Binding are Observed in the Pseudosubstrate Site.

Residues 102-115, which contain the pseudosubstrate site (residues 109-113), show protection upon C-subunit binding that is believed to result from direct interactions with the C-subunit. At the shortest time point (10 s), the difference in number of deuterons incorporated between cAMP-bound RIIβ and holoenzyme was 5 deuterons, indicating a minimum of 5 amide hydrogens were protected upon C-subunit binding. As the pseudosubstrate site is 5 amides long, this 5 amide protection can be attributed to result from C-subunit binding to the pseudosubstrate site. Previous RIα studies have suggested that the P-4 to P-11 residues amino-terminal to the pseudosubstrate site also interact with C-subunit. The results presented herein do not indicate any C-subunit protection beyond the pseudosubstrate site. The high levels of deuteration for the linker region (residues 31-128) at the earliest time point indicate that most of the exchange events occurred before the time window employed. Additional protection may have been observed with shorter time points.

iii. Sites of Protection by C-Subunit Binding are Observed in Both cAMP-Binding Domains.

Residues 253-268, which encompass the C-helix of the cA domain, show a dramatic decrease in solvent accessibility upon C-subunit binding that is believed to result from direct interactions with the C-subunit (see FIG. 18C). Previous studies on RIα indicated that the cA domain C-helix provides a peripheral docking site for C-subunit binding to the R-subunits. In addition to being a determinant for high affinity binding to the C-subunit, the C-helix of RIα is protected from solvent exchange upon C-subunit binding. In RIIβ, residues 253-268 of the C-helix showed a dramatic protection upon C-subunit binding such that, compared to the cAMP-bound protein, at least 10 amide hydrogens are protected from deuteration upon C-subunit binding. The absence of protection by cAMP binding in this region suggests that this difference is due exclusively to C-subunit binding. A peripheral C-subunit docking site thus appears to also exists in the RIIβ cA domain C-helix.

Residues 150-152 ($\alpha X_n'$), which sit alongside the cA domain C-helix, also showed significantly decreased solvent accessibility in the C-subunit bound state compared to the cAMP bound state of RIIβ. The strong protection observed for these residues suggests that $\alpha X_n'$ may also provide a site of direct interaction with the C-subunit. Interestingly, residues 155-165 (cA:αA) showed no observable difference in amide exchange upon C-subunit binding (see FIG. 13). Single-site mutational analysis of this region in RIα suggested that E140 and D143 are required for high-affinity binding of RIα to the C-subunit. The absence of protection in the RIIβ A-helix suggests an isoform-specific C-subunit interaction surface in RIα and RIIβ.

The decreased solvent accessibility upon C-subunit binding observed in residues 271-275 and 276-281, which comprise the cA domain C"helix and the turn following this helix, respectively, is believed to be a propagated effect from interactions at the peripheral C-subunit binding site of the cA domain C-helix. The decrease in exchange is not attributed to direct binding primarily because the decrease in solvent accessibility is not as dramatic as that observed for residues 253-268 and 150-152. Binding of the C-subunit, then, affects the entire cA domain C-helix and not just peripheral binding site within the helix.

Figure 18:
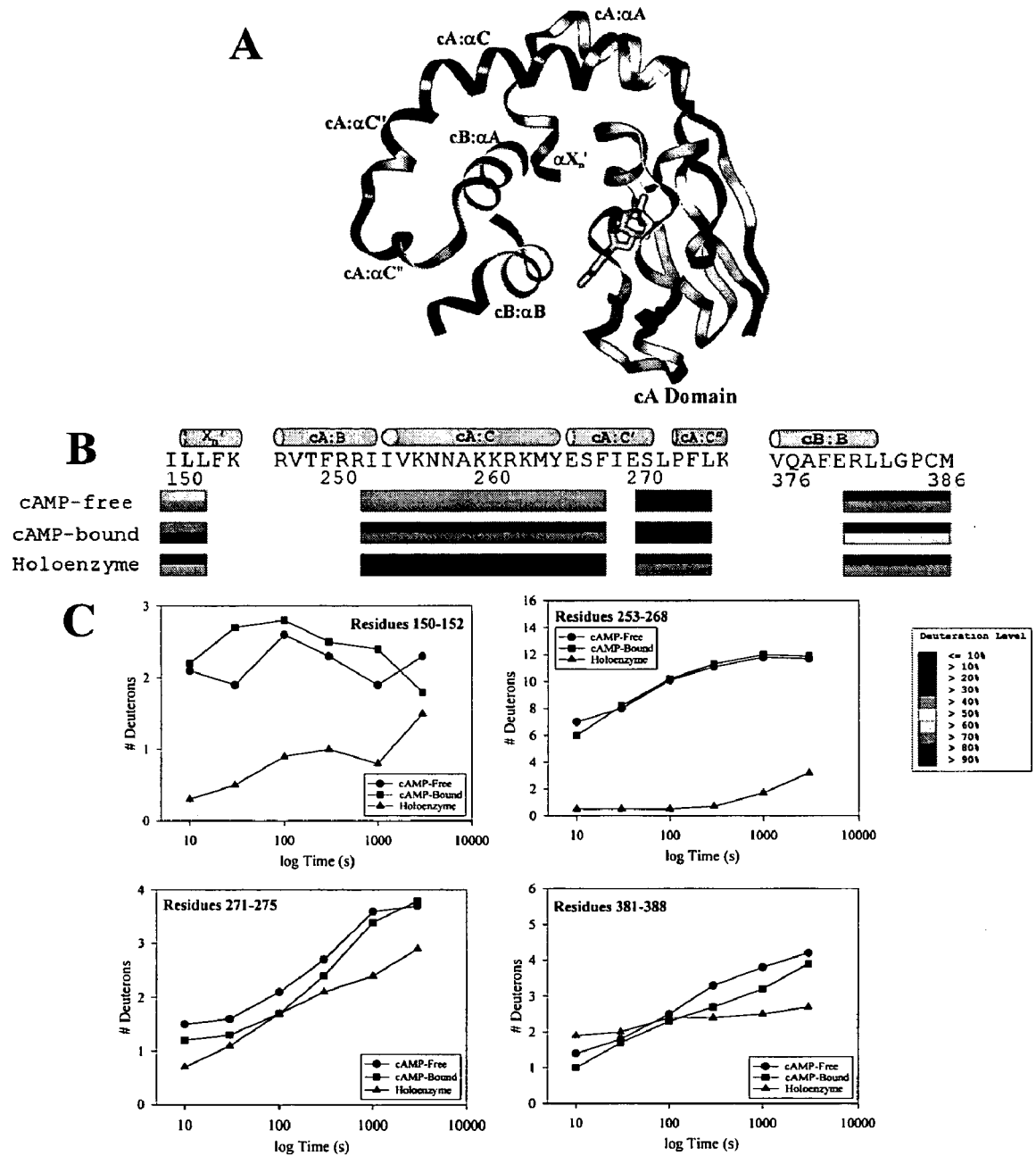
FIG. 18 collectively shows amide exchange for cAMP-binding domain peptides showing decreased deuteration upon C-subunit binding.
Figure 19A:
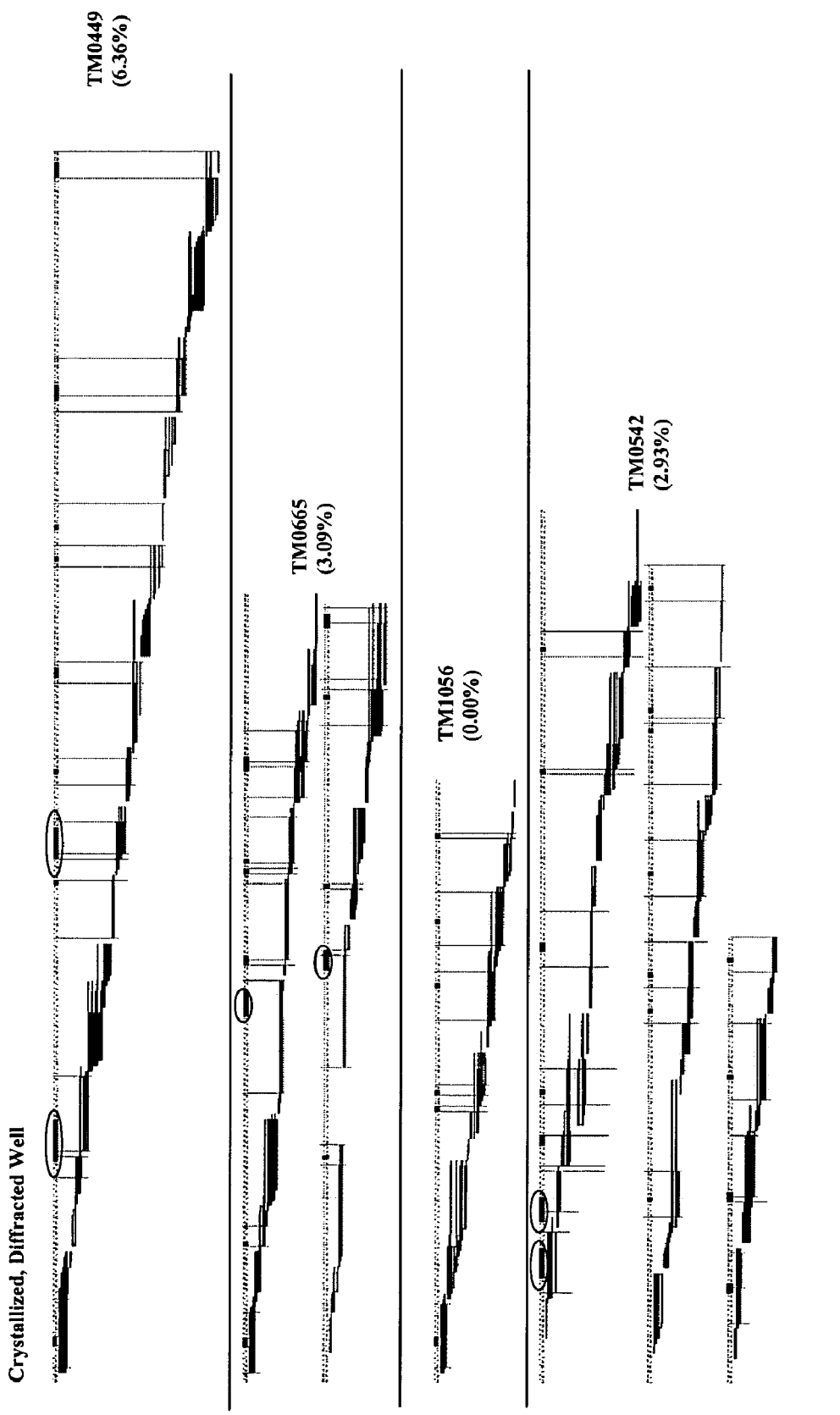
FIGS. 19A and 19B are proteins that crystallized and diffracted well.
Figure 19B:
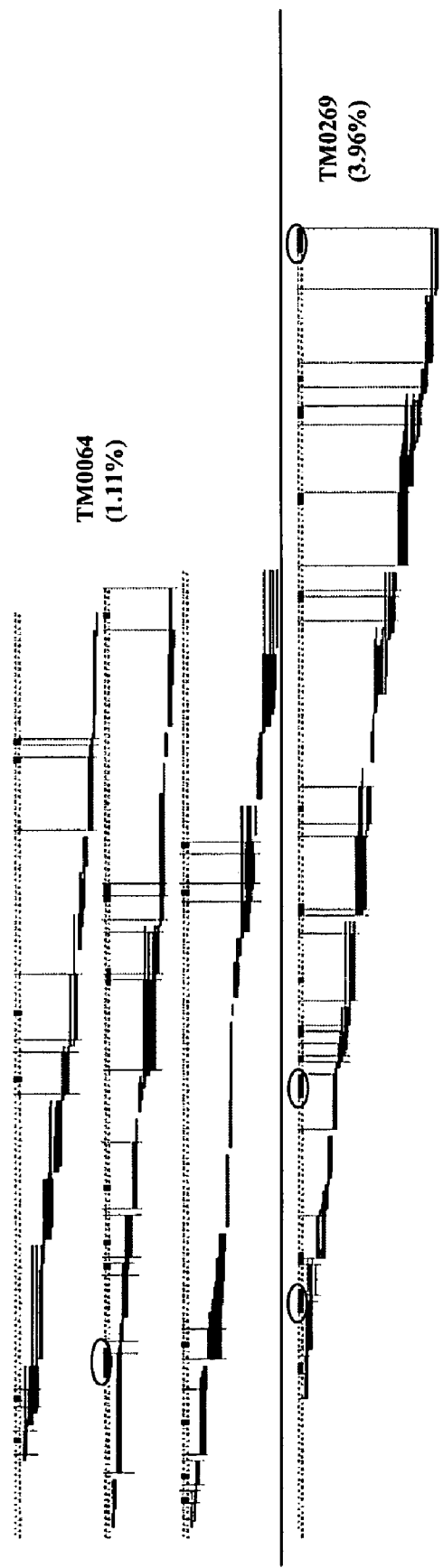
Figure 19C:
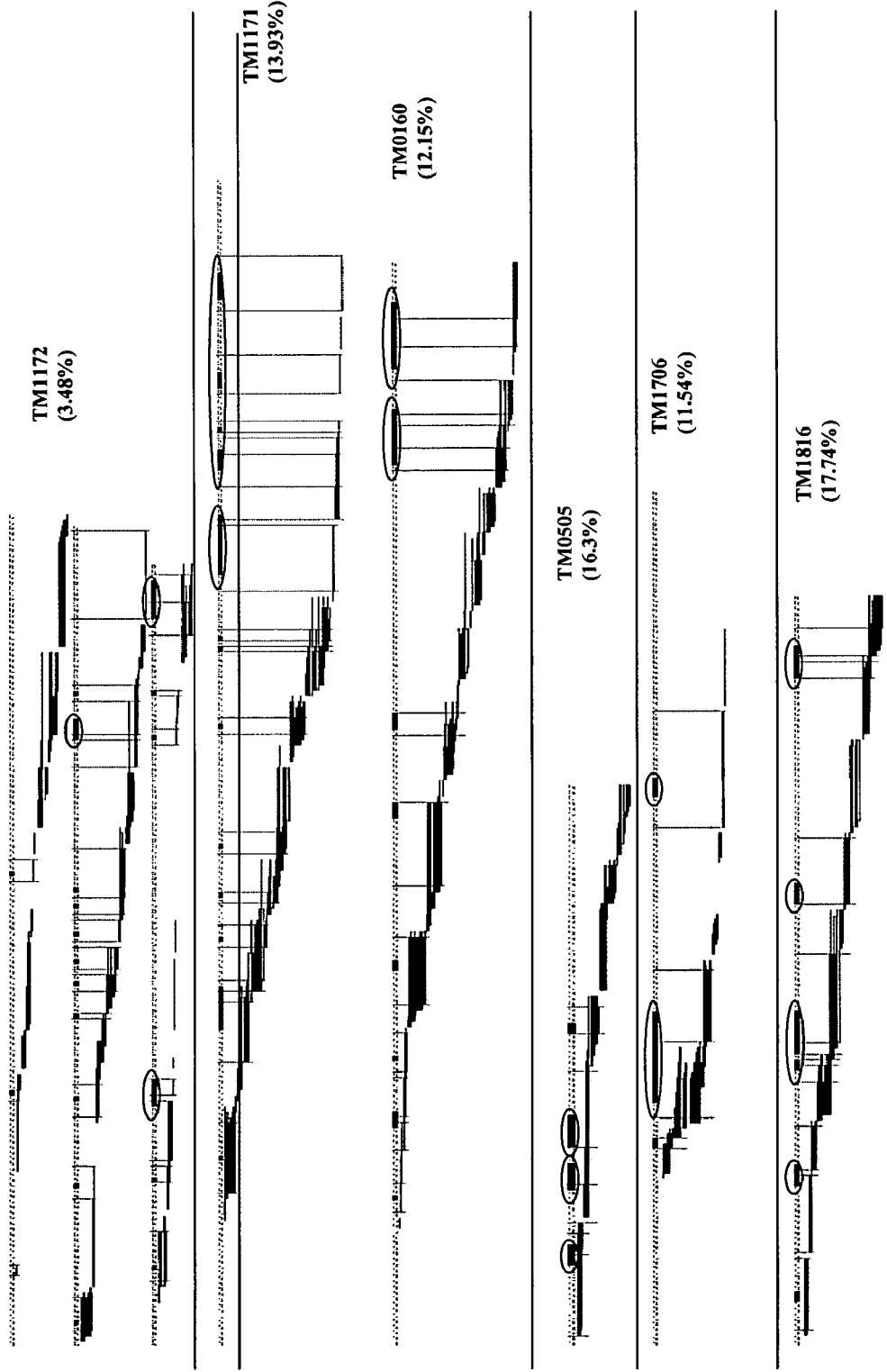
FIGS. 19C-19E are proteins that did not crystallize or had poor diffraction properties.
Figure 19D:
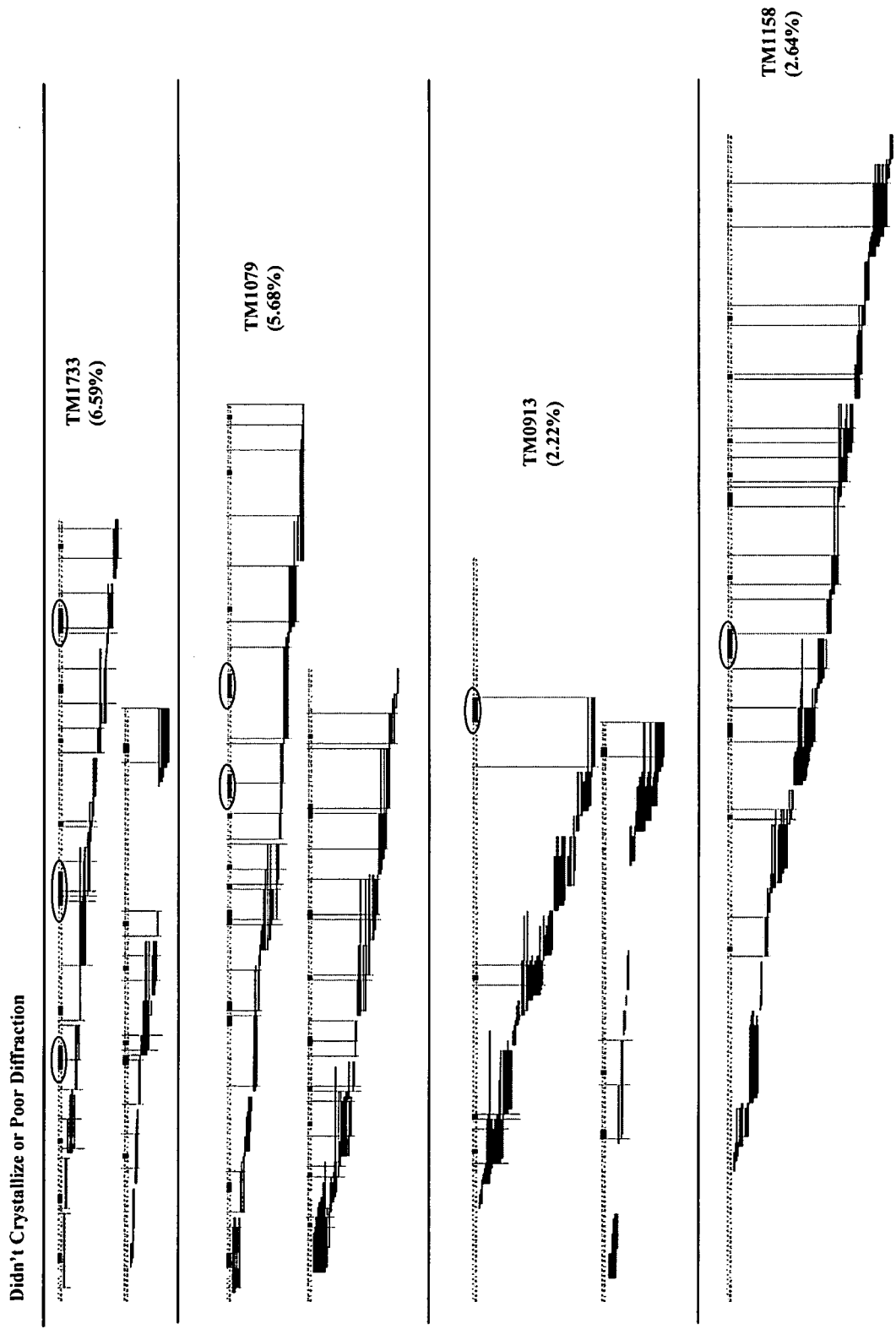
Figure 19E:
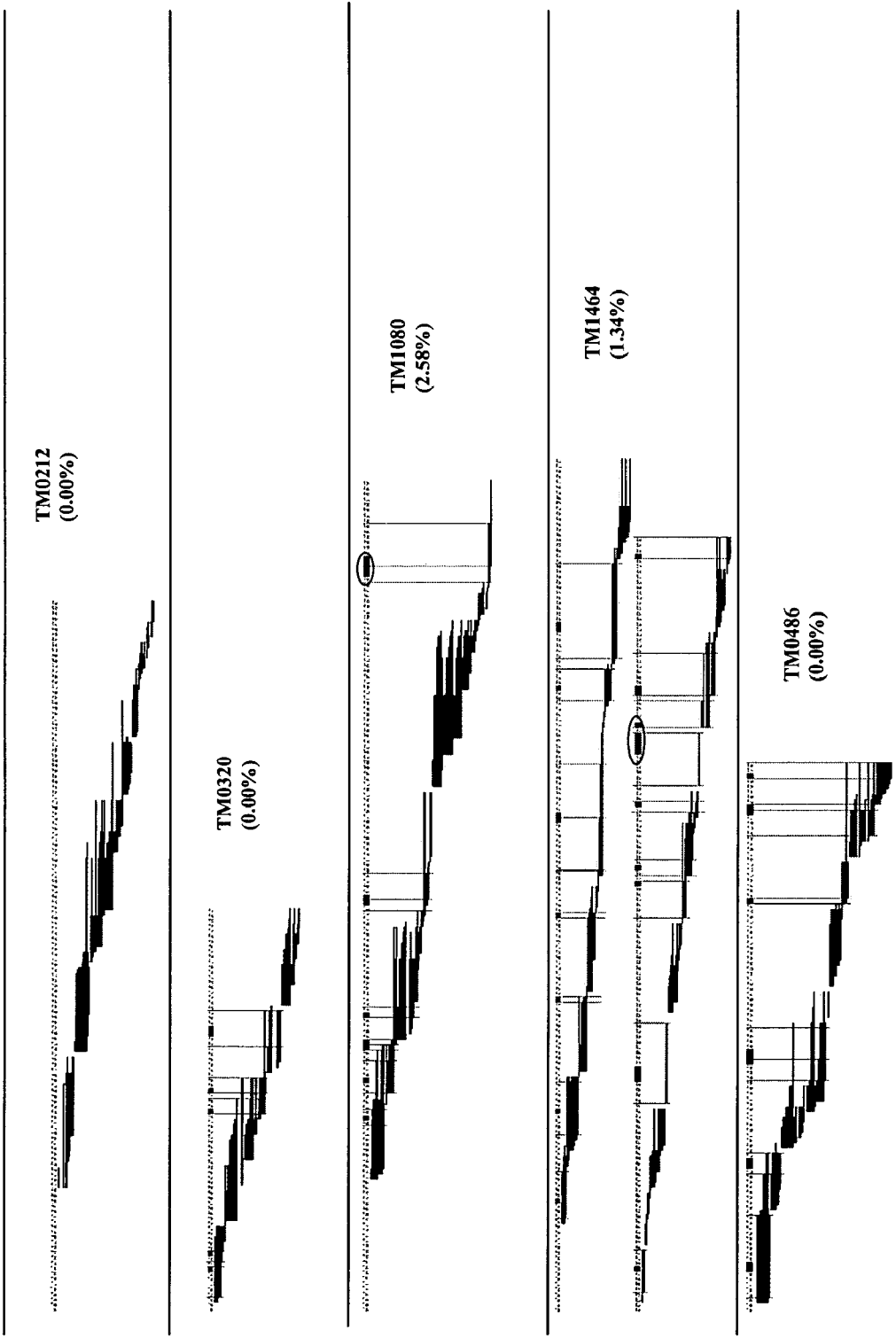

The amide exchange behavior of residues 381-387 (cA:B domain B and C helices) is complicated (see FIG. 18). Compared to the cAMP-bound and cAMP-free states, upon C-subunit binding the peptide was more deuterated at the 10 s and 30 s time points while it was less deuterated at the longer time points (300-3000 s). This indicates that there are two types of amide hydrogens in this peptide: one with exchange rates that are slowed and another with exchange rates that are accelerated by C-subunit binding. The influence of C-subunit binding on residues 381-387, of which Arg381 and Leu382 are part of the cB domain B-helix, is striking because of the interaction between the cB domain B-helix and the cA domain. Arg381 stacks against the adenine ring of the cAMP molecule sequestered in the cA domain binding pocket, thus protection of residues 381-387 suggests an intimate connection between C-subunit binding and the cA domain binding pocket. Thus, the C-subunit binding to the peripheral binding site of the cA domain C-helix could induce a conformational change in the cB domain B-helix. This would in turn alter the stacking of Arg381 against the cAMP molecule within the cA domain binding pocket and facilitate the release of cAMP. Furthermore, the cB domain C-helix stacks against the cAMP molecule sequestered in the cB domain binding pocket and acts as a lid for the β-barrel to shield the cAMP molecule from solvent. A conformational change within residues 381-387, which includes the turn leading into the cB domain C-helix, could also facilitate the release of cAMP bound to the cB domain.

iv. C-Subunit Binding Propagates Changes in Solvent Accessibility Within the cAMP-Binding Domain β-Barrel Subdomain.

As expected, the PBCs showed increased solvent accessibility upon cAMP removal. Each cassette (residues 220-232 and 349-361) has three backbone amides and two amino acid sidechains within hydrogen bonding distance of the cAMP molecule. Binding of the C-subunit results in an increased level of amide exchange within the cAMP-binding pockets that is beyond the exchange resulting from simple removal of cAMP. Therefore, C-subunit binding propagates additional conformational changes to the PBCs that may facilitate the release of cAMP. The same trend in amide exchange is also observed for residues 399-401 of the cB domain C-helix. The fact that residues within this cB domain "lid" become more solvent accessible upon holoenzyme formation further supports the hypothesis that C-subunit binding may facilitate the release of cAMP and "prime" the cB domain for future cAMP binding.

Interestingly, residues 303-312, which exhibited an increase in amide exchange, include 2 conserved Asp residues (Asp306 and Asp309) that are indirectly linked to the cB domain cAMP molecule through a conserved Arg residue (Arg359). This Arg is essential for cAMP binding as it interacts with the cAMP exocyclic oxygen. The speculation that C-subunit binding could influence cAMP binding through a Asp306/Asp309-Arg359-cAMP network again suggests that C-subunit binding could facilitate the release of cAMP from the cB domain.

Additional changes in the amide exchange of peptides exclusive of the PBCs were also observed within the cAMP-binding domains, but they were observed only in the cB domain. The cB domain appears to be more malleable upon C-subunit binding than the cA domain. The influence of the C-subunit on domain B is somewhat surprising because the cB domain was believed to act solely as a gatekeeper to control cAMP binding to the cA domain. Furthermore, deletion of the entire cB domain in RIα had little effect on binding of RIα to the C-subunit. The effect of C-subunit binding on amide exchange within the RIIβ cB domain suggests that domain B may play a role in interactions with the C-subunit. The increased solvent accessibility within the cB domain upon C-subunit binding may help to "prime" the domain for the inevitable dissociation of the holoenzyme.

EXAMPLE 3

DXMS Analysis Used to Refine Structure Determinations

DXMS analysis was attempted on the twenty-four Thermotoga maritima proteins listed below in Table 2, which exhibited either different degrees of resistance to crystallization or formed crystals that did not diffract X-rays sufficient for structure determination.

TABLE 2

*T. maritima* proteins

Did not crystallize

| TIGR_TMAC | TIGR_description, nearest homolog. | Molecular Weight | Length |
|---|---|---|---|
| TM0212 | glycine cleavage system H protein (gcvH) {*Escherichia coli*} | 13914.56 | 124 |
| cTM0855 | ribosome binding factor A {*Stigmatella aurantiaca*} | 15546.89 | 131 |
| TM1171 | transcriptional regulator, crp family {*Pseudomonas stutzeri*} | 23394.46 | 201 |
| TM1706 | transcription elongation factor, greA/greB family {*Bacillus subtilis*} | 17848.31 | 156 |
| TM0160 | conserved hypothetical protein {*Aquifex aeolicus*} | 20551.31 | 181 |
| TM1773 | conserved hypothetical protein | 63642.64 | 538 |

{*Methanococcus jannaschii*}
Gave few crystals

| TIGR_TMAC | TIGR_description | Molecular Weight | Length |
|---|---|---|---|
| TM0913 | mazG protein {*Haemophilus influenzae*} | 29804.83 | 255 |
| TM1816 | conserved hypothetical protein {*Pyrococcus horikoshii*} | 13625.33 | 124 |
| TM0320 | heavy metal binding protein {*Helicobacter pylori*} | 7853 | 67 |
| TM1079 | ribosomal protein L11 methyl-transferase, putative {*Aquifex aeolicus*} | 30280 | 264 |
| TM1172 | prismane protein {*Methanobacterium thermoautotrophicum*} | 47957.4 | 431 |
| TM1764 | conserved hypothetical protein | 14048.86 | 121 |

TABLE 2-continued

*T. maritima* proteins

{*Lactococcus lactis*}
Diffracted poorly

| TIGR_TMAC | TIGR_description | Molecular Weight | Length |
|---|---|---|---|
| TM0505 | groES protein (groES) {*Mycobacterium tuberculosis*} | 10333.04 | 92 |
| TM1464 | conserved hypothetical protein {*Escherichia coli*} | 31727.99 | 285 |
| TM1733 | conserved hypothetical protein {*Aquifex aeolicus*} | 29241.5 | 258 |
| TM0486 | conserved hypothetical protein {*Clostridium perfringens*} | 10805.43 | 94 |
| TM1080 | sugar-phosphate isomerase {*Aquifex aeolicus*} | 15867.2 | 143 |
| TM1158 | conserved hypothetical protein | 26900.03 | 227 |

{*Archaeoglobus fulgidus*}
Diffracted well, and crystal structure solved.

| TIGR_TMAC | TIGR_description | Molecular Weight | Length |
|---|---|---|---|
| TM0064 | uronate isomerase, putative {*Escherichia coli*} | 52305.51 | 451 |
| TM0449 | thy1 protein {*Borrelia burgdorferi*} | 26003.96 | 220 |
| TM0542 | malate oxidoreductase {*Streptococcus bovis*} | 41043.32 | 376 |
| TM0665 | cysteine synthase (cysK) {*Bacillus subtilis*} | 31130.23 | 291 |
| TM1056 | periplasmic divalent cation tolerance protein (cutA) {*Archaeoglobus fulgidus*} | 12177.07 | 101 |
| TM0269 | hypothetical protein | 22890.29 | 202 |

Data acquisition and analysis were completed for twenty-one of these proteins. Several unstructured regions were predicted and localized. When compared with those targets of known structure, the DXMS method correctly localized small regions of disorder. DXMS analysis was correlated with propensity of targets to crystallize and further utilized to define truncations with improved crystallization properties. Truncations defined solely on DXMS analysis demonstrated greatly improved crystallization success.

A. Protein Expression and Purification.

Protein preparations for twenty-four T.maritima proteins and the subsequently designed daughter constructs were prepared as is known in the art. In brief, all targets were expressed in *E. coli* DLA1 from plasmids based the expression vector pMH1 or pMH4. These vectors encode a 12 amino acid tag containing the first 6 amino acids of thioredoxin and 6 His residues placed at the N-terminus to enhance expression and to allow for rapid affinity purification. Protein expression was performed in TB media containing 1% glycerol (v/v) and 50 mM MOPS pH 7.6. Expression was induced by the addition of 0.15% arabinose for 3 hours. Bacteria were lysed by sonication after a freeze-thaw procedure in Lysis Buffer (50 mM Tris pH 7.9, 50 mM NaCl, 1 mM $MgC_2$, 0.25 mM TCEP, 1 mg/ml lysozyme) and cell debris pelleted by centrifugation at 3600×g for 60 minutes. The soluble fraction was applied to a nickel chelate resin (Pharmacia) previously equilibrated with Equilibration Buffer (50 mM $KH_2PO_4$ pH 7.8, 0.25 mM TCEP, 10% v/v glycerol, 0.3M NaCl) containing 20 mM imidazole. The resin was washed with Equilibration Buffer containing 40 mM imidazole, and protein was eluted with Elution Buffer (20 mM Tris pH 7.9, 10% v/v glycerol, 0.25 mM TCEP, 300 mM imidazole). Buffer exchange was performed to remove imidazole from the protein eluate and the protein into 10 mM Tris HCl with 150 mM NaCl, and concentrated in Millipore spin concentrators to a final volume of 0.75 ml, with final protein concentrations ranging from 15 to 50 mg/ml.

B. Establishment of Protein Fragmentation Probe Maps.

Aliquots of each of the twenty four proteins were adjusted to a concentration of 10 mg/ml in Tris-Buffered Saline (5 mM Tris, 150 mM NaCl, pH 7.0; TBS), and all subsequent steps performed at 0° C., on melting ice. In a 4° C. cold room, five µl of each solution was further diluted with 15 µl of TBS in a microtiter plate employing multichannel pipettors for simultaneous manipulation. Thirty microliters of a stock "exchange quench" solution (0.8% formic acid, 1.6 M GuHCl) was then added to each sample (final concentration 0.5% formic acid, 1.0 M GuHCl), samples transferred to autosampler vials, and then frozen on dry ice within one minute after addition of quench solution. Vials with frozen samples were stored at −80° C. until transferred to the dry ice-containing sample basin of the cryogenic autosampler module of the DXMS apparatus. Samples were individually melted at 0° C., then injected (45 µl) and pumped through protease columns (0.05% TFA, 250 µl/min, 16 seconds exposure to protease). Proteolysis used immobilized pepsin (66 µl column bed volume, coupled to 20 AL support from PerSeptive Biosystems at 30 mg/ml). Protease-generated fragments were collected onto a C18 HPLC column, eluted by a linear acetonitrile gradient (5 to 45% B in 30 minutes; 50 µl/min; solvent A, 0.05% TFA; solvent B, 80% acetonitrile, 20% water, 0.01% TFA), and effluent directed to the mass spectrometer with data acquisition in either MS1 profile mode or data-dependent MS2 mode. Mass spectrometric analyses used a Thermo Finnigan LCQ electrospray ion trap type mass spectrometer operated with capillary temperature at 200° C. or an electrospray Micromass Q-TOF mass spectrometer. The Sequest software program (Thermo Finnigan Inc) identified the likely sequence of the parent peptide ions. Tentative identifications were tested with specialized DXMS data reduction software developed in collaboration with Sierra Analytics, LLC, Modesto, Calif. This software searches MS1 data for scans containing each of the peptides, selects scans with optimal signal-to-noise, averages the selected scans, calculates centroids of isotopic envelopes, screens for peptide misidentification by comparing calculated and known centroids, then facilitates visual review of each averaged isotopic envelope allowing an assessment of "quality" (yield, signal/noise, resolution), and confirmation or correction of peptide identity and calculated centroid.

C. On-Exchange Deuteration of Proteins.

After establishment of fragmentation maps for each protein, amide hydrogen exchange-deuterated samples of each of the twenty-four proteins were prepared and processed exactly as above, except that 5 µl of each protein stock solution was diluted with 15 µl of Deuterium Oxide (D₂O), containing 5 mM Tris, 150 mM NaCl, pD (read) 7.0, and incubated for ten seconds at 0° C. before quench and further processing. Data on the deuterated sample set was acquired in a single automated 30-hour run, and subsequent data reduction performed on the DXMS software. Corrections for loss of deuterium-label by individual fragments during DXMS analysis (after "quench") were made through measurement of loss of deuterium from reference protein samples that had been equilibrium-exchange-deuterated under denaturing conditions. The total time elapsed for data acquisition and analysis (both fragmentation maps and deuteration study) was two weeks, and a total of 100 micrograms of each protein was used to complete the study. The personnel performing the data acquisition and reduction part of the study were unaware of the identity or crystallization histories of the proteins while data was being acquired and processed. For subsequent comparative analysis of the exchange rates of amide hydrogens within daughter protein constructs versus their parents, both proteins were contemporaneously on-exchanged as above, but quenched at varying times (10 sec, 30 sec, 100 sec, 300 sec, 1000 sec, 3000 sec, 10,000 sec, and 30,000 sec), and further processed as above, employing the fragmentation maps established for the parent protein.

D. Equipment Configuration.

The equipment configuration consisted of electrically actuated high pressure switching valves (Rheodyne), connected to two position actuators from Tar Designs Inc., Pittsburgh. A highly modified Spectraphysics AS3000 autosampler, partially under external PC control, employed a robotic arm to lift the desired frozen sample from the sample well, then automatically and rapidly melted and injected it under precise temperature control. The autosampler basin was further thermally insulated and all but twenty vial positions were filled with powdered dry ice sufficient to keep samples colder than −45° C. for 18 hours. Four HPLC pumps (Shimadzu LC-10AD) were operated by a Shimadzu SCL-10A pump controller. One produced forward flow over the protease columns, another backflushed the protease column after sample digestion (0.05% aqueous TFA), and two delivered solvents to a downstream HPLC column for gradient elution (A: 0.05% aqueous TFA; B; 80% acetonitrile, 20% water, 0.01% TFA; 1×50 mm C18 Vydac # 218MS5105, pH 2.3). Valves, tubing, columns and autosampler were contained within a refrigerator at 2.8° C. with protease and HPLC columns immersed in melting ice. The timing and sequence of operation of the DXMS apparatus fluidics were controlled by a personal computer running an in-house written LabView-based program, interfaced to solid-state relays (digital input/output boards, National Instruments), controlling pumps, valve actuators, and MS data acquisition.

E. Protein Crystallization and Diffraction Data Acquisition.

Proteins were crystallized using the vapor diffusion method with 50 nl or 250 nl protein and 50 nl or 250 nl mother liquor respective volumes as sitting drops on customized microtiter plates (Greiner). Each protein was set up using 480 standard crystallization conditions (Wizard I/II, Wizard Cryo I/II [Emerald Biostructures], Core Screen I/II, Cryo I, PEG ion, Quad Grid [Hampton Research]) at 4° C. and 20° C. Images of each crystal trial were taken at least twice, typically at 7 and 28 days after setup with an Optimag Veeco Oasis 1700 imager. Each image was evaluated using a crystal detection algorithm (Spraggon et al., *Acta. Cryst. D.* 58: 1915-1923, 2002) and scored for the presence of crystals. Images at days 7 and 28 were also evaluated manually. Diffraction data was provided by the JCSG from collection at 100K on the beamlines of the SSRL Structural Molecular Biology/Macromolecular Crystallography Resource.

F. DXMS Allows Definition of Rapidly Exchanging Regions of T.maritima Proteins.

Fragmentation maps covering the entirety of each protein's sequence were obtained for sixteen proteins, nearly complete coverage in five proteins, and inadequate coverage obtained for three proteins; TM0855, TM1773, and TM1764. Exchange-deuteration studies were performed on the twenty-one proteins that had generated useful fragmentation maps. FIG. 19 presents the 10-second exchange map for each protein. Label was manually assigned to residue positions within the protein by first optimizing consensus in deuterium content of overlapping peptide probes, followed by further clustering of labeled amides together in the center of unresolved regions (with vertical bars indicating the range of possible location assignments). The percentages indicate the percent of amides rapidly exchanging in sequence segments of four or more contiguous amino acids. Circled regions indicate rapidly exchanging segments.

The duration of labeling (10 seconds) was calculated to be sufficient to selectively deuterate primarily freely solvated amides. This was confirmed by first fragmenting reference proteins by pepsin to yield unstructured peptides, followed by deuterium-exchange labeling the resulting peptide mix for 10 seconds at pH 7.0, 0° C. as above, and then quenching and subjecting the mixture to DXMS analysis, but without repeat proteolysis. All peptides prepared and then deuterated under these conditions were found to be saturation-labeled with a 10-second period of on-exchange.

G. DXMS Analysis Correctly Localized Disordered Regions in Control Proteins With Previously Determined 3-D Structures.

Interpretation of the exchange maps of these T.maritima proteins was guided by the expectation of two patterns of fast exchange labeling: structurally stable, but well solvated, rapidly exchanging residues (one to three contiguous residues) vs. labeling of longer stretches of sequence (four or more residues) indicative of disorder. This dichotomy presumed that three contiguous amino acids was likely the largest number needed to complete a structurally stable turn on the surface of a protein.

As an example, TM0449 is a protein that had crystallized and diffracted well, and for which the structure had been solved (Mathews et al., *Structure* 11: 677-690, 2003). Its exchange map demonstrated two long segments ($\geq 4$ residues in each) with rapid exchange (circled regions in FIG. 19), and several isolated rapidly exchanging amides in groups of 3 or less, scattered throughout the sequence. Both rapidly exchanging segments corresponded to regions of disorder in the crystal, confirming the ability of DXMS data to detect and localize such disordered regions. Interestingly, these regions also appear to be involved in the binding of the enzyme substrate and adopt a structured conformation after binding ligand (Mathews et al., supra). This suggests that DXMS can also provide some localized prediction of substrate and cofactor binding. Similar comparisons were performed for other proteins with known structures with regions of internal disorder typically mapping to loop regions.

H. Many Poorly Crystallizing T. maritima Proteins Contain Substantial Disorder.

Another protein, TM0505, demonstrated rapid exchange in three segments containing four or more residues, which together constituted 16% of its sequence. While this T.maritima protein had previously produced only poorly diffracting crystals, it is a close homolog of the GroES heat shock protein of *M. tuberculosis*, for which a crystal structure had been previously obtained as the GroES heptamer, and as a complex with the GroEL subunit; GroELS (Ranson et al., *Cell.* 28:107:869-79, 2001; Roberts et al., *J. Bacteriol.* 185:4172, 2003). When the T.maritima residues with rapid exchange are mapped upon the *M. tuberculosis* structures, they predominantly localize to the disordered residues in GroES that make contacts with the GroEL binding surface upon complex formation.

The exchange map for the poorly crystallizing protein TM1816 is dominated by several substantial regions of disordered sequence, constituting 17.7% of its residues. Similarly, the poorly crystallizing proteins TM1706, TM1733 and TM1079 exhibit substantial portions of their sequence in rapidly exchanging stretches of 4 or more residues (11.5%; 6.6% and 5.7% respectively).

Three of the poorly crystallizing proteins had disorder primarily at the carboxy-terminus; TM0160; TM1171; and TM1172. These targets offer a straightforward route to domain optimization by simply deleted the disordered C-terminus. The optimization of two of these targets is described below.

I. Daughter Constructs of T. maritima Proteins can be Prepared That are Selectively Depleted of c-Terminal Disorder, With Preservation of Retained Parental Structure Confirmed by Repeat DXMS Analysis.

Truncation mutants ("daughters") of poorly crystallizing TM0160 and TM1171 proteins ("parents") were prepared, in which the c-terminal disordered region(s) of both parental proteins were deleted. The fragmentation patterns produced by pepsin often exhibited preferences for sites near exchange-defined stretches of disorder. Several daughter constructs were prepared from each parent, in part guided by the location of the "preferred" pepsin cut sites. TM0160 does not have known structural homologs. For both TM0160 and TM1171, deletions were designed solely on the basis of DXMS experimental data. The daughter constructs expressed well as soluble protein. Parent TM0160, and its longest daughter (D3), were on-exchanged variously for 10, 100, 1,000, and 10,000 seconds at 0° C., exchange-quenched and subjected to comparative DXMS analysis as described above. The resulting 10-second exchange maps for parent and D3 daughter had virtually identical patterns (see FIG. 19), and detailed analysis of the longer exchange times demonstrated that truncation daughter D3 had a stability profile substantially identical to that the TM0160 parent in retained sequence. Similarly, each of the four TM1171 daughter constructs expressed well as soluble protein, and had DXMS stability maps identical with that of the TM1171 parent in retained sequence regions.

J. Structure—Preserving Deletion Constructs to Two T. maritima Parents Show Marked Improvement in Crystallization Efficiency.

Figure 20:
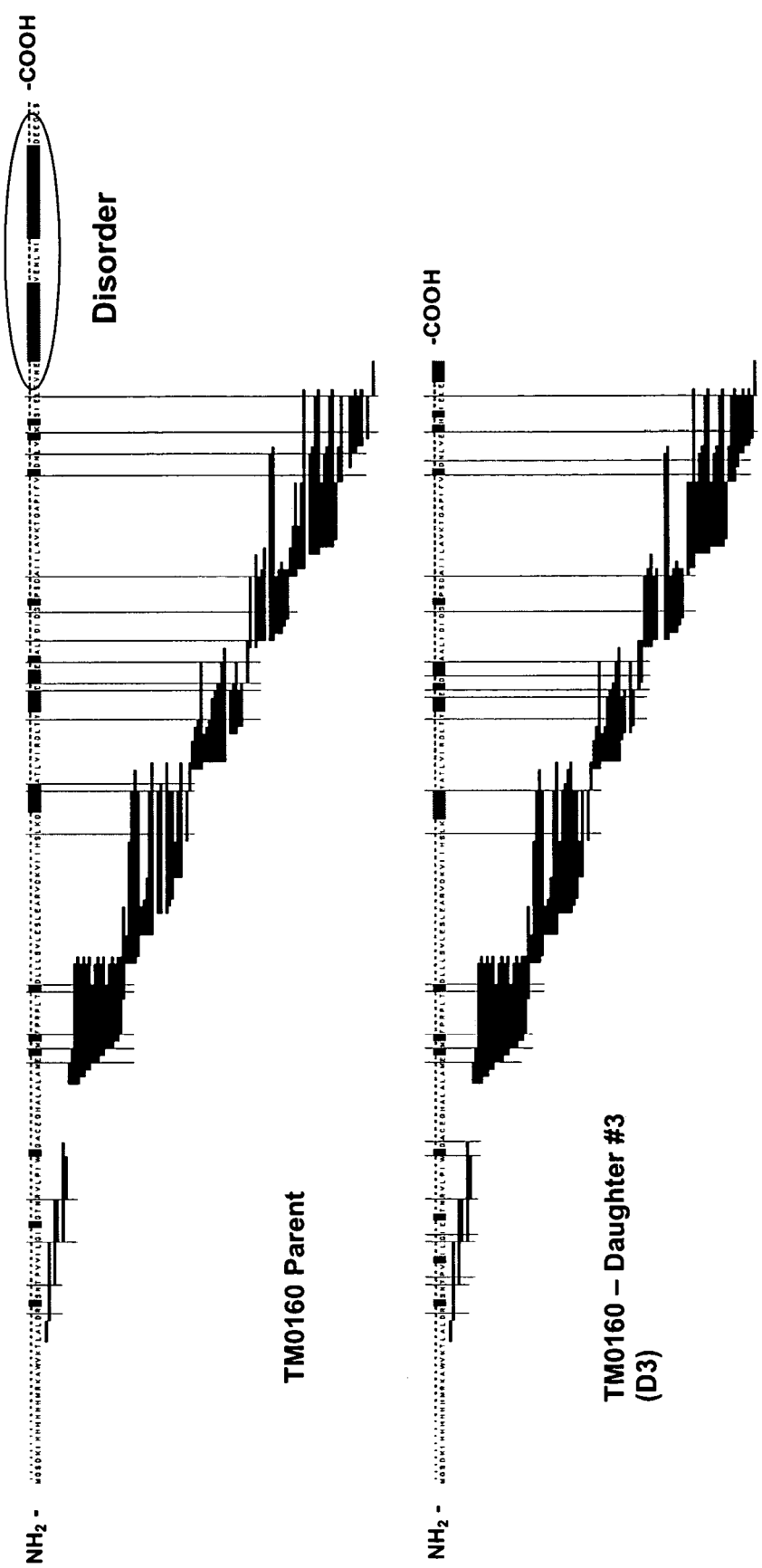
FIG. 20 illustrates the exchange map of TM0160 parent protein as compared to a daughter construct containing a C-terminal deletion of the disordered region (SEQ ID NOs: 16 and 17).

The TM0160 parent and TM0160-D3 truncation mutant proteins (see FIG. 20) were entered into crystallization trials. A total of 480 commercially available crystallization solutions were used under 4 and 20° C. as described above. From multiple protein preparations and crystallization attempts the parental full-length protein showed marginal crystals for only 3 of 2400 total attempts. In contrast using the same 480 crystallization solutions, 76 crystal hits were obtained from 1920 attempts. Crystals from the D3 truncation were visibly better-formed and diffracted well. Ultimately a 1.9 Å dataset from selenomethionine-containing protein was obtained and used to solve the structure of this deletion. Similarly, full length TM1171 parent protein was subjected to repeated crystallization attempts. Whereas the full-length protein showed very marginal crystallization propensity (5 out of 2400 attempts), each of the four daughter constructs showed marked improvement in crystallization with the D4 construct ultimately resulting in a 2.1 Å dataset that was used to determine the 3-dimensional structure.

K. Summary.

DXMS analysis can reliably detect and localize disordered sequence within otherwise structured proteins. As shown in this example, stability profiles were determined for 21 T. maritima proteins examined for crystallization studies. Six of these proteins were found to have a higher fraction of their sequence present in disordered stretches than did any of the well-crystallizing constructs. Three proteins had primarily c-terminal disorder, and five proteins had primary sequences in which multiple disordered segments were interspersed with structured segments. Invention methods thus allowed the determination of the DXMS-protein stability profiles and provided these insights at speeds matching the needs of HT structural genomics.

This example also shows it is possible to construct (re)design a protein to selectively delete disorder, with a straightforward analysis of such DXMS stability profiles, and that subsequent comparative DXMS study can rapidly and reliably determine the degree to which expressed daughter constructs, designed on the basis of parental stability profiles, preserve the parental structure in retained sequence. While many bioinformatic approaches can often be applied to well-characterized protein folds, DXMS offers a particular advantage for those targets of novel structure. Experimental data is generated specific for the target of interest. The exchange rates can be localized to specific amino acid residues, greatly refining the truncation definition. Unlike NMR methods which can provide exchange data, DXMS requires only μg amounts of soluble protein and data reduction can be performed in a rapid timescale.

Finally, this example shows that DXMS stability profile-guided construct re-design can produce well-crystallizing derivatives of poorly crystallizing proteins. Robustly producing, well-crystallizing, and well-diffracting daughter truncation constructs of T. maritima parent proteins that had behaved poorly in prior crystallization efforts are demonstrated herein. This example also confirmed that the well-crystallizing daughters preserved parental exchange rate patterns, indicating that they had retained parental structure with high fidelity.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein.

The examples provided here are representative of preferred embodiments, are exemplary, and are not intended as limitations on the scope of the invention. Modifications therein and other uses will occur to those skilled in the art. These modifications are encompassed within the spirit of the invention.

The disclosure of all publications cited above are expressly incorporated herein by reference, each in its entirety, to the same extent as if each were incorporated by reference individually.

That which is claimed is:

1. A method for improving the success of crystallizing a protein or improving the quality of a crystallized protein for crystallographic structure determination thereof, said method comprising:
(a) identifying at least one unstructured region of said protein by hydrogen exchange analysis;
(b) deleting at least one unstructured region of said protein identified by hydrogen exchange analysis; and
c) subjecting to crystallization, and structure determination one or more modified form(s) of said protein according to step (b).

2. A method according to claim 1, wherein said hydrogen exchange analysis comprises determining the quantity of isotopic hydrogen or the rate of hydrogen exchange, or both the quantity of isotopic hydrogen and the rate of hydrogen exchange, of a plurality of peptide amide hydrogens exchanged for said isotopic hydrogen in a protein labeled with a hydrogen isotope other than 1H.

3. A method according to claim 2, wherein said determining the quantity of isotopic hydrogen or the rate of hydrogen exchange or both the quantity of isotopic hydrogen and the rate of hydrogen exchange comprises:
(a) fragmenting said labeled protein into a plurality of fragments under slowed hydrogen exchange conditions;
(b) identifying which fragments of said plurality of fragments are labeled with isotopic hydrogen;
(c) progressively degrading each fragment of said plurality of fragments to obtain a series of subfragments, wherein each subfragment of said series is composed of about 1-5 fewer amino acid residues than the preceding subfragment in the series; and
(d) correlating the amount of isotopic hydrogen associated with each subfragment with an amino acid sequence of said fragment from which said subfragment was generated, thereby determining the quantity of isotopic hydrogen or the rate of hydrogen exchange or both the quantity of isotopic hydrogen and the rate of exchange of a plurality of peptide amide hydrogens exchanged for said isotopic hydrogen in a protein labeled with a hydrogen isotope other than 1H.

4. A method according to claim 3, wherein said fragmenting in step (a) comprises contacting said labeled protein with at least one acid stable endopeptidase.

5. A method according to claim 4, wherein said at least one acid stable endopeptidase is coupled to a support material.

6. A method according to claim 5, wherein said at least one acid stable endopeptidase is selected from the group consisting of pepsin, cathepsin D, newlase, *Aspergillus* proteases, thermolysin, protease type XIII, and combinations of any two or more thereof.

7. The method according to claim 6, wherein said at least one acid stable endopeptidase is pepsin.

8. A method according to claim 3, wherein said progressively degrading comprises contacting said fragments with at least one acid stable exopeptidase.

9. A method according to claim 8, wherein said at least one acid stable exopeptidase is coupled to a support material.

10. A method according to claim 9, wherein said progressively degrading comprises contacting said fragments with at least one acid resistant carboxypeptidase.

11. A method according to claim 10, wherein said at least one acid resistant carboxypeptidase is carboxypeptidase P.

12. A method according to claim 9, wherein said fragmenting in step (a) comprises contacting said labeled protein with at least one acid stable endopeptidase selected from the group consisting of pepsin, newlase, cathepsin C, *Aspergillus* proteases, protease type XIII, thermolysin, and combinations of any two or more thereof.

13. A method according to claim 2, wherein said determining the quantity of isotopic hydrogen or the rate of hydrogen exchange or both the quantity of isotopic hydrogen and the rate of exchange comprises:
(a) generating a population of sequence-overlapping fragments of said labeled protein by treatment with at least one endopeptidase under conditions of slowed hydrogen exchange, and then (b) deconvoluting fragmentation data acquired from said population of sequence-overlapping endopeptidase-generated fragments.

14. A method according to claim 13, wherein said population of sequence-overlapping endopeptidase-generated fragments is generated by cleaving said protein with an endopeptidase selected from the group consisting of a serine endopeptidase, a cysteine endopeptidase, an aspartic endopeptidase, a metalloendopeptidase, a threonine endopeptidase, and combinations of any two or more thereof.

15. A method according to claim 13, wherein said at least one endopeptidase is coupled to a support material.

16. A method according to claim 13, wherein said at least one endopeptidase is pepsin.

17. A method according to claim 13, wherein said population of sequence-overlapping endopeptidase-generated fragments is generated by two or more endopeptidases used in combination.

18. A method according to claim 13, wherein said at least one endopeptidase is newlase or *Aspergillus* protease XIII.

19. A method according to claim 13, wherein said at least one endopeptidase is an acid-tolerant *Aspergillus* protease.

20. A method according to claim 13, wherein said population of sequence-overlapping endopeptidase-generated fragments is generated at a pH of about 1.8-3.4.

21. A method according to claim 20, wherein said population of sequence-overlapping endopeptidase-generated fragments is generated at a pH of about 2-3.

22. A method according to claim 21, wherein said population of sequence-overlapping endopeptidase-generated fragments is generated at a pH of about 2.0-2.5.

23. A method according to claim 21, wherein said population of sequence-overlapping endopeptidase-generated fragments is generated at a pH of about 2.5-3.0.

24. A method according to claim 13, wherein said population of sequence-overlapping endopeptidase-generated fragments is generated in less than five minutes.

25. A method according to claim 24, wherein said population of sequence-overlapping endopeptidase-generated fragments is generated in about one minute or less.

26. A method according to claim 25, wherein said population of sequence-overlapping endopeptidase-generated fragments is generated in about 40 seconds or less.

27. A method according to claim 13, wherein deconvoluting comprises:
comparing the quantity of isotope and/or rate of exchange of hydrogen at a peptide amide hydrogen with said isotope on a plurality of endopeptidase fragments in said population of sequence-overlapping endopeptidase-generated fragments with the quantity of isotope and/or rate of exchange of hydrogen at a peptide amide hydrogen on at least one other endopeptidase fragment in said population of sequence-overlapping endopeptidase-generated fragments,
wherein said quantities are corrected for back-exchange losses subsequent to the initiation of slowed exchange conditions in an amino acid sequence-specific manner.

28. A method according to claim 27, wherein labeled peptide amides are localized in an amino acid sequence-specific manner by measuring rates of exchange as a function of time under slowed exchange conditions.

29. A method according to claim 13, wherein said population of sequence-overlapping endopeptidase-generated fragments contains a plurality of sequence-overlapping fragments, wherein more than half of the members of said population have sequences that overlap other members of said population over all but 1-5 amino acid residues.

30. A method according to claim 13, wherein a majority of members of said population of sequence-overlapping endopeptidase-generated fragments is present in an analytically sufficient quantity to permit its further characterization.

31. A method according to claim 13, wherein determining the quantity and rate of exchange of peptide amide hydrogen(s) is carried out contemporaneously with generating a population of sequence-overlapping endopeptidase-generated fragments.

32. A method according to claim 13, further comprising determining off-exchange rates of labeled peptide amides under conditions of slowed hydrogen exchange and random-coil conditions from a plurality of fragments and fragment differences.

33. A method according to claim 3 or claim 13, wherein said isotopic hydrogen is deuterium.

34. A method according to claim 33, wherein the presence and quantity of said deuterium on said fragments of said labeled protein is determined by measuring the mass of said fragments.

35. A method according to claim 34, wherein said measuring is performed using mass spectrometry.

36. A method according to claim 3 or claim 13, further comprising the use of conditions that effect protein denaturation under slowed exchange conditions prior to generation of said fragments.

37. A method according to claim 36, wherein said conditions comprise contacting said labeled protein with guanidine hydrochloride at a concentration of about 0.05-4 M.

38. A method according to claim 36, wherein said conditions comprise contacting said labeled protein first with guanidine thiocyanate at a concentration of about 1.5-4 M, followed by dilution into guanidine hydrochloride at a concentration of about 0.05-4 M.

39. A method according to claim 3 or claim 13, further comprising disrupting disulfide bonds in the labeled protein prior to generating said fragments.

40. A method according to claim 39, wherein said disrupting comprises contacting the labeled protein with a phosphine.

41. A method according to claim 1, wherein said protein is a protein that is resistant to crystallization or that forms crystals that do not diffract X-rays sufficient for structure determination.

42. A method for improving success of achieving crystallographic structure determination of a protein, said method comprising:
(a) generating one or more modified forms of said protein by deleting at least one unstructured region of said protein identified by hydrogen exchange analysis; and
(b) subjecting to crystallization and structure determination said one or more modified forms of said protein.

* * * * *